US011102985B2

(12) United States Patent
Carney et al.

(10) Patent No.: US 11,102,985 B2
(45) Date of Patent: *Aug. 31, 2021

(54) BIOMASS COMPOSITIONS AND METHODS FOR MAKING THE SAME

(71) Applicant: HELIAE DEVELOPMENT, LLC, Gilbert, AZ (US)

(72) Inventors: Laura Carney, Gilbert, AZ (US); Michael Miller, Chandler, AZ (US); Amy Rial, Chandler, AZ (US); Connor Osgood, Gilbert, AZ (US)

(73) Assignee: HELIAE DEVELOPMENT, LLC, Gilbert, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/880,588

(22) Filed: May 21, 2020

(65) Prior Publication Data
US 2020/0281211 A1 Sep. 10, 2020

Related U.S. Application Data

(62) Division of application No. 16/185,652, filed on Nov. 9, 2018, now Pat. No. 10,701,941.

(60) Provisional application No. 62/584,311, filed on Nov. 10, 2017, provisional application No. 62/642,729, filed on Mar. 14, 2018, provisional application No. 62/680,373, filed on Jun. 4, 2018.

(51) Int. Cl.
A01N 65/03 (2009.01)
A01N 61/00 (2006.01)
A01H 13/00 (2006.01)
A01H 3/00 (2006.01)
C12N 1/12 (2006.01)
C05F 11/08 (2006.01)

(52) U.S. Cl.
CPC .............. A01N 65/03 (2013.01); A01H 3/00 (2013.01); A01H 13/00 (2013.01); A01N 61/00 (2013.01); C05F 11/08 (2013.01); C12N 1/12 (2013.01)

(58) Field of Classification Search
None
See application file for complete search history.

(56) References Cited

U.S. PATENT DOCUMENTS

| 3,444,647 | A | ‡ | 5/1969 | *Masahito | A01G 33/00 47/1.4 |
| 3,889,418 | A | ‡ | 6/1975 | Porter | A01G 33/00 47/1.4 |
| 4,235,043 | A | ‡ | 11/1980 | Harasawa | A01G 9/1438 47/1.4 |
| 4,551,164 | A | ‡ | 11/1985 | Tenzer | C05F 11/08 71/6 |
| 4,774,186 | A | ‡ | 9/1988 | Schaefer, Jr. | C05F 11/08 435/25 |
| 4,846,870 | A | ‡ | 7/1989 | Weltzien | C05F 11/00 71/24 |
| 4,919,702 | A | ‡ | 4/1990 | Weltzien | C05G 5/23 71/24 |
| 5,034,416 | A | ‡ | 7/1991 | Smith | A61K 9/2009 424/71 |
| 5,130,242 | A | ‡ | 7/1992 | Barclay | A61K 31/20 435/13 |
| 6,083,293 | A | ‡ | 7/2000 | Bath | C05C 9/00 71/16 |
| 6,893,479 | B2 | ‡ | 5/2005 | Eswaran | C05F 11/00 71/23 |
| 7,030,061 | B2 | ‡ | 4/2006 | De La Fuente Jimenez | C05F 11/00 504/11 |
| 7,892,311 | B2 | ‡ | 2/2011 | Briand | A01N 65/03 71/23 |
| 8,122,637 | B2 | ‡ | 2/2012 | Blotsky | A01C 21/00 47/1.4 |
| 8,133,920 | B2 | ‡ | 3/2012 | Johnson | A61K 36/185 514/74 |
| 8,241,868 | B2 | ‡ | 8/2012 | Higashiyama | C07F 9/103 435/41 |
| 8,367,372 | B2 | ‡ | 2/2013 | Calt, Jr. | C12P 7/52 435/41 |
| 8,563,839 | B2 | ‡ | 10/2013 | Scheer | A01N 3/00 800/32 |
| 8,614,165 | B2 | ‡ | 12/2013 | Goodwin | A01N 63/00 504/10 |

(Continued)

FOREIGN PATENT DOCUMENTS

CN 1063413 C 3/2001
CN 101352249 1/2009

(Continued)

OTHER PUBLICATIONS

Irrigation Research Foundation and BioFlora, Case Study Yellow Field Corn, http://www.bioflora.com/case-study-corn/, accessed Apr. 10, 2014, 2 pages.‡
Jha, et al., "Efficacy of new Inexpensive Cyanobacterial Biofertilizer including its Shelf Life," World J. of Micorbiology and Biotechnology, v22 n1, 2006, pp. 73-79.‡
Khan, et al., "Seaweed Extracts as Biostimulants of Plant Growth and Development," J. Plant Growth Regul., 2009, 28, pp. 386-399.‡
Leonian, "Effect of Auxins from Some Green Algae upon Phytophthora Cactomm," Botanical Gazette, v 97, n 4, Jun. 1936, pp. 854-859.‡
Mahdi, et al., "Bio-Fertilizers in Organic Agriculture," J. of Phytology 2010, 2(10), pp. 42-54.‡

(Continued)

Primary Examiner — Alton N Pryor
(74) Attorney, Agent, or Firm — Cao Intellectual Property Services, LLC; Veronica-Adele R. Cao

(57) ABSTRACT

The present invention discloses biomass compositions for improving shelf life, increasing fruit water retention, and/or decreasing needle-drop in conifer species and methods for making the same. The composition comprises pasteurized microalgae selected from *Chlorella*, *Aurantiochytrium*, *Scenedesmus*, or any combination thereof.

21 Claims, 5 Drawing Sheets

(56) References Cited

U.S. PATENT DOCUMENTS

| | | | | |
|---|---|---|---|---|
| 8,623,110 B2 ‡ | 1/2014 | Bevans | | C05F 5/002 71/15 |
| 8,623,423 B2 ‡ | 1/2014 | Cook | | C05D 9/02 424/65 |
| 9,386,774 B2 ‡ | 7/2016 | Shinde | | C12N 1/12 |
| 10,631,543 B2 * | 4/2020 | Carney | | A01G 22/05 |
| 10,645,937 B2 * | 5/2020 | Carney | | A01N 65/03 |
| 10,694,751 B2 * | 6/2020 | Carney | | A01N 63/30 |
| 10,701,941 B2 * | 7/2020 | Carney | | A01N 63/10 |
| 2003/0068303 A1 ‡ | 4/2003 | Selvig | | A01N 63/30 424/93 |
| 2004/0031302 A1 ‡ | 2/2004 | Eswaran | | C05F 11/00 71/23 |
| 2004/0049062 A1 ‡ | 3/2004 | Bijl | | A23K 20/158 554/1 |
| 2005/0119127 A1 ‡ | 6/2005 | Cambri | | C05F 11/00 504/17 |
| 2009/0266125 A1 ‡ | 10/2009 | Doan | | C05F 17/10 71/9 |
| 2011/0142675 A1 | 6/2011 | Piccirilli | | |
| 2011/0142875 A1 ‡ | 6/2011 | Piccirilli | | A61K 8/9722 424/19 |
| 2011/0312023 A1 ‡ | 12/2011 | Chuu | | A23K 10/37 435/41 |
| 2011/0314881 A1 ‡ | 12/2011 | Hatcher | | C05F 5/004 71/11 |
| 2012/0094831 A1 ‡ | 4/2012 | Bartley, Jr. | | A01N 65/00 504/10 |
| 2012/0192605 A1 ‡ | 8/2012 | McSpadden Gardener | | C05G 5/30 71/7 |
| 2012/0208254 A1 ‡ | 8/2012 | Smith | | C12M 43/08 435/16 |
| 2012/0247164 A1 ‡ | 10/2012 | Dahms | | C05C 3/00 71/8 |
| 2013/0102465 A1 ‡ | 4/2013 | Lovatt | | C05B 17/00 504/13 |
| 2014/0002452 A1 ‡ | 1/2014 | Levin | | G06T 7/85 345/41 |
| 2014/0011246 A1 ‡ | 1/2014 | Sims | | C12P 7/16 435/13 |
| 2014/0024529 A1 ‡ | 1/2014 | Smith | | C05F 5/008 504/11 |
| 2014/0026258 A1 ‡ | 1/2014 | Bettiol | | A61K 35/74 800/29 |
| 2014/0090431 A1 ‡ | 4/2014 | Blotsky | | C05F 11/08 71/11 |
| 2014/0298717 A1 ‡ | 10/2014 | Ayers | | C05D 9/02 47/1.4 |

FOREIGN PATENT DOCUMENTS

| | | |
|---|---|---|
| CN | 102001895 | 4/2011 |
| CN | 102153413 | 8/2011 |
| CN | 102616932 | 8/2012 |
| CN | 102060578 | 7/2013 |
| CN | 103990155 | 8/2014 |
| GB | 1432039 | 4/1976 |
| JP | 58180404 A ‡ | 10/1983 |
| JP | 2001151586 | 6/2001 |
| JP | 2001151586 A ‡ | 6/2001 |
| KR | 102005091318 | 9/2005 |
| KR | 102007066461 | 6/2007 |
| KR | 101232284 | 2/2013 |
| KR | 101232288 | 2/2013 |
| RU | 2375714 C2 ‡ | 12/2009 |
| WO | 2004085343 | 10/2004 |
| WO | 2007122264 | 11/2007 |
| WO | 2011060126 | 5/2011 |
| WO | 2012151382 | 11/2012 |
| WO | 2014015184 | 1/2014 |
| WO | 2014020187 | 2/2014 |
| WO | 2014074769 | 5/2014 |
| WO | 2017132204 | 8/2017 |

OTHER PUBLICATIONS

Megharaj Mallavarpu; Healthy Levels of Soil Algae Lift Plant Growth; Fertility; Farming Ahead No. 120—Dec. 2001. p. 1.‡
Huang et al. Harvesting of *Chlorella* sp. using hollow fiber ultrafiltration. Springer 2012; 1-6.‡
International Search Report and Written Opinion for PCT/US2015/066160, dated Feb. 23, 2016.‡
IFA, Fertilizers and Agriculture Quarterly Newsletter, May 2013, 12 pages.‡
Strawberries for Quality and Production, Nov. 22, 2014 17 pages
Holden Testing Report, "Evaluating Heliae Technology as a soil applied treatment in Tomatoes for Quality and Production," Nov. 10, 2014, 16 pages.‡
Holden Testing Report, "Evaluating Heliae Technology as a soil drench treatment in a Nursery Environment for Early Plant Growth," Nov. 9, 2014, 23 pages.‡
Holden Testing Report, "Evaluating Heliae Technology in a Nursery Environment for Plant Germination," Nov. 9, 2014, 27 pages.‡
Sanger. Freezing and thawing cultured cells. Sanger. 2001 ; 1-2.‡
Sears, "Production and Application of an Aircraft Spreadable, Cyanobacterial Based Biological Soil Crust Inoculant for Soil Fertilization, Soil Stabilization and Atmospheric CO2 Drawdown and Sequestration," US Statutory Invention Registration Jul. 3, 2012 US00H002271 H.‡
Shaaban, et al., "Green Microalgae Water Extract and Micronutrients Foliar Application as Promoters to Nutrient Balance and Growth of Wheat Plants," J. of American Science 2010, 6(9), pp. 631-636.‡
Shah, et al., "Seaweed Sap as an Alternative Liquid Fertilizer for Yield and Quality Improvement of Wheat," J.Plant Nutrition, 36, 2013, pp. 192-200.‡
Shakhashiri; Chemical of the Week, General Chemistry; www.scifun.org.‡
Steve. Chile pepper seed germination and growing tips. ushotstuff.com 2011 ;1-8.‡
Zodape, et al., "Effect of Kappaphycus alvarezii (Doty) Doty ex silva. extract on grain quality, yield and some yield components of wheat (*Triticum aestivum* L.)," International J. of Plant Production 3 (2) Apr. 2009, pp. 97-102.‡
Heeg, Jaqueline S. and Wolf, Matthias, ITS2 and 18S rDNA sequence-structure phylogeny of Chlorella and allies (Chlorophyta, Trebouxiophyceae, Chlorellaceae); Plant Gene 4 (2015) 20-28.‡
HiMedia. Chlorella broth. HiMedia. 2011; 102.‡
Prasad, et al., "Detection and Quantification of some Plant Growth regulators in a seaweed-based foliar spray employing a mass spectrometric technique sans chromatographic separation," J. of Agricultural and Food Chemistry, 2010, 58, pp. 4594-4601.‡
Holden Testing Report, "Evaluating Heliae Technology as a foliar applied treatment in Bell Peppers for Quality and Production," Nov. 22, 2014 20 pages.‡
Rathore, et al., "Effect of Seaweed Extract on the Growth, Yield and Nutrient Uptake of Soybean (*Glycine max*) Under Rainfed Conditions," South African J. of Botany, 75,2009, pp. 351-355.‡
Rehm, "Use of Banded Fertilizer for Corn Production," 2002, retrieved from http://www.extension.umn.edu/distribution/ cropsystems/DC7425.html on Apr. 15, 2013, 9 pages.‡
Germond et al., The phylogenetic position and phenotypic changes of a Chlorella-like alga during 5-year microcosm culture; Eur. J Phycol. (2013), 48(4):485-496.‡
Moniem, et al., "Effect of Green Alga Cells Extract as Foliar Spray on Vegetative Growth, Yield and Berries Quality of Superior Grapevines," American-Eurasian J. Agric. & Environ. Sci., 4 (4), 2008, pp. 427-434.‡
Harper Kimball et al, 'Cyanobacteria and cyanolichens: Can they enhance availability of essential minerals for higher plants?' Great Basin Naturalist, vol. 53, No. 1, 1993, pp. 59-72.‡
Moore, et al., "Novel Cytotoxins and Fungicides from Blue-Green-Algae and Marine Animals Possessing Algal Symbionts," Pure & Appl. Chem., v 61, n 3, 1989, pp. 521-524.‡

(56) References Cited

OTHER PUBLICATIONS

Karin L. Hastings et al., Effect of microalgae application on soil algal species diversity, cation exchange capacity and organic matter after herbicide treatments; (version 1; referees: 1 approved, 1 not approved]; Integrated Life Sciences Research Complex at Global Organics, Goodyear, AZ, 85338, USA. First Published: Nov. 14, 2014, 3:281, Latest published: Nov. 14, 2014, 3:281. pp. 1-19.‡

Nikolov et al., In Vitro Antifungal Examination of Potassium Sorbate Towards Some Phytopathogens; Bulgarian Journal of Agricultural Sicence, 17 (No. 2) 2011, 191-194 Agricultural Academy.‡

Holden Testing Report, "Evaluating Heliae Technology as a foliar treatment in a Wine Grape Vineyard for Quality and Production," Nov. 22, 2014, 16 pages.‡

Holden Testing Report, "Evaluating Heliae Technology as a soil applied treatment in a Wine Grape Vineyard for Quality and Production," Nov. 22, 2014, 17 pages.‡

Childress C. Seed Soaking/presprouting tips & ideas! part 1. Green Been Connection. 2011; 1-7.‡

Holden Testing Report, "Evaluating Heliae Technology as a soil applied treatment in Bell Peppers for Quality and Productions," Nov. 22, 2014 23 pages.‡

Choleva, et al., "Preliminary study of the green algae chlorells (*Chiarella vulgaris*) for control on the root-knot nematode (*Meloidogyne arenaria*) in tomato plants and ectoparasite *Xiphinema indexin* grape seedlings," Commun Agric Appl Biol Sci, v 70, n 4, 2005 pp. 915-927.‡

Holden Testing Report, "Evaluating Heliae Technology as a soil applied treatment in Strawberries for Quality and Production," Nov. 22, 2014 17 pages.‡

Dasgan, et al., "Use of Some Microorganisms as Bio-Fertilizers in Soilless Grown Squash for Saving Chemical Nutrients," Acta Horticulturae, Issue 927, 2010 pp. 155-162.‡

Holden Testing Report, "Evaluating Heliae Technology as a foliar applied treatment in Strawberries for Quality and Production," Nov. 22, 2014, 20 pages.‡

Dubey, et al., "Evaluation of Cost Effective Organic Fertilizers," Research & Development Centre, Kilpest India Ltd., Govingpura, Bhopal, 7 pages.‡

Holden Testing Report, "Evaluating Heliae Technology as a foliar applied treatment in Tomatoes for Quality and Production," Nov. 22, 2014, 17 pages.‡

Faheed et al. Effect of Chlorella vulgaris as bio-fertilizer on growth parameters and metabolic aspects of lettuce plant. J. Agri.Soc. Sci. 2008;4(4):165-69.‡

Flynn, "Production and Deployment of Photosynthetic Nitrogen-fixing Biofertilizers," International Erosion Control Association—Proceedings of Conference 37, 2006, pp. 69-78.‡

Aono, et al., "Effect of foliar application of fertilizer on the growth and quality of new shoot of tea plant," Chagyo Gijutsu Kenkyu 1982, 63, pp. 23-32.‡

Babu, et al., "Effect of Kappaphycus alvarezii SLF treatment on Seed germination, Growth and Development of seedling in some Crop plants," J. Acad. Indus. Res. vol. 1 (4) Sep. 2012, 10, pp. 186-195.‡

BioFlora, GOgreen Label.‡

Abo El-Baky, et al., "Enhancing antioxidant availability in wheat grains from plants grown under seawater stress in response to microalgae extract treatments," J. Science Food Agriculture 90, 2010, pp. 299-303.‡

Agroplasma Inc., Ferticell Product Catalog, Http://agroplasmausa.com/productcatalog, accessed Oct. 28, 2013, 18 pages.‡

Andrews, 'Quantifying the Fertilizer Value of Algal Meal: An Evaluation of an Integrated Dairy-Anaerobic Digester-Algae Production Facility,' A Thesis submitted to Oregon State University in partial fulfillment of the requirements for the degree of Master of Science, May 10, 2013, 132 pages.‡

Holden Testing Report, "Evaluating Heliae Technology as a foliar treatment in a Nursery Environment for Early Plant Growth," Nov. 9, 2014, 23 pages.‡

Nakao et al., : Japanese Journal of Soil Science and Plant Nutrition (1994), vol. 65, No. 6, pp. 670-676 (Year: 1994).‡

Sellers, et al., Abstract—56, "The Narrow Balance of Feeding Charged Nutrients", Recent Advances in Fermentation Technolog (RAFT) conference outline, Conference date Oct. 28, 2017 (online).

International Search Report for PCT/US2018/060026 dated Mar. 4, 2019.

Agroplasma Inc., Ferticeil Product Catalog, Http://agroplasmausa.com/product-catalog, accessed Oct. 28, 2013, 18 pages.

Choleva, et al., "Preliminary study of the green algae chlorells (*Chlorella vulgaris*) for control on the root-knot nematode (*Meloidogyne arenaria*) in tomato plants and ectoparasite *Xiphinema indexin* grape seedlings," Commun Agric Appl Biol Sci, v 70, n 4, 2005 pp. 915-927.

Faheed et al., "Effect of Chlorella Vulgaris as Bio-fertilizer on Growth Parameters and Metabolic Aspects of Lettuce Plant," Journal of Agriculture & Social Sciences, vol. 4, No. 4, 2008, pp. 165-169.

Germond, et al "The phylogentic position and phenotypic changes of a Chlorella-like alga during 5-year microcosm culture", Eur. J. Phycol (2013), 46(4): 485-496.

Karin L Hastings, et al., "Effect of rnicroalgae application on soil algal species diversity, cation exchange capacity and organic matter after herbicide treatments"; (version 1; referees; 1 approved, 1 not approved); Integrated Life Sciences Research Complex at Global Organics, Goodyear, AZ 85338, USA, First Published; Nov. 14, 2014, 3:281, Latest published: Nov. 14, 2014, 3:281. pp. 1-19.

Heeg, et al ITS2 and 18S rDNA sequence-structure phylogeny of Chlorella and allies (Chlorophyta, Trebouxiophyceae, Chlorellaceae) Plant Gene 4 (2015) 20-28.

Holden Testing Report, "Evaluating Heliae Technology as a soil applied treatment in Tomatoes for Quality and Production," Nov. 10, 2014, 16 pages.

Jha, et al., "Efficacy of new Inexpensive Cyanobacterial Biofertilizer including its Shelf Life," World J. of Microbiology and Biotechnology, v22 n1, 2006, pp. 73-79.

Leonian, "Effect of Auxins from Some Green Algae upon Phytophthora Cactorurn," Botanical Gazette, v 97, n 4, Jun. 1936, pp. 854-859.

Megharaj Mallavarpu; "Healthy Levels of Soil Algae Lift Plant Growth", Farming Ahead No. 120—Dec. 2001, p. 1.

Moniem, et al., "Effect of Green Alga Cells Extract as Foliar Spray on Vegetative Growth, Yield and Berries Quality of Superior Grapevines," American-Eurasian J. Agric. & Environ. Sci., 4 (4), 2008, pp. 427-433.

Nikolov, et al. In vitro antifungal examination of potassium sorbate towards some phytopathogens. Bulgarian Journal of Agricultural Science. 2011;17(2): 191-194.

Sears, "Production and Application of an Aircraft Spreadable, Cyanobacterial Based Biological Soil Crust Inoculant for Soil Fertilization, Soil Stabilization and Atmospheric CO2 Drawdown and Sequestration," US Statutory Invention Registration Jul. 3, 2012 US00H002271H.

Zodape, et al, "Effect of Kappaphycus alvarezli (Doty) Doty ex silva. extract on grain quality, yield and some yield components of wheat (*Triticum aestivum* L)," International J. of Plant Production 3 (2) Apr. 2009, pp. 97-102.

Zodape, et al., "Effect of liquid seaweed fertilizer on yield and quality of okra (*Abelmoschus esculentus* L.)," J of Scientific & Industrial Research, v 67, Dec. 2008, pp. 1115-1117.

Zodape, et al., "Enhanced yield and nutritional quality in green gram (*Phaseolus radiata* L) treated with seaweed (*Kappaphycus alvarezii*) extract," J. of Scientific & Industrial Research, v 69, Jun. 2010, pp. 468-471.

Zodape, et al., "Foliar application of seaweed sap as biostimulant for enhancement of yield and quality of tomato (*Lycopersicon esculentum* Mill.)," J. of Scientific and Industrial Research, v 70, Mar. 2011, pp. 215-219.

\* cited by examiner
‡ imported from a related application

| Treatment | Rate (gal/A) | % Marketable due to bruising level | % Advantage over Standard Practice | % Advantage over Comm. Ref. | % severe+mode rate bruising level | % Advantage over Standard Practice | % Advantage over Comm. Ref. | Hedonics Liking scores (9pt scale) Overall | Appearance | Aroma | Flavor | Texture |
|---|---|---|---|---|---|---|---|---|---|---|---|---|
| Standard practice | | 73.9% | | | 21.0% | | | | | | | |
| Comm. Ref. | 0.5 | 95.8% | 30% | | 0.0% | | | | | | | |
| PhycoTerra | 0.4 | 88.6% | 20% | -8% | 10.0% | -52% | | | | | | |
| PhycoTerra | 0.5 | 95.2% | 29% | -1% | 5.0% | -76% | | | | | | |
| PhycoTerra | 1 | 90.1% | 22% | -6% | 2.5% | -88% | | | | | | |
| PhycoTerra | 2 | 96.0% | 30% | 0% | 4.0% | -81% | | | | | | |
| HS399 EB | 0.4 | 92.3% | 25% | -4% | 0.0% | -100% | | | | | | |
| HS399 EB | 0.5 | 97.0% | 31% | 1% | 1.3% | -94% | | | | | | |
| HS399 EB | 1 | 96.0% | 30% | 0% | 2.8% | -87% | | | | | | |
| HS399 EB | 2 | 91.5% | 24% | -4% | 4.3% | -80% | | | | | | |
| GWP | 0.4 | 97.6% | 32% | 2% | 2.5% | -88% | | | | | | |
| GWP | 0.5 | 100.0% | 35% | 4% | 0.0% | -100% | | | | | | |
| GWP | 1 | 94.4% | 28% | -1% | 3.0% | -86% | | | | | | |
| GWP | 2 | 94.6% | 28% | -1% | 0.0% | -100% | | | | | | |
| Standard practice | | 26.4% | | | 65.5% | | | 5.6 | 4.8 | 5.9 | 5.4 | 5.5 |
| Comm. Ref. | 0.5 | 26.5% | 0% | | 73.5% | 12% | | 5.8 | 6.1 | 6.2 | 5.6 | 6.3 |
| PhycoTerra | 0.4 | 43.7% | 66% | 65% | 56.5% | -14% | -23% | | | | | |
| PhycoTerra | 0.5 | 52.4% | 98% | 98% | 47.5% | -27% | -35% | 6.0 | 5.6 | 6.4 | 6.0 | 6.2 |
| PhycoTerra | 1 | 41.9% | 59% | 58% | 58.0% | -11% | -21% | | | | | |
| PhycoTerra | 2 | 30.6% | 16% | 15% | 69.5% | 6% | -5% | | | | | |
| HS399 EB | 0.4 | 57.1% | 116% | 115% | 57.3% | -13% | -22% | | | | | |
| HS399 EB | 0.5 | 54.1% | 105% | 104% | 46.0% | -30% | -37% | 5.6 | 5.6 | 6.1 | 5.8 | 5.7 |
| HS399 EB | 1 | 41.5% | 57% | 57% | 58.5% | -11% | -20% | | | | | |
| HS399 EB | 2 | 51.5% | 95% | 94% | 48.3% | -26% | -34% | | | | | |
| GWP | 0.4 | 45.5% | 72% | 72% | 54.5% | -17% | -26% | | | | | |
| GWP | 0.5 | 24.4% | -8% | -8% | 75.8% | 16% | 3% | 6.0 | 5.8 | 6.0 | 5.7 | 5.9 |
| GWP | 1 | 27.2% | 3% | 3% | 72.8% | 11% | -1% | | | | | |
| GWP | 2 | 22.4% | -15% | -15% | 77.5% | 18% | 5% | | | | | |

FIG. 1

| Treatment | Rate (gal/A) | 1st pick | % Advantage over Standard Practice | % Advantage over Comm. Ref. | 2nd pick | % Advantage over Standard Practice | % Advantage over Comm. Ref. | 3rd pick | % Advantage over Standard Practice | % Advantage over Comm. Ref. | 4th pick | % Advantage over Standard Practice | % Advantage over Comm. Ref. |
|---|---|---|---|---|---|---|---|---|---|---|---|---|---|
| Standard practice | | 9.7 | | | 11.3 | | | 11.9 | | | 11.6 | | |
| Commercial reference | 0.5 | 9.6 | -1% | | 11.0 | -2% | | 12.1 | 2% | | 12.0 | 4% | |
| PhycoTerra | 0.25 | 9.2 | -5% | -4% | 11.1 | -2% | 0% | 11.7 | -2% | -3% | 12.2 | 5% | 1% |
| PhycoTerra | 0.5 | 9.1 | -7% | -5% | 11.2 | -1% | 2% | 11.2 | -6% | -7% | 12.4 | 7% | 3% |
| Terrene 65 | 0.25 | 10.1 | 4% | 6% | 11.3 | 0% | 2% | 11.2 | -6% | -7% | 12.0 | 3% | 0% |
| Terrene 65 | 0.5 | 10.1 | 4% | 6% | 11.5 | 2% | 4% | 11.5 | -4% | -5% | 12.7 | 10% | 6% |
| HS399 EB | 0.25 | 9.5 | -2% | -1% | 10.7 | -5% | -3% | 11.8 | -1% | -2% | 13.0 | 12% | 8% |
| HS399 EB | 0.5 | 9.4 | -3% | -1% | 10.5 | -7% | -5% | 11.7 | -2% | -3% | 11.3 | -2% | -6% |
| HS399 WB | 0.25 | 9.8 | 1% | 2% | 10.6 | -6% | -4% | 11.6 | -2% | -4% | 11.8 | 2% | -2% |
| HS399 WB | 0.5 | 9.2 | -5% | -4% | 11.2 | -1% | 2% | 12.0 | 1% | -1% | 11.6 | 1% | -3% |
| Combo 399EB | 0.25 | 9.4 | -3% | -2% | 11.2 | -1% | 1% | 12.8 | 8% | 6% | 13.1 | 13% | 9% |
| Combo 399EB | 0.5 | 9.4 | -3% | -1% | 10.6 | -6% | -4% | 11.0 | -8% | -9% | 11.6 | 0% | -4% |
| Combo 399WB | 0.25 | 9.5 | -2% | -1% | 11.1 | -2% | 1% | 12.0 | 1% | -1% | 12.1 | 4% | 1% |
| Combo 399WB | 0.5 | 10.0 | 3% | 4% | 11.4 | 1% | 3% | 12.0 | 1% | -1% | 11.6 | 0% | -3% |
| Greenwater polyculture | 0.25 | 9.2 | -5% | -4% | 11.4 | 1% | 3% | 11.7 | -1% | -3% | 12.6 | 9% | 5% |
| Greenwater polyculture | 0.5 | 9.2 | -5% | -4% | 11.5 | 2% | 4% | 11.5 | -3% | -5% | 11.9 | 3% | -1% |

FIG. 6

BIOMASS COMPOSITIONS AND METHODS FOR MAKING THE SAME

CROSS REFERENCE TO RELATED APPLICATIONS

This application is a divisional of U.S. application Ser. No. 16/185,652 titled BIOMASS COMPOSITIONS, filed on Nov. 9, 2018 in the name of Applicant. U.S. application Ser. No. 16/185,652 in turn claims the benefit of U.S. Provisional Application No. 62/584,311, filed Nov. 10, 2017, titled BIOMASS COMPOSITIONS; U.S. Provisional Application No. 62/642,729, filed Mar. 14, 2018, titled BIOMASS FOR INCREASING ROOT AND SHOOT YIELD IN LETTUCE; and U.S. Provisional Application 62/680,373, filed Jun. 4, 2018, titled BIOMASS COMPOSITIONS. The entire contents of each of the foregoing are hereby incorporated in full by reference.

FIELD OF THE INVENTION

The present invention generally relates to agriculture and, more specifically, to biomass compositions for decreasing bruising, increasing plant health, increasing soil health, increasing sweetness in fruits, improving shelf life, increasing fruit water retention, and/or decreasing needle-drop in conifer species and methods for making the same.

BACKGROUND OF THE INVENTION

The growth of a plant is a complex physiological process involving inputs and pathways in the roots, shoots, and leaves. Whether at a commercial or home garden scale, growers are constantly striving to optimize the yield and quality of plants.

SUMMARY OF THE INVENTION

This Summary is provided to introduce a selection of concepts in a simplified form that are further described below in the Detailed Description. This Summary is not intended to identify key factors or essential features of the claimed subject matter, nor is it intended to be used to limit the scope of the claimed subject matter.

Some embodiments of the invention relate to a method of enhancing a plant comprising the step of administering to the plant, seedling, or seed a liquid composition treatment including a culture of microalgae. The microalgae can include at least one of pasteurized *Chlorella* cells and pasteurized *Aurantiochytrium acetophilum* HS399 cells in an amount effective to enhance at least one characteristic of a plant compared to a substantially identical untreated plant. The characteristic can be enhanced fruit sweetness, enhanced fruit resistance to bruising, and/or diminished needle-drop. "Substantially identical" refers to being the same as is practicable under the circumstances of a given test, as that a person of ordinary skill in the art would consider any actual differences to be insignificant in evaluating the validity of experimental results. As understood in the art, in real-world biological experiments these kinds of comparisons are always necessary and are accepted by those of ordinary skill in the art in view of the fact that there are no practical alternatives except often impractically large data sets and sample sizes.

In some embodiments, the method can include contacting soil in the immediate vicinity of the plant, seedling, or seed with an effective amount of the liquid composition treatment. In some embodiments, the liquid composition can be administered at a rate in the range of 0.25-2 gallons/acre. In some embodiments, the liquid composition can include between 100 g-800 g per acre of at least one of pasteurized *Chlorella* cells and pasteurized *Aurantiochytrium acetophilum* HS399 cells. The *Aurantiochytrium acetophilum* HS399 strain was deposited on Sep. 12, 2019 at National Center for Marine Algae and Microbiota (NCMA), located at 60 Bigelow Drive, East Boothbay, Me. 04544, USA and received accession number 201909001, which is sufficient to specifically identify the deposited biological material and to permit examination.

In some embodiments, the contacting step can include a drip irrigation system and/or process.

In some embodiments, the liquid composition treatment can further include phosphoric acid and potassium sorbate. In some embodiments, the liquid composition treatment can further include citric acid.

In some embodiments, the pasteurized *Chlorella* cells are pasteurized at a temperature in the range of 65° C.-90° C. and the pasteurized *Aurantiochytrium acetophilum* HS399 cells are pasteurized at a temperature in the range of 65° C.-75° C.

In some embodiments, the pasteurized *Chlorella* cells and pasteurized *Aurantiochytrium acetophilum* HS399 cells are pasteurized for between 90-150 minutes.

In some embodiments, the microalgae includes only *Chlorella* cells, only *Aurantiochytrium* cells, or *Chlorella* cells and *Aurantiochytrium acetophilum* HS399 cells and the liquid composition is applied in an effective amount to enhance sweetness of the fruit of the plant by at least 5% compared to fruit of a substantially identical untreated plant. For example, the sweetness can be enhanced by about 5%, 7%, 10%, 15%, or 20%.

In some embodiments, the microalgae includes only *Chlorella* cells, only *Aurantiochytrium* cells, or *Chlorella* cells and *Aurantiochytrium acetophilum* HS399 cells and the liquid composition is applied in an amount effective to enhance resistance to bruising of the fruit of the plant by at least 5% compared to fruit of a substantially identical untreated plant. For example, the resistance to bruising can be enhanced by about 5%, 7%, 10%, 15%, or 20%.

In some embodiments, the microalgae includes only *Chlorella* cells, only *Aurantiochytrium* cells, or *Chlorella* cells and *Aurantiochytrium acetophilum* HS399 cells in an amount effective to reduce needle-drop of the plant by at least 5% compared to a substantially identical untreated plant. For example, the needle-drop can be reduced by about 5%, 7%, 10%, 15%, or 20%.

In some embodiments, the liquid composition can include pasteurized *Chlorella* cells and pasteurized *Aurantiochytrium acetophilum* HS399 cells in a ratio of 25:75.

In some embodiments, the *Aurantiochytrium acetophilum* HS399 cells have been subjected to an extraction process to remove oils from the *Aurantiochytrium acetophilum* HS399 cells.

Some embodiments of the invention can relate to a composition for enhancing at least one plant characteristic. The composition can include a microalgae biomass comprising at least two species of microalgae. The composition can cause synergistic enhancement of at least one plant characteristic. The characteristic can be enhanced fruit sweetness, enhanced fruit resistance to bruising, and diminished needle-drop.

In some embodiments, the microalgae species can be selected from *Botryococcus, Chlorella, Chlamydomonas, Scenedesmus, Pavlova, Phaeodactylum, Nannochloropsis,*

*Aurantiochytrium, Spirulina, Galdieria, Haematococcus, Isochrysis, Porphyridium, Schizochytrium, Tetraselmi,* and/or the like.

In some embodiments, the microalgae biomass can include whole biomass and/or residual biomass.

In some embodiments, the composition can include a first species of microalgae and a second species of microalgae. In some embodiments, the ratio of the first species of microalgae and the second species of microalgae is between 1:20 and 1:1. In some embodiments, the ratio of the first species of microalgae and the second species of microalgae is between 1:4 and 1:1.

In some embodiments, the first species of microalgae is *Chlorella* and the second species of microalgae is *Aurantiochytrium*. In some embodiments, the ratio of *Chlorella* and *Aurantiochytrium* is 25:75, 50:50 or 75:25.

In some embodiments, the *Chlorella* can be whole biomass and *Aurantiochytrium* is residual biomass or the *Chlorella* can be residual biomass and *Aurantiochytrium* is whole biomass.

Some embodiments of the invention relate to a method of plant enhancement that can include administering to a plant, seedling, or seed a composition treatment. The composition treatment can enhance at least one plant characteristic synergistically. The characteristic can be enhanced fruit sweetness, enhanced fruit resistance to bruising, and diminished needle-drop.

Embodiments of the invention relate to a composition for enhancing at least one plant characteristic. The composition can include a microalgae biomass that includes at least one species of microalgae. The composition can include a microalgae biomass that includes at least two species of microalgae. The composition can cause synergistic enhancement of at least one plant characteristic.

In some embodiments, the microalgae species can include *Chlorella, Schizochytrium, Thraustochytrium, Oblongichytrium* and/or species and/or strains of *Aurantiochytrium*, such as, for example, *A. acetophilum* HS399. In other embodiments, the microalgae species can include *Botryococcus, Chlamydomonas, Scenedesmus, Pavlova, Phaeodactylum, Nannochloropsis, Spirlulina, Galdieria, Haematococcus, Isochrysis, Porphyridium, Tetraselmis,* and/or the like.

In some embodiments, the microalgae biomass can include whole biomass and/or residual biomass. Whole biomass includes substantially all components and fractions of the cells from which the whole biomass is derived. Residual or extracted biomass can be any remaining biomass after extraction and/or removal of one or more components of a whole biomass.

In some embodiments, the composition can include one species of microalgae. In some embodiments, the composition can include a first species of microalgae and a second species of microalgae. The ratio of the first species of microalgae and the second species of microalgae can be between about 25:75, 50:50, or 75:25.

In some embodiments, the first species of microalgae may be *Chlorella* and the second species of microalgae may be *Aurantiochytrium acetophilum* HS399. In some embodiments, the ratio of *Chlorella* and *Aurantiochytrium acetophilum* HS399 may range between about 25:75 to 75:25. For example, the ratio of *Chlorella* and *Aurantiochytrium acetophilum* HS399 may be about 25:75, 50:50, or 75:25. In some embodiments, the *Chlorella* is whole biomass and *Aurantiochytrium acetophilum* HS399 is residual/extracted biomass. In some embodiments, the *Aurantiochytrium acetophilum* HS399 is whole biomass and *Chlorella* is residual/extracted biomass. In some embodiments, the *Chlorella* and *Aurantiochytrium acetophilum* HS399 are both whole biomass and in other embodiments the *Chlorella* and *Aurantiochytrium acetophilum* HS399 are both residual/extracted biomass.

Some embodiments of the invention relate to a method of plant enhancement comprising administering to a plant, seedling, seed, or soil the composition treatment, wherein the composition treatment enhances at least one plant characteristic. In some embodiments, the composition is applied when the plant is under salt stress conditions, temperature stress conditions, and/or the like.

Embodiments of the invention relate to a method of plant enhancement comprising administering a composition treatment comprising at least one microalgae species to soil. The administering can be by soil drench at the time of seeding. The method can include growing the plant to a transplant stage. The method can include transferring the plant at the transplant stage from an initial container to a larger container or a field, or the like. In some embodiments the plant at the transplant stage has at least one enhanced plant characteristic. The enhanced plant characteristic can be improved root density, improved root area, enhanced plant vigor, enhanced plant growth rate, enhanced plant maturation, and/or enhanced shoot development. After the transfer, the plant may have at least one enhanced plant characteristic. The composition treatment can include at least one microalgae species such as *Botryococcus, Chlorella, Chlamydomonas, Scenedesmus, Pavlova, Phaeodactylum, Nannochloropsis, Aurantiochytrium, Spirlulina, Galdieria, Haematococcus, Isochrysis, Porphyridium, Schizochytrium, Tetraselmis,* and/or the like. In some of the embodiments and Examples below, the microalgae composition may be applied to the soil of the fruiting plant by drenching the soil initially at the time of transplant and then subsequently every two weeks (once every 14 days) after transplant until harvest.

Decreasing Bruising

In one embodiment of the present invention, a method of decreasing bruising of fruit of a fruiting plant is disclosed. The method comprises the step of administering to the fruiting plant, seedling, or seed a liquid composition treatment comprising a culture of microalgae, the microalgae comprising at least one of pasteurized *Chlorella* cells and pasteurized *Aurantiochytrium acetophilum* HS399 cells in an amount effective to decrease bruising in the fruit of a population of such fruiting plants compared to a substantially identical population of untreated fruiting plants.

In another embodiment of the present invention, a method of decreasing bruising of fruit of a fruiting plant is disclosed. The method comprises the step of administering to the fruiting plant, seedling, or seed a liquid composition treatment comprising a culture of microalgae, the microalgae comprising at least one of pasteurized *Chlorella* cells and pasteurized *Aurantiochytrium acetophilum* HS399 cells in an effective amount to decrease bruising in the fruit of a population of fruiting plants by 2-100% compared to fruit of a substantially identical population of untreated fruiting plants, wherein administering comprising contacting soil in the immediate vicinity of the fruiting plant, seedling, or seed with an effective amount of the liquid composition treatment by drip irrigation.

In another embodiment of the present invention, a method of decreasing bruising of fruit of a fruiting plant is disclosed. The method comprises the steps of: providing a liquid composition treatment comprising a culture of microalgae, the microalgae comprising at least one of pasteurized *Chlorella* cells and pasteurized *Aurantiochytrium acetophilum*

HS399 cells; diluting the liquid composition treatment to contain between 100 g-800 g per acre of the at least one of pasteurized *Chlorella* cells and pasteurized *Aurantiochytrium acetophilum* HS399 cells; and administering the liquid composition treatment to a fruiting plant, seedling, or seed in an effective amount to decrease bruising in the fruit of a population of such fruiting plants compared to a substantially identical population of untreated fruiting plants.

Increasing Sweetness

In one embodiment of the present invention, a method of increasing sweetness of fruit of a fruiting plant is disclosed. The method comprises the step of administering to the fruiting plant a liquid composition treatment comprising a culture of microalgae, the microalgae comprising at least one of pasteurized *Chlorella* cells and pasteurized *Aurantiochytrium acetophilum* HS399 cells in an effective amount to increase total dissolved sugars in the fruit of a population of such fruiting plants compared to a substantially identical population of untreated fruiting plants.

In another embodiment of the present invention, a method of increasing sweetness of fruit of a fruiting plant is disclosed. The method comprises the step of administering to the fruiting plant, seedling, seed a liquid composition treatment comprising a culture of microalgae, the microalgae comprising at least one of pasteurized *Chlorella* cells and pasteurized *Aurantiochytrium acetophilum* HS399 cells in an effective amount to increase total dissolved sugars in the fruit of a population of such fruiting plants by 2-32% compared to fruit of a substantially identical population of untreated fruiting plants, wherein administering comprises contacting soil in the immediate vicinity of the fruiting plant, seedling, or seed with an effective amount of the liquid composition treatment by drip irrigation.

In another embodiment of the present invention, a method of increasing sweetness of fruit of a fruiting plant is disclosed. The method comprises the steps of: providing a liquid composition treatment comprising a culture of microalgae, the microalgae comprising at least one of pasteurized *Chlorella* cells and pasteurized *Aurantiochytrium acetophilum* HS399 cells; diluting the liquid composition treatment to contain between 0.95 g-15 g per gallon of the at least one of pasteurized *Chlorella* cells and *Aurantiochytrium acetophilum* HS399 cells; and administering the liquid composition treatment to a fruiting plant, seedling, or seed, in an effective amount to increase total dissolved sugars in the fruit of a population of such fruiting plants compared to a substantially identical population of untreated fruiting plants.

To the accomplishment of the foregoing and related ends, the following description and annexed drawings set forth certain illustrative aspects and implementations. These are indicative of but a few of the various ways in which one or more aspects may be employed. Other aspects, advantages and novel features of the disclosure will become apparent from the following detailed description when considered in conjunction with the annexed drawings.

BRIEF DESCRIPTION OF THE DRAWINGS

The present application is further detailed with respect to the following drawings. These figures are not intended to limit the scope of the present application, but rather, illustrate certain attributes thereof.

FIG. 1 is a table showing the effects of a microalgae composition on strawberry quality after storage, wherein the effects are observed in a decrease in bruising and increases in appearance, aroma, flavor, and texture relative to the (untreated control);

FIG. 6 is a table showing a comparison of the effects of several microalgae compositions on strawberry quality, wherein the effects are observed in an increase in strawberry sweetness (% brix) relative to the UTC and a seaweed commercial reference product;

DETAILED DESCRIPTION OF THE INVENTION

Figure 2:
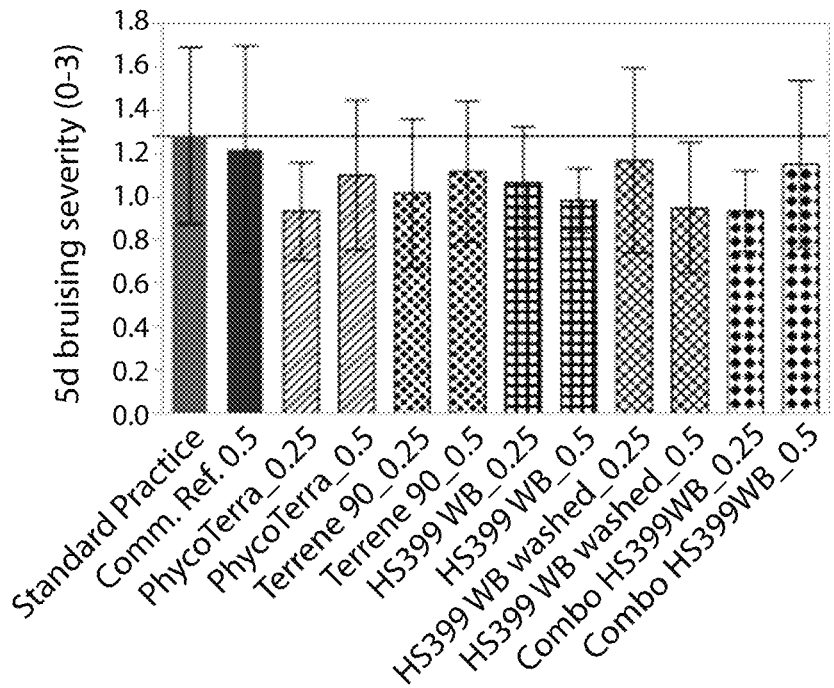
FIG. 2 is a graph showing a comparison of the effects of the several microalgae compositions of FIG. 1 on strawberry growth, yield, and post-harvest quality, wherein the effects are observed in a decrease in bruising of the strawberries after 5 days relative to the UTC and a seaweed commercial reference product.

The description set forth below in connection with the appended drawings is intended as a description of presently preferred embodiments of the disclosure and is not intended to represent the only forms in which the present disclosure may be constructed and/or utilized. The description sets forth the functions and the sequence of steps for constructing and operating the disclosure in connection with the illustrated embodiments. It is to be understood, however, that the same or equivalent functions and sequences may be accomplished by different embodiments that are also intended to be encompassed within the spirit and scope of this disclosure.

Many plants can benefit from the application of liquid compositions that provide a bio-stimulatory effect. Non-limiting examples of plant families that can benefit from such compositions include plants from the following: Solanaceae, Fabaceae (Leguminosae), Poaceae, Roasaceae, Vitaceae, Brassicaeae (Cruciferae), Caricaceae, Malvaceae, Sapindaceae, Anacardiaceae, Rutaceae, Moraceae, Convolvulaceae, Lamiaceae, Verbenaceae, Pedaliaceae, Asteraceae (Compositae), Apiaceae (Umbelliferae), Araliaceae, Oleaceae, Ericaceae, Actinidaceae, Cactaceae, Chenopodiaceae, Polygonaceae, Theaceae, Lecythidaceae, Rubiaceae, Papveraceae, Illiciaceae Grossulariaceae, Myrtaceae, Juglandaceae, Bertulaceae, Cucurbitaceae, Asparagaceae (Liliaceae), Alliaceae (Liliceae), Bromeliaceae, Zingieraceae, Muscaceae, Areaceae, Dioscoreaceae, Myristicaceae, Annonaceae, Euphorbiaceae, Lauraceae, Piperaceae, Proteaceae, and Cannabaceae.

The Solanaceae plant family includes a large number of agricultural crops, medicinal plants, spices, and ornamentals in its over 2,500 species. Taxonomically classified in the Plantae kingdom, Tracheobionta (subkingdom), Spermatophyta (superdivision), Magnoliophyta (division), Manoliopsida (class), Asteridae (subclass), and Solanales (order), the Solanaceae family includes, but is not limited to, potatoes, tomatoes, eggplants, various peppers, tobacco, and petunias. Plants in the Solanaceae can be found on all the continents, excluding *Antarctica*, and thus have a widespread importance in agriculture across the globe.

The Rosaceae plant family includes flowering plants, herbs, shrubs, and trees. Taxonomically classified in the Plantae kingdom, Tracheobionta (subkingdom), Spermatophyta (superdivision), Magnoliophyta (division), Magnoliopsida (class), Rosidae (subclass), and Rosales (order), the Rosaceae family includes, but is not limited to, almond, apple, apricot, blackberry, cherry, nectarine, peach, plum, raspberry, strawberry, and quince.

The Fabaceae plant family (also known as the Leguminosae) comprises the third largest plant family with over 18,000 species, including a number of important agricultural and food plants. Taxonomically classified in the Plantae kingdom, Tracheobionta (subkingdom), Spermatophyta (superdivision), Magnoliophyta (division), Manoliopsida (class), Rosidae (subclass), and Fabales (order), the Fabaceae family includes, but is not limited to, soybeans, beans, green beans, peas, chickpeas, alfalfa, peanuts, sweet peas, carob, and liquorice. Plants in the Fabaceae family can range in size and type, including but not limited to, trees, small annual herbs, shrubs, and vines, and typically develop legumes. Plants in the Fabaceae family can be found on all the continents, excluding *Antarctica*, and thus have a widespread importance in agriculture across the globe. Besides food, plants in the Fabaceae family can be used to produce natural gums, dyes, and ornamentals.

The Poaceae plant family supplies food, building materials, and feedstock for fuel processing. Taxonomically classified in the Plantae kingdom, Tracheobionta (subkingdom), Spermatophyta (superdivision), Magnoliophyta (division), Liliopsida (class), Commelinidae (subclass), and Cyperales (order), the Poaceae family includes, but is not limited to, flowering plants, grasses, and cereal crops such as barely, corn, lemongrass, millet, oat, rye, rice, wheat, sugarcane, and sorghum. Types of turf grass found in Arizona include, but are not limited to, hybrid Bermuda grasses (e.g., 328 tifgrn, 419 tifway, tif sport).

The Vitaceae plant family includes flowering plants and vines. Taxonomically classified in the Plantae kingdom, Tracheobionta (subkingdom), Spermatophyta (superdivision), Magnoliophyta (division), Magnoliopsida (class), Rosidae (subclass), and Rhammales (order), the Vitaceae family includes, but is not limited to, grapes.

Particularly important in the production of fruit from plants is the beginning stage of growth where the plant emerges and matures into establishment. A method of treating a seed, seedling, or plant to directly improve the germination, emergence, and maturation of the plant; or to indirectly enhance the microbial soil community surrounding the seed or seedling is therefore valuable starting the plant on the path to marketable production. The standard typically used for assessing emergence is the achievement of the hypocotyl stage, where a stem is visibly protruding from the soil. The standard typically used for assessing maturation is the achievement of the cotyledon stage, where two leaves visibly form on the emerged stem. Some botanists view the beginning of maturation as starting at when the first true leaf emerges beyond the cotyledon stage, as the cotyledons are already pre-formed in the seed prior to germination. Some botanists see maturation as a long phase that proceeds until full reproductive potential has been achieved.

Important in the production of fruit from plants is the yield and quality of fruit, which can be quantified as the number, weight, color, firmness, ripeness, sweetness, moisture, degree of insect infestation, degree of disease or rot, degree of sunburn of the fruit. A method of treating a plant to directly improve the characteristics of the plant, or to indirectly enhance the chlorophyll level of the plant for photosynthetic capabilities and health of the plant's leaves, roots, and shoot to enable robust production of fruit is therefore valuable in increasing the efficiency of marketable production. Marketable and unmarketable designations can apply to both the plant and fruit, and can be defined differently based on the end use of the product, such as but not limited to, fresh market produce and processing for inclusion as an ingredient in a composition. The marketable determination can assess such qualities as, but not limited to, color, insect damage, blossom end rot, softness, and sunburn. The term "total production" can incorporate both marketable and unmarketable plants and fruit. The ratio of marketable plants or fruit to unmarketable plants or fruit can be referred to as "utilization" and expressed as a percentage. The utilization can be used as an indicator of the efficiency of the agricultural process as it shows the successful production of marketable plants or fruit, which will be obtain the highest financial return for the grower, whereas total production will not provide such an indication.

To achieve such improvements in emergence, maturation, and yield of plants, a method to treat such seeds and plants, and soil with a low-concentration microalgae-based composition, in a dried or liquid solution form was developed. Microalgae can be grown in heterotrophic, mixotrophic, and phototrophic conditions. Culturing microalgae in heterotrophic conditions comprises supplying organic carbon (e.g., acetic acid, acetate, glucose) to cells in an aqueous culture medium comprising trace metals and nutrients (e.g., nitrogen, phosphorus). Culturing microalgae in mixotrophic conditions comprises supplying light and organic carbon (e.g., acetic acid, acetate, glucose) to cells in an aqueous culture medium comprising trace metals and nutrients (e.g., nitrogen, phosphorus). Culturing microalgae in phototrophic conditions comprises supplying light and inorganic carbon (e.g., carbon dioxide) to cells in an aqueous culture medium comprising trace metals and nutrients (e.g., nitrogen, phosphorus).

In some embodiments, the microalgae cells can be harvested from a culture and used as whole cells in a liquid composition for application to seeds and plants, while in other embodiments the harvested microalgae cells can be subjected to downstream processing and the resulting biomass or extract can be used in a dried composition (e.g., powder, pellet) or a liquid composition (e.g., suspension, solution) for application to plants, soil, or a combination thereof. Non-limiting examples of downstream processing comprise: drying the cells, lysing the cells, and subjecting the harvested cells to a solvent or supercritical carbon dioxide extraction process to isolate an oil or protein. In some embodiments, the extracted (i.e., residual) biomass remaining from an extraction process can be used alone or in combination with other microalgae or extracts in a liquid composition for application to plants, soil, or a combination thereof. By subjecting the microalgae to an extraction process the resulting biomass is transformed from a natural whole state to a lysed condition where the cell is missing a significant amount of the natural components, thus differentiating the extracted microalgae biomass from that which is found in nature. Excreted products from the microalgae can also be isolated from a microalgae culture using downstream processing methods.

In some embodiments, microalgae can be the predominant active ingredient source in the composition. In some embodiments, the microalgae population of the composition can include whole biomass, substantially extracted biomass, excreted products (e.g., EPS), extracted protein, or extracted oil. In some embodiments, microalgae include at least 99% of the active ingredient sources of the composition. In some embodiments, microalgae include at least 95% of the active ingredient sources of the composition. In some embodiments, microalgae include at least 90% of the active ingredient sources of the composition. In some embodiments, microalgae include at least 80% of the active ingredient sources of the composition. In some embodiments, microalgae include at least 70% of the active ingredient sources of the composition. In some embodiments, microalgae include at least 60% of the active ingredient sources of the composition. In some embodiments, microalgae include at least 50% of the active ingredient sources of the composition. In some embodiments, microalgae include at least 40% of the active ingredient sources of the composition. In some embodiments, microalgae include at least 30% of the active ingredient sources of the composition. In some embodiments, microalgae include at least 20% of the active ingredient sources of the composition. In some embodiments, microalgae include at least 10% of the active ingredient sources of the composition. In some embodiments, microalgae include at least 5% of the active ingredient sources of the composition. In some embodiments, microalgae include at least 1% of the active ingredient sources of the composition. In some embodiments, the composition lacks any detectable amount of any other active ingredient source other than microalgae.

In some embodiments, microalgae biomass, excreted products, or extracts can also be mixed with biomass or extracts from other plants, microalgae, macroalgae, seaweeds, and kelp. In some embodiments, microalgae biomass, excreted products, or extracts can also be mixed with fish oil. Non-limiting examples of other plants, macroalgae, seaweeds, and kelp fractions that can be combined with microalgae cells can include species of *Lemna, Gracilaria, Kappaphycus, Ascophyllum, Macrocystis, Fucus, Laminaria, Sargassum, Turbinaria*, and *Durvilea*. In further embodiments, the extracts can comprise, but are not limited to, liquid extract from a species of *Kappaphycus*. In some embodiments, the extracts can include 50% or less by volume of the composition. In some embodiments, the extracts can include 40% or less by volume of the composition. In some embodiments, the extracts can include 30% or less by volume of the composition. In some embodiments, the extracts can include 20% or less by volume of the composition. In some embodiments, the extracts can include 10% or less by volume of the composition. In some embodiments, the extracts can include 5% or less by volume of the composition. In some embodiments, the extracts can include 4% or less by volume of the composition. In some embodiments, the extracts can include 3% or less by volume of the composition. In some embodiments, the extracts can include 2% or less by volume of the composition. In some embodiments, the extracts can include 1% or less by volume of the composition.

The term "microalgae" refers to microscopic single cell organisms such as microalgae, cyanobacteria, algae, diatoms, dinoflagellates, freshwater organisms, marine organisms, or other similar single cell organisms capable of growth in phototrophic, mixotrophic, or heterotrophic culture conditions.

In some embodiments, microalgae biomass, excreted product, or extracts can also be sourced from multiple types of microalgae, to make a composition that is beneficial when applied to plants or soil. Non-limiting examples of microalgae that can be used in the compositions and methods of the present invention include microalgae in the classes: Eustigmatophyceae, Chlorophyceae, Prasinophyceae, Haptophyceae, Cyanidiophyceae, Prymnesiophyceae, Porphyridiophyceae, Labyrinthulomycetes, Trebouxiophyceae, Bacillariophyceae, and Cyanophyceae. The class Cyanidiophyceae includes species of *Galdieria*. The class Chlorophyceae includes species of *Haematococcus, Scenedesmus, Chlamydomonas*, and *Micractinium*. The class Prymnesiophyceae includes species of *Isochrysis* and *Pavlova*. The class Eustigmatophyceae includes species of *Nannochloropsis*. The class Porphyridiophyceae includes species of *Porphyridium*. The class Labyrinthulomycetes includes species of *Schizochytrium* and *Aurantiochytrium*. The class Prasinophyceae includes species of *Tetraselmis*. The class Trebouxiophyceae includes species of *Chlorella* and *Botryococcus*. The class Bacillariophyceae includes species of *Phaeodactylum*. The class Cyanophyceae includes species of *Spirulina*.

Non-limiting examples of microalgae genus and species that can be used in the compositions and methods of the present invention include: *Achnanthes orientalis, Agmenellum* spp., *Amphiprora hyaline, Amphora coffeiformis, Amphora coffeiformis* var. *linea, Amphora coffeiformis* var. *punctata, Amphora coffeiformis* var. *taylori, Amphora coffeiformis* var. *tenuis, Amphora delicatissima, Amphora delicatissima* var. *capitata, Amphora* sp., *Anabaena, Ankistrodesmus, Ankistrodesmus falcatus, Aurantiochytrium* sp., *Boekelovia hooglandii, Borodinella* sp., *Botryococcus braunii, Botryococcus sudeticus, Bracteococcus minor, Bracteococcus medionucleatus, Carteria, Chaetoceros gracilis, Chaetoceros muelleri, Chaetoceros muelleri* var. *subsalsum, Chaetoceros* sp., *Chlamydomonas* sp., *Chlamydomas perigranulata, Chlorella anitrata, Chlorella antarctica, Chlorella aureoviridis, Chlorella Candida, Chlorella capsulate, Chlorella desiccate, Chlorella ellipsoidea, Chlorella emersonii, Chlorella fusca, Chlorella fusca* var. *vacuolate, Chlorella glucotropha, Chlorella infusionum, Chlorella infusionum* var. *actophila, Chlorella infusionum* var. *auxenophila, Chlorella kessleri, Chlorella lobophora, Chlorella luteoviridis, Chlorella luteoviridis* var. *aureoviridis, Chlorella luteoviridis* var. *lutescens, Chlorella miniata, Chlorella minutissima, Chlorella mutabilis, Chlorella nocturna, Chlorella ovalis, Chlorella parva, Chlorella photophila, Chlorella pringsheimii, Chlorella protothecoides, Chlorella protothecoides* var. *acidicola, Chlorella regularis, Chlorella regularis* var. *minima, Chlorella regularis* var. *umbricata, Chlorella reisiglii, Chlorella saccharophila, Chlorella saccharophila* var. *ellipsoidea, Chlorella salina, Chlorella simplex, Chlorella sorokiniana, Chlorella* sp., *Chlorella sphaerica, Chlorella stigmatophora, Chlorella vanniellii, Chlorella vulgaris, Chlorella vulgaris* fo. *tertia, Chlorella vulgaris* var. *autotrophica, Chlorella vulgaris* var. *viridis, Chlorella vulgaris* var. *vulgaris, Chlorella vulgaris* var. *vulgaris* fo. *tertia, Chlorella vulgaris* var. *vulgaris* fo. *viridis, Chlorella xanthella, Chlorella zofingiensis, Chlorella trebouxioides, Chlorella vulgaris, Chlorococcum infu-*

*sionum, Chlorococcum* sp., *Chlorogonium, Chroomonas* sp., *Chrysosphaera* sp., *Cricosphaera* sp., *Crypthecodinium cohnii, Cryptomonas* sp., *Cyclotella cryptica, Cyclotella meneghiniana, Cyclotella* sp., *Dunaliella* sp., *Dunaliella bardawil, Dunaliella bioculata, Dunaliella granulate, Dunaliella maritime, Dunaliella minuta, Dunaliella parva, Dunaliella peircei, Dunaliella primolecta, Dunaliella salina, Dunaliella terricola, Dunaliella tertiolecta, Dunaliella viridis, Dunaliella tertiolecta, Eremosphaera viridis, Eremosphaera* sp., *Ellipsoidon* sp., *Euglena* spp., *Franceia* sp., *Fragilaria crotonensis, Fragilaria* sp., *Galdieria* sp., *Gloeocapsa* sp., *Gloeothamnion* sp., *Haematococcus pluvialis, Hymenomonas* sp., *Isochrysis a.ff galbana, Isochrysis galbana, Lepocinclis, Micractinium, Monoraphidium minutum, Monoraphidium* sp., *Nannochloris* sp., *Nannochloropsis salina, Nannochloropsis* sp., *Navicula acceptata, Navicula biskanterae, Navicula pseudotenelloides, Navicula pelliculosa, Navicula saprophila, Navicula* sp., *Nephrochloris* sp., *Nephroselmis* sp., *Nitschia communis, Nitzschia alexandrina, Nitzschia closterium, Nitzschia communis, Nitzschia dissipata, Nitzschia frustulum, Nitzschia hantzschiana, Nitzschia inconspicua, Nitzschia intermedia, Nitzschia microcephala, Nitzschia pusilla, Nitzschia pusilla elliptica, Nitzschia pusilla monoensis, Nitzschia quadrangular, Nitzschia* sp., *Ochromonas* sp., *Oocystis parva, Oocystis pusilla, Oocystis* sp., *Oscillatoria limnetica, Oscillatoria* sp., *Oscillatoria subbrevis, Parachlorella kessleri, Pascheria acidophila, Pavlova* sp., *Phaeodactylum tricornutum, Phagus, Phormidium, Platymonas* sp., *Pleurochrysis camerae, Pleurochrysis dentate, Pleurochrysis* sp., *Porphyridium* sp., *Prototheca wickerhamii, Prototheca stagnora, Prototheca portoricensis, Prototheca moriformis, Prototheca zopfii, Pseudochlorella aquatica, Pyramimonas* sp., *Pyrobotrys, Rhodococcus opacus, Sarcinoid chrysophyte, Scenedesmus armatus, Schizochytrium, Spirogyra, Spirulina platensis, Stichococcus* sp., *Synechococcus* sp., *Synechocystisf, Tagetes erecta, Tagetes patula, Tetraedron, Tetraselmis* sp., *Tetraselmis suecica, Thalassiosira weissflogii*, and *Viridiella fridericiana*.

Analysis of the DNA sequence of the strain of *Chlorella* sp. described in the specification was done in the NCBI 18s rDNA reference database at the Culture Collection of Algae at the University of Cologne (CCAC) showed substantial similarity (i.e., greater than 95%) with multiple known strains of *Chlorella* and *Micractinium*. Those of skill in the art will recognize that *Chlorella* and *Micractinium* appear closely related in many taxonomic classification trees for microalgae, and strains and species may be re-classified from time to time. Thus, for references throughout the instant specification for *Chlorella* sp., it is recognized that microalgae strains in related taxonomic classifications with similar characteristics to the reference *Chlorella* sp. strain would reasonably be expected to produce similar results.

Additionally, taxonomic classification has also been in flux for organisms in the genus *Schizochytrium*. Some organisms previously classified as *Schizochytrium* have been reclassified as *Aurantiochytrium, Thraustochytrium*, or *Oblongichytrium*. See Yokoyama et al. Taxonomic rearrangement of the genus *Schizochytrium* [sensu lato] based on morphology, chemotaxonomic characteristics, and 18S rRNA gene phylogeny (Thrausochytriaceae, Labyrinthulomycetes): emendation for *Schizochytrium* and erection of *Aurantiochytrium* and *Oblongichytrium* gen. nov. *Mycoscience* (2007) 48:199-211. Those of skill in the art will recognize that *Schizochytrium, Aurantiochytrium, Thraustochytrium*, and *Oblongichytrium* appear closely related in many taxonomic classification trees for microalgae, and strains and species may be re-classified from time to time. Thus, for references throughout the instant specification for *Schizochytrium*, it is recognized that microalgae strains in related taxonomic classifications with similar characteristics to *Schizochytrium* would reasonably be expected to produce similar results.

By artificially controlling aspects of the microalgae culturing process such as the organic carbon feed (e.g., acetic acid, acetate), oxygen levels, pH, and light, the culturing process differs from the culturing process that microalgae experiences in nature. In addition to controlling various aspects of the culturing process, intervention by human operators or automated systems occurs during the non-axenic mixotrophic culturing of microalgae through contamination control methods to prevent the microalgae from being overrun and outcompeted by contaminating organisms (e.g., fungi, bacteria). Contamination control methods for microalgae cultures are known in the art and such suitable contamination control methods for non-axenic mixotrophic microalgae cultures are disclosed in WO2014/074769A2 (Ganuza, et al.), hereby incorporated by reference. By intervening in the microalgae culturing process, the impact of the contaminating microorganisms can be mitigated by suppressing the proliferation of containing organism populations and the effect on the microalgal cells (e.g., lysing, infection, death, clumping). Thus, through artificial control of aspects of the culturing process and intervening in the culturing process with contamination control methods, the microalgae culture produced as a whole and used in the described inventive compositions differs from the culture that results from a microalgae culturing process that occurs in nature.

During the mixotrophic culturing process the microalgae culture can also include cell debris and compounds excreted from the microalgae cells into the culture medium. The output of the microalgae mixotrophic culturing process provides the active ingredient for composition that is applied to plants for improving yield and quality without separate addition to or supplementation of the composition with other active ingredients not found in the mixotrophic microalgae whole cells and accompanying culture medium from the mixotrophic culturing process such as, but not limited to: microalgae extracts, macroalgae, macroalgae extracts, liquid fertilizers, granular fertilizers, mineral complexes (e.g., calcium, sodium, zinc, manganese, cobalt, silicon), fungi, bacteria, nematodes, protozoa, digestate solids, chemicals (e.g., ethanolamine, borax, boric acid), humic acid, nitrogen and nitrogen derivatives, phosphorus rock, pesticides, herbicides, insecticides, enzymes, plant fiber (e.g., coconut fiber).

In some embodiments, the microalgae can be previously frozen and thawed before inclusion in the liquid composition. In some embodiments, the microalgae may not have been subjected to a previous freezing or thawing process. In some embodiments, the microalgae whole cells have not been subjected to a drying process. The cell walls of the microalgae of the composition have not been lysed or disrupted, and the microalgae cells have not been subjected to an extraction process or process that pulverizes the cells. The microalgae whole cells are not subjected to a purification process for isolating the microalgae whole cells from the accompanying constituents of the culturing process (e.g., trace nutrients, residual organic carbon, bacteria, cell debris, cell excretions), and thus the whole output from the microalgae culturing process comprising whole microalgae cells, culture medium, cell excretions, cell debris, bacteria, residual organic carbon, and trace nutrients, is used in the liquid composition for application to plants. In some embodiments, the microalgae whole cells and the accompanying constituents of the culturing process are concentrated in the composition. In some embodiments, the microalgae whole cells and the accompanying constituents of the culturing process are diluted in the composition to a low concentration. The microalgae whole cells of the composition are not fossilized. In some embodiments, the microalgae whole cells are not maintained in a viable state in the composition for continued growth after the method of using the composition in a soil or foliar application. In some embodiments, the microalgae base composition can be biologically inactive after the composition is prepared. In some embodiments, the microalgae base composition can be substantially biologically inactive after the composition is prepared. In some embodiments, the microalgae base composition can increase in biological activity after the prepared composition is exposed to air.

In some embodiments, a liquid composition can include low concentrations of bacteria contributing to the solids percentage of the composition in addition to the microalgae cells. Examples of bacteria found in non-axenic mixotrophic conditions can be found in WO2014/074769A2 (Ganuza, et al.), hereby incorporated by reference. A live bacteria count can be determined using methods known in the art such as plate counts, plates counts using Petrifilm available from 3M (St. Paul, Minn.), spectrophotometric (turbidimetric) measurements, visual comparison of turbidity with a known standard, direct cell counts under a microscope, cell mass determination, and measurement of cellular activity. Live bacteria counts in a non-axenic mixotrophic microalgae culture can range from $10^4$ to $10^9$ CFU/mL, and can depend on contamination control measures taken during the culturing of the microalgae. The level of bacteria in the composition can be determined by an aerobic plate count which quantifies aerobic colony forming units (CFU) in a designated volume. In some embodiments, the composition includes an aerobic plate count of 40,000-400,000 CFU/mL. In some embodiments, the composition includes an aerobic plate count of 40,000-100,000 CFU/mL. In some embodiments, the composition includes an aerobic plate count of 100,000-200,000 CFU/mL. In some embodiments, the composition includes an aerobic plate count of 200,000-300,000 CFU/mL. In some embodiments, the composition includes an aerobic plate count of 300,000-400,000 CFU/mL.

In some embodiments, the microalgae based composition can be supplemented with a supplemental nutrient such as nitrogen, phosphorus, or potassium to increase the levels within the composition to at least 1% of the total composition (i.e., addition of N, P, or K to increase levels at least 1-0-0, 0-1-0, 0-0-1, or combinations thereof). In some embodiments, the microalgae composition can be supplemented with nutrients such as, but not limited to, calcium, magnesium, silicon, sulfur, iron, manganese, zinc, copper, boron, molybdenum, chlorine, sodium, aluminum, vanadium, nickel, cerium, dysprosium, erbium, europium, gadolinium, holmium, lanthanum, lutetium, neodymium, praseodymium, promethium, samarium, scandium, terbium, thulium, ytterbium, and yttrium. In some embodiments, the supplemented nutrient is not uptaken, chelated, or absorbed by the microalgae. In some embodiments, the concentration of the supplemental nutrient can include 1-50 g per 100 g of the composition.

A liquid composition comprising microalgae can be stabilized by heating and cooling in a pasteurization process. As shown in the Examples, the inventors found that the active ingredients of the microalgae based composition maintained effectiveness in at least one characteristic of a plant after being subjected to the heating and cooling of a pasteurization process. In other embodiments, liquid compositions with whole cells or processed cells (e.g., dried, lysed, extracted) of microalgae cells may not need to be stabilized by pasteurization. For example, microalgae cells that have been processed, such as by drying, lysing, and extraction, or extracts can include such low levels of bacteria that a liquid composition can remain stable without being subjected to the heating and cooling of a pasteurization process.

In some embodiments, the composition can be heated to a temperature in the range of 50-130° C. In some embodiments, the composition can be heated to a temperature in the range of 55-65° C. In some embodiments, the composition can be heated to a temperature in the range of 58-62° C. In some embodiments, the composition can be heated to a temperature in the range of 50-60° C. In some embodiments, the composition can be heated to a temperature in the range of 60-90° C. In some embodiments, the composition can be heated to a temperature in the range of 70-80° C. In some embodiments, the composition can be heated to a temperature in the range of 100-150° C. In some embodiments, the composition can be heated to a temperature in the range of 120-130° C.

In some embodiments, the composition can be heated for a time period in the range of 1-150 minutes. In some embodiments, the composition can be heated for a time period in the range of 110-130 minutes. In some embodiments, the composition can be heated for a time period in the range of 90-100 minutes. In some embodiments, the composition can be heated for a time period in the range of 100-110 minutes. In some embodiments, the composition can be heated for a time period in the range of 110-120 minutes. In some embodiments, the composition can be heated for a time period in the range of 120-130 minutes. In some embodiments, the composition can be heated for a time period in the range of 130-140 minutes. In some embodiments, the composition can be heated for a time period in the range of 140-150 minutes. In some embodiments, the composition is heated for less than 15 min. In some embodiments, the composition is heated for less than 2 min.

After the step of heating or subjecting the liquid composition to high temperatures is complete, the compositions can be cooled at any rate to a temperature that is safe to work with. In one non-limiting embodiment, the composition can be cooled to a temperature in the range of 35-45° C. In some embodiments, the composition can be cooled to a temperature in the range of 36-44° C. In some embodiments, the composition can be cooled to a temperature in the range of 37-43° C. In some embodiments, the composition can be cooled to a temperature in the range of 38-42° C. In some embodiments, the composition can be cooled to a temperature in the range of 39-41° C. In further embodiments, the pasteurization process can be part of a continuous production process that also involves packaging, and thus the liquid composition can be packaged (e.g., bottled) directly after the heating or high temperature stage without a cooling step.

In some embodiments, the composition can include 5-30% solids by weight of microalgae cells (i.e., 5-30 g of microalgae cells/100 mL of the liquid composition). In some embodiments, the composition can include 5-20% solids by weight of microalgae cells. In some embodiments, the composition can include 5-15% solids by weight of microalgae cells. In some embodiments, the composition can include 5-10% solids by weight of microalgae cells. In some embodiments, the composition can include 10-20% solids by weight of microalgae cells. In some embodiments, the composition can include 10-20% solids by weight of microalgae cells. In some embodiments, the composition can include 20-30% solids by weight of microalgae cells. In some embodiments, further dilution of the microalgae cells percent solids by weight can occur before application for low concentration applications of the composition.

In some embodiments, the composition can include less than 1% by weight of microalgae biomass or extracts (i.e., less than 1 g of microalgae derived product/100 mL of the liquid composition). In some embodiments, the composition can include less than 0.9% by weight of microalgae biomass or extracts. In some embodiments, the composition can include less than 0.8% by weight of microalgae biomass or extracts. In some embodiments, the composition can include less than 0.7% by weight of microalgae biomass or extracts. In some embodiments, the composition can include less than 0.6% by weight of microalgae biomass or extracts. In some embodiments, the composition can include less than 0.5% by weight of microalgae biomass or extracts. In some embodiments, the composition can include less than 0.4% by weight of microalgae biomass or extracts. In some embodiments, the composition can include less than 0.3% by weight of microalgae biomass or extracts. In some embodiments, the composition can include less than 0.2% by weight of microalgae biomass or extracts. In some embodiments, the composition can include less than 0.1% by weight of microalgae biomass or extracts. In some embodiments, the composition can include at least 0.0001% by weight of microalgae biomass or extracts. In some embodiments, the composition can include at least 0.001% by weight of microalgae biomass or extracts. In some embodiments, the composition can include at least 0.01% by weight of microalgae biomass or extracts. In some embodiments, the composition can include at least 0.1% by weight of microalgae biomass or extracts. In some embodiments, the composition can include 0.0001-1% by weight of microalgae biomass or extracts. In some embodiments, the composition can include 0.0001-0.001% by weight of microalgae biomass or extracts. In some embodiments, the composition can include 0.001-0.01% by weight of microalgae biomass or extracts. In some embodiments, the composition can include 0.01-0.1% by weight of microalgae biomass or extracts. In some embodiments, the composition can include 0.1-1% by weight of microalgae biomass or extracts.

In some embodiments, an application concentration of 0.1% of microalgae biomass or extract equates to 0.04 g of microalgae biomass or extract in 40 mL of a composition. While the desired application concentration to a plant can be 0.1% of microalgae biomass or extract, the composition can be packaged as a 10% concentration (0.4 mL in 40 mL of a composition). Thus, a desired application concentration of 0.1% would require 6,000 mL of the 10% microalgae biomass or extract in the 100 gallons of water applied to the assumption of 15,000 plants in an acre, which is equivalent to an application rate of about 1.585 gallons per acre. In some embodiments, a desired application concentration of 0.01% of microalgae biomass or extract using a 10% concentration composition equates to an application rate of about 0.159 gallons per acre. In some embodiments, a desired application concentration of 0.001% of microalgae biomass or extract using a 10% concentration composition equates to an application rate of about 0.016 gallons per acre. In some embodiments, a desired application concentration of 0.0001% of microalgae biomass or extract using a 10% concentration composition equates to an application rate of about 0.002 gallons per acre.

In another non-limiting embodiment, correlating the application of the microalgae biomass or extract on a per plant basis using the assumption of 15,000 plants per acre, the composition application rate of 1 gallon per acre is equal to about 0.25 mL per plant=0.025 g per plant=25 mg of microalgae biomass or extract per plant. The water requirement assumption of 100 gallons per acre is equal to about 35 mL of water per plant. Therefore, 0.025 g of microalgae biomass or extract in 35 mL of water is equal to about 0.071 g of microalgae biomass or extract per 100 mL of composition equates to about a 0.07% application concentration. In some embodiments, the microalgae biomass or extract based composition can be applied at a rate in a range as low as about 0.001-10 gallons per acre, or as high as up to 150 gallons per acre. In some of the embodiments and Examples below, the applications were performed using a 10% solids solution by weight microalgae composition. For these field trials, the rates are indicated in gal/acre and the amount of carrier water would be determined according to user preference. For field trials, the application rate may range between 0.25 gal/acre-2 gal/acre. In the field trials, where the application rate of the microalgae composition is 0.25 gal/acre, the equivalent expressed in total grams of solid microalgae would be 100 g microalgae/acre; wherein the application rate of the microalgae composition is 0.4 gal/acre, the equivalent expressed in total grams of solid microalgae would be 160 g microalgae/acre; where the application rate of the microalgae composition is 0.5 gal/acre, the equivalent expressed in total grams of solid microalgae would be 200 g microalgae/acre; where the application rate of the microalgae composition is 1.0 gal/acre, the equivalent expressed in total grams of solid microalgae would be 400 g microalgae/acre; and where the application rate of the microalgae composition is 2.0 gal/acre, the equivalent expressed in total grams of solid microalgae would be 800 g microalgae/acre.

Overall, as shown in the embodiments and Examples below, the microalgae composition may comprise between 100 g-800 g per acre, as it is common practice for growers to use between 100-250 gallons of liquid carrier volume/acre. It should be clearly understood, however, that modifications to the amount of microalgae per acre may be adjusted upwardly or downwardly to compensate for greater than 250 gallons of liquid carrier volume/acre or less than 100 gallons of liquid carrier volume/acre.

In some embodiments, stabilizing means that are not active regarding the improvement of plant germination, emergence, maturation, quality, and yield, but instead aid in stabilizing the composition can be added to prevent the proliferation of unwanted microorganisms (e.g., yeast, mold) and prolong shelf life. Such inactive but stabilizing means can include an acid, such as but not limited to phosphoric acid or citric acid, and a yeast and mold inhibitor, such as but not limited to potassium sorbate. In some embodiments, the stabilizing means are suitable for plants and do not inhibit the growth or health of the plant. In the alternative, the stabilizing means can contribute to nutritional properties of the liquid composition, such as but not limited to, the levels of nitrogen, phosphorus, or potassium.

In some embodiments, the composition can include between 0.5-1.5% phosphoric acid. In other embodiments, the composition may comprise less than 0.5% phosphoric acid. In some embodiments, the composition can include 0.01-0.3% phosphoric acid. In some embodiments, the composition can include 0.05-0.25% phosphoric acid. In some embodiments, the composition can include 0.01-0.1% phosphoric acid. In some embodiments, the composition can include 0.1-0.2% phosphoric acid. In some embodiments, the composition can include 0.2-0.3% phosphoric acid. In some embodiments, the composition can include less than 0.3% citric acid.

In some embodiments, the composition can include 1.0-2.0% citric acid. In other embodiments, the composition can include 0.01-0.3% citric acid. In some embodiments, the composition can include 0.05-0.25% citric acid. In some embodiments, the composition can include 0.01-0.1% citric acid. In some embodiments, the composition can include 0.1-0.2% citric acid. In some embodiments, the composition can include 0.2-0.3% citric acid.

In some embodiments, the composition can include less than 0.5% potassium sorbate. In some embodiments, the composition can include 0.01-0.5% potassium sorbate. In some embodiments, the composition can include 0.05-0.4% potassium sorbate. In some embodiments, the composition can include 0.01-0.1% potassium sorbate. In some embodiments, the composition can include 0.1-0.2% potassium sorbate. In some embodiments, the composition can include 0.2-0.3% potassium sorbate. In some embodiments, the composition can include 0.3-0.4% potassium sorbate. In some embodiments, the composition can include 0.4-0.5% potassium sorbate.

The present invention involves the use of a microalgae composition. Microalgae compositions, methods of preparing liquid microalgae compositions, and methods of applying the microalgae compositions to plants are disclosed in WO2017/218896A1 (Shinde et al.) entitled Microalgae-Based Composition, and Methods of its Preparation and Application to Plants, which is incorporated herein in full by reference. In one or more embodiments, the microalgae composition may comprise approximately 10%-10.5% w/w of *Chlorella* microalgae cells. In one or more embodiments, the microalgae composition may also comprise one of more stabilizers, such as potassium sorbate, phosphoric acid, ascorbic acid, sodium benzoate, citric acid, or the like, or any combination thereof. For example, in one or more embodiments, the microalgae composition may comprise approximately 0.3% w/w of potassium sorbate or another similar compound to stabilize its pH and may further comprise approximately 0.5-1.5% w/w phosphoric acid or another similar compound to prevent the growth of contaminants. As a further example, in one or more embodiments where it is desired to use an OMRI (Organic Materials Review Institute) certified organic composition, the microalgae composition may comprise 1.0-2.0% w/w citric acid to stabilize its pH, and may not contain potassium sorbate or phosphoric acid. In one or more embodiments, the pH of the microalgae composition may be stabilized to between 3.0-4.0.

In some embodiments and Examples below, the microalgae composition may be referred to as PHYCOTERRA®. The PHYCOTERRA® *Chlorella* microalgae composition is a microalgae composition comprising *Chlorella*. The PHYCOTERRA® *Chlorella* microalgae composition treatments were prepared by growing the *Chlorella* in non-axenic acetic acid supplied mixotrophic conditions, increasing the concentration of *Chlorella* using a centrifuge, pasteurizing the concentrated *Chlorella* at between 65° C.-75° C. for between 90-150 minutes, adding potassium sorbate and phosphoric acid to stabilize the pH of the *Chlorella*, and then adjusting the whole biomass treatment to the desired concentration. The PHYCOTERRA® *Chlorella* microalgae composition may comprise approximately 10% w/w of *Chlorella* microalgae cells. Furthermore, the PHYCOTERRA® *Chlorella* microalgae composition may comprise between approximately 0.3% potassium sorbate and between approximately 0.5%-1.5% phosphoric acid to stabilize the pH of the *Chlorella* to between 3.0-4.0 and 88.2%-89.2% water. It should be clearly understood, however, that other variations of the PHYCOTERRA® *Chlorella* microalgae composition, including variations in the microalgae strains, variations in the stabilizers, and/or variations in the % composition of each component may be used and may achieve similar results.

In some embodiments and Examples below, the microalgae composition may be an OMRI certified microalgae composition referred to as PhycoTerra Organic® (previously known as TERRENE®. The OMRI certified PhycoTerra Organic® shall be referred to hereinafter as PT-O for brevity. PT-O *Chlorella* microalgae composition is a microalgae composition comprising *Chlorella*. PT-O *Chlorella* microalgae composition treatments were prepared by growing the *Chlorella* in non-axenic acetic acid supplied mixotrophic conditions, increasing the concentration of *Chlorella* using a centrifuge, pasteurizing the concentrated *Chlorella* at between 65° C.-75° C. for between 90-150 minutes, adding citric acid to stabilize the pH of the *Chlorella*, and then adjusting the whole biomass treatment to the desired concentration. PT-O *Chlorella* microalgae composition may comprise approximately 10% w/w of *Chlorella* microalgae cells. Furthermore, PT-O *Chlorella* microalgae composition may comprise between approximately 0.5%-2.0% citric acid to stabilize the pH of the *Chlorella* to between 3.0-4.0 and 88%-89.5% water. It should be clearly understood, however, that other variations of PT-O *Chlorella* microalgae composition, including variations in the microalgae strains, variations in the stabilizers, and/or variations in the % composition of each component may be used and may achieve similar results.

In some embodiments and Examples below, the microalgae composition may be an OMRI certified microalgae composition referred to as OMRI certified PhycoTerra® Organic *Chlorella* pasteurized at 65° C. microalgae composition or as PT-O65. PT-O *Chlorella* pasteurized at 65° C. microalgae composition is a microalgae composition comprising *Chlorella*. PT-O *Chlorella* pasteurized at 65° C. microalgae composition treatments were prepared by growing the *Chlorella* in non-axenic acetic acid supplied mixotrophic conditions, increasing the concentration of *Chlorella* using a centrifuge, pasteurizing the concentrated *Chlorella* at 65° C. for between 90-150 minutes, adding citric acid to stabilize the pH of the *Chlorella*, and then adjusting the whole biomass treatment to the desired concentration. PT-O *Chlorella* pasteurized at 65° C. microalgae composition may comprise approximately 10% w/w of *Chlorella* microalgae cells. Furthermore, PT-O *Chlorella* pasteurized at 65° C. microalgae composition may comprise between approximately 0.5%-2.0% citric acid to stabilize the pH of the *Chlorella* to between 3.0-4.0 and 88-89.5% water. It should be clearly understood, however, that other variations of PT-O *Chlorella* pasteurized at 65° C. microalgae composition, including variations in the microalgae strains, variations in the stabilizers, variations in the pasteurization temperature, and/or variations in the % composition of each component may be used and may achieve similar results.

In some embodiments and Examples below, the microalgae composition may be an OMRI certified microalgae composition referred to as PT-O *Chlorella* pasteurized at 90° C. microalgae composition or as PT-O90. PT-O *Chlorella* pasteurized at 90° C. microalgae composition is a microalgae composition comprising *Chlorella*. PT-O *Chlorella* pasteurized at 90° C. microalgae composition treatments were prepared by growing the *Chlorella* in non-axenic acetic acid supplied mixotrophic conditions, increasing the concentration of *Chlorella* using a centrifuge, pasteurizing the concentrated *Chlorella* at 90° C. for between 90-150 minutes, adding citric acid to stabilize the pH of the *Chlorella*, and then adjusting the whole biomass treatment to the desired concentration. PT-O *Chlorella* pasteurized at 90° C. microalgae composition may comprise approximately 10% w/w of *Chlorella* microalgae cells. Furthermore, PT-O *Chlorella* pasteurized at 90° C. microalgae composition may comprise between approximately 0.5%-2.0% citric acid to stabilize the pH of the *Chlorella* to between 3.0-4.0 and 88-89.5% water. It should be clearly understood that other variations of PT-O *Chlorella* pasteurized at 90° C. microalgae composition, including variations in the microalgae strains, variations in the stabilizers, variations in the pasteurization temperature, and/or variations in the % composition of each component may be used and may achieve similar results.

In some embodiments and Examples below, the microalgae composition may be referred to as *Aurantiochytrium acetophilum* HS399 whole biomass (WB) or HS399 WB. The *Aurantiochytrium acetophilum* HS399 whole biomass (WB) microalgae composition is a microalgae composition comprising *Aurantiochytrium acetophilum* HS399. The *Aurantiochytrium acetophilum* HS399 whole biomass (WB) microalgae composition treatments were prepared by growing the *Aurantiochytrium acetophilum* HS399 microalgae in non-axenic acetic acid supplied heterotrophic conditions, increasing the concentration of *Aurantiochytrium acetophilum* HS399 using a centrifuge, pasteurizing the concentrated *Aurantiochytrium acetophilum* HS399 at between 65° C.-75° C. for between 90-150 minutes, adding approximately 0.3% w/w of potassium sorbate and between approximately 0.5-1.5% phosphoric acid to stabilize the pH of the *Aurantiochytrium acetophilum* HS399 to between 3.0-4.0, and then adjusting the whole biomass to a desired concentration. It should be clearly understood that other variations of the *Aurantiochytrium acetophilum* HS399 whole biomass (WB) microalgae composition, including variations in the microalgae strains, variations in the stabilizers, variations in the pasteurization temperature, and/or variations in the % composition of each component may be used and may achieve similar results.

In some embodiments and Examples below, the microalgae composition may be referred to as *Aurantiochytrium acetophilum* HS399 washed whole biomass (WB washed). The *Aurantiochytrium acetophilum* HS399 washed whole biomass (WB washed) microalgae composition is a microalgae composition comprising *Aurantiochytrium acetophilum* HS399. The *Aurantiochytrium acetophilum* HS399 washed whole biomass (WB washed) microalgae composition treatments were prepared by growing the *Aurantiochytrium acetophilum* HS399 microalgae in non-axenic acetic acid supplied heterotrophic conditions, increasing the concentration of *Aurantiochytrium acetophilum* HS399 using a centrifuge, pasteurizing the concentrated *Aurantiochytrium acetophilum* HS399 at between 65° C.-75° C. for between 90-150 minutes, adding approximately 0.3% w/w of potassium sorbate and between approximately 0.5%-1.5% phosphoric acid to stabilize the pH of the *Aurantiochytrium acetophilum* HS399 to between 3.0-4.0, and then adjusting the whole biomass to a desired concentration. Once the *Aurantiochytrium acetophilum* HS399 microalgae cells were concentrated from the harvest, they were washed; i.e. diluted with water in a ratio of 5:1 and centrifuged again in order to remove dissolved material and small particles. It should be clearly understood that other variations of the *Aurantiochytrium acetophilum* HS399 washed whole biomass (WB washed) microalgae composition, including variations in the microalgae strains, variations in the stabilizers, variations in the pasteurization temperature, variations in the washing method, and/or variations in the % composition of each component may be used and may achieve similar results.

In some embodiments and Examples below, the microalgae composition may be referred to as *Aurantiochytrium acetophilum* HS399 extracted biomass (EB) or HS399 EB. The *Aurantiochytrium acetophilum* HS399 extracted biomass (EB) microalgae composition is a microalgae composition comprising *Aurantiochytrium acetophilum* HS399. The *Aurantiochytrium acetophilum* HS399 extracted biomass (EB) treatments were prepared by growing the *Aurantiochytrium acetophilum* HS399 microalgae in non-axenic acetic acid supplied heterotrophic conditions, increasing the concentration of *Aurantiochytrium acetophilum* HS399 using a centrifuge, pasteurizing the concentrated *Aurantiochytrium acetophilum* HS399 at between 65° C.-75° C. for between 90-150 minutes, adding approximately 0.3% w/w of potassium sorbate and between approximately 0.5%-1.5% phosphoric acid to stabilize the pH of the *Aurantiochytrium acetophilum* HS399 to between 3.0-4.0, processing the *Aurantiochytrium acetophilum* HS399 with an oat filler in an expeller process to lyse the cells and separate oil from the residual biomass, and then adjusting the residual biomass to a desired concentration. It should be clearly understood that other variations of the *Aurantiochytrium acetophilum* HS399 extracted biomass (EB) microalgae composition, including variations in the microalgae strains, variations in the stabilizers, variations in the pasteurization temperature, variations in the extraction method, and/or variations in the % composition of each component may be used and may achieve similar results.

In some embodiments and Examples below, the microalgae composition may be referred to as a combination 25% *Chlorella*: 75% HS399 whole biomass (WB) microalgae composition or 25% *Chlorella*: 75% HS399 WB. The combination 25% *Chlorella*: 75% HS399 whole biomass (WB) microalgae composition is a microalgae composition comprising *Chlorella* and *Aurantiochytrium acetophilum* HS399. For the combination 25% *Chlorella*: 75% HS399 whole biomass (WB) microalgae composition, the *Chlorella* microalgae cells were cultured in outdoor pond reactors in non-axenic acetic acid supplied mixotrophic conditions and the concentration of *Chlorella* was increased using a centrifuge. The *Aurantiochytrium acetophilum* HS399 cells were cultured in non-axenic acetic-acid supplied heterotrophic conditions and the concentration of HS399 was increased using a centrifuge. The concentrated *Chlorella* cells were then combined with the concentrated HS399 whole biomass cells and adjusted to the desired concentration of 25% *Chlorella*: 75% HS399 whole biomass (WB). The combination 25% *Chlorella*: 75% HS399 whole biomass (WB) microalgae composition was then pasteurized at between 65° C.-75° C. for between 90-150 minutes and then stabilized by adding approximately 0.3% w/w of potassium sorbate and between approximately 0.5%-1.5% phosphoric acid to stabilize the pH of the 25% *Chlorella*: 75% HS399 whole biomass (WB) microalgae composition to between 3.0-4.0. It should be clearly understood, however, that other variations of the combination 25% *Chlorella*: 75% HS399 whole biomass (WB) microalgae composition, including variations in the microalgae strains, variations in the stabilizers, variations in the order of the processing steps (blending, pasteurizing, stabilizing), and/or variations in the % composition of each component may be used and may achieve similar results.

In some embodiments and Examples below, the microalgae composition may be referred to as GP2C. The GP2C *Chlorella* microalgae composition comprised *Chlorella*. The GP2C *Chlorella* microalgae composition treatments were prepared by growing the *Chlorella* in non-axenic acetic acid supplied mixotrophic conditions, increasing the concentration of *Chlorella* using a centrifuge, pasteurizing the concentrated *Chlorella* at between 65° C.-75° C. for between 90-150 minutes, adding potassium sorbate and phosphoric acid to stabilize the pH of the *Chlorella*, and then adjusting the whole biomass treatment to the desired concentration. The GP2C *Chlorella* microalgae composition may comprise approximately 10% w/w of *Chlorella* microalgae cells. Furthermore, the GP2C microalgae composition may comprise between approximately 0.3% potassium sorbate and between approximately 05%-1.5% phosphoric acid to stabilize the pH of the *Chlorella* to between 3.0-4.0 and 88.2%-89% water. It should be clearly understood, however, that other variations of the GP2C *Chlorella* microalgae composition, including variations in the microalgae strains, variations in the stabilizers, and/or variations in the % composition of each component may be used and may achieve similar results.

In some embodiments and Examples below, the microalgae composition may be referred to as a combination 25% *Chlorella*: 75% HS399 extracted biomass (EB) microalgae composition, a 50% *Chlorella*: 50% HS399 extracted biomass (EB) microalgae composition, a 75% *Chlorella*: 25% HS399 extracted biomass (EB) microalgae composition, or a combination GP2C:399 microalgae composition. The combination GP2C:399 microalgae composition comprises *Chlorella* and *Aurantiochytrium acetophilum* HS399 extracted biomass (EB). For the combination GP2C:399 microalgae composition, the *Chlorella* microalgae cells were cultured in outdoor pond reactors in non-axenic acetic acid supplied mixotrophic conditions and the concentration of *Chlorella* was increased using a centrifuge; the *Aurantiochytrium acetophilum* HS399 microalgae cells were cultured in non-axenic acetic acid supplied heterotrophic conditions, the concentration of HS399 was increased using a centrifuge, and the HS399 cells were then processed with an oat filler in an expeller process to lyse the cells and separate oil from the residual biomass. The concentrated GP2C *Chlorella* whole biomass microalgae cells and the *Aurantiochytrium acetophilum* HS399 extracted biomass (EB) microalgae cells were blended together to the ratios of 50:50, 25:75, and 75:25, then pasteurized at between 65° C.-75° C. for between 90-150 minutes and then stabilized by adding approximately 0.3% w/w of potassium sorbate and between approximately 0.5%-1.5% phosphoric acid to stabilize the pH of the 25% *Chlorella*: 75% HS399 extracted biomass (EB) microalgae composition to between 3.0-4.0. It should be clearly understood, however, that other variations of the combination GP2C:399 microalgae composition, including variations in the microalgae strains, variations in the stabilizers, variations in the order of the processing steps (blending, pasteurizing, stabilizing), and/or variations in the % composition of each component may be used and may achieve similar results.

In some embodiments and Examples below, a Greenwater Polyculture (GWP) treatment may be used. Greenwater Polyculture may be prepared by beginning with a culture of *Scenedesmus* microalgae that is left outdoors in an open pond and harvested continuously over a year. The culture may comprise anywhere from less than 50% *Scenedesmus* to greater than 75% *Scenedesmus* and the concentration varies throughout the year. Other algae may colonize in the GWP as well as other bacteria and microorganisms.

In some embodiments, the composition is a liquid and substantially includes of water. In some embodiments, the composition can include 70-99% water. In some embodiments, the composition can include 85-95% water. In some embodiments, the composition can include 70-75% water. In some embodiments, the composition can include 75-80% water. In some embodiments, the composition can include 80-85% water. In some embodiments, the composition can include 85-90% water. In some embodiments, the composition can include 90-95% water. In some embodiments, the composition can include 95-99% water. The liquid nature and high-water content of the composition facilitates administration of the composition in a variety of manners, such as but not limit to: flowing through an irrigation system, flowing through an above ground drip irrigation system, flowing through a buried drip irrigation system, flowing through a central pivot irrigation system, sprayers, sprinklers, and water cans.

In some embodiments, the liquid composition can be used immediately after formulation, or can be stored in containers for later use. In some embodiments, the composition can be stored out of direct sunlight. In some embodiments, the composition can be refrigerated. In some embodiments, the composition can be stored at 1-10° C. In some embodiments, the composition can be stored at 1-3° C. In some embodiments, the composition can be stored at 3-50° C. In some embodiments, the composition can be stored at 5-8° C. In some embodiments, the composition can be stored at 8-10° C.

In some embodiments, administration of the liquid composition to soil, a seed or plant can be in an amount effective to produce an enhanced characteristic in plants compared to a substantially identical population of untreated seeds or plants. Such enhanced characteristics can include accelerated seed germination, accelerated seedling emergence, improved seedling emergence, improved leaf formation, accelerated leaf formation, improved plant maturation, accelerated plant maturation, increased plant yield, increased plant growth, increased plant quality, increased plant health, increased fruit yield, increased fruit sweetness, increased fruit growth, and increased fruit quality. Non-limiting examples of such enhanced characteristics can include accelerated achievement of the hypocotyl stage, accelerated protrusion of a stem from the soil, accelerated achievement of the cotyledon stage, accelerated leaf formation, increased marketable plant weight, increased marketable plant yield, increased marketable fruit weight, increased production plant weight, increased production fruit weight, increased utilization (indicator of efficiency in the agricultural process based on ratio of marketable fruit to unmarketable fruit), increased chlorophyll content (indicator of plant health), increased plant weight (indicator of plant health), increased root weight (indicator of plant health), increased shoot weight (indicator of plant health), increased plant height, increased thatch height, increased resistance to salt stress, increased plant resistance to heat stress (temperature stress), increased plant resistance to heavy metal stress, increased plant resistance to drought, increased plant resistance to disease, improved color, reduced insect damage, reduced blossom end rot, and reduced sun burn. Such enhanced characteristics can occur individually in a plant, or in combinations of multiple enhanced characteristics.

In some embodiments, a liquid composition can be administered before the seed is planted. In some embodiments, a liquid composition can be administered at the time the seed is planted. In some embodiments, a liquid composition can be applied by dip treatment of the roots. In some embodiments, a liquid composition can be administered to plants that have emerged from the ground. In some embodiments, a liquid or dried composition can be applied to the soil before, during, or after the planting of a seed. In some embodiments a liquid or dried composition can be applied to the soil before or after a plant emerges from the soil.

In some embodiments, the volume or mass of the microalgae based composition applied to a seed, seedling, or plant may not increase or decrease during the growth cycle of the plant (i.e., the amount of the microalgae composition applied to the plant will not change as the plant grows larger). In some embodiments, the volume or mass of the microalgae based composition applied to a seed, seedling, or plant can increase during the growth cycle of the plant (i.e., applied on a mass or volume per plant mass basis to provide more of the microalgae composition as the plant grows larger). In some embodiments, the volume or mass of the microalgae based composition applied to a seed, seedling, or plant can decrease during the growth cycle of the plant (i.e., applied on a mass or volume per plant mass basis to provide more of the microalgae composition as the plant grows larger).

In one non-limiting embodiment, the administration of the composition may comprise contacting the foliage of the plant with an effective amount of the composition. In some embodiments, the liquid composition may be sprayed on the foliage by a hand sprayer, a sprayer on an agriculture implement, or a sprinkler. In some embodiments, the composition can be applied to the soil.

The rate of application of the composition at the desired concentration can be expressed as a volume per area. In some embodiments, the rate of application of the liquid composition in a foliar application can comprise a rate in the range of 10-50 gallons/acre. In some embodiments, the rate of application of the liquid composition in a foliar application can comprise a rate in the rage of 10-15 gallons/acre. In some embodiments, the rate of application of the liquid composition in a foliar application can comprise a rate in the range of 15-20 gallons/acre. In some embodiments, the rate of application of the liquid composition in a foliar application can comprise a rate in the range of 20-25 gallons/acre. In some embodiments, the rate of application of the liquid composition in a foliar application can comprise a rate in the range of 25-30 gallons/acre. In some embodiments, the rate of application of the liquid composition in a foliar application can comprise a rate in the range of 30-35 gallons/acre. In some embodiments, the rate of application of the liquid composition in a foliar application can comprise a rate in the range of 35-40 gallons/acre. In some embodiments, the rate of application of the liquid composition in a foliar application can comprise a rate in the range of 40-45 gallons/acre. In some embodiments, the rate of application of the liquid composition in a foliar application can comprise a rate in the range of 45-50 gallons/acre.

In some embodiments, the rate of application of the liquid composition in a soil or foliar application can comprise a rate in the range of 0.01-10 gallons/acre. In some embodiments, the rate can be 0.12-4%. In some embodiments, the rate of application of the liquid composition in a foliar application may comprise a rate in the range of 0.01-0.1 gallons/acre. In some embodiments, the rate of application of the liquid composition in a soil or foliar application may comprise a rate in the range of 0.1-1.0 gallons/acre. In some embodiments, the rate of application of the liquid composition in a foliar application may comprise a rate in the range of 0.25-2 gallons/acre. In some embodiments, the rate of application of the liquid composition in a foliar application may comprise a rate in the range of 1-2 gallons/acre. In some embodiments, the rate of application of the liquid composition in a foliar application may comprise a rate in the range of 2-3 gallons/acre. In some embodiments, the rate of application of the liquid composition in a foliar application may comprise a rate in the range of 3-4 gallons/acre. In some embodiments, the rate of application of the liquid composition in a foliar application may comprise a rate in the range of 4-5 gallons/acre. In some embodiments, the rate of application of the liquid composition in a foliar application may comprise a rate in the range of 5-10 gallons/acre.

In some embodiments, the v/v ratio of the composition can be between 0.001%-50%. The v/v ratio can be between 0.01-25%. The v/v ratio of the composition can be between 0.03-10%.

The frequency of the application of the composition can be expressed as the number of applications per period of time (e.g., two applications per month), or by the period of time between applications (e.g., one application every 21 days). In some embodiments, the plant can be contacted by the composition in a foliar application every 3-28 days. In some embodiments, the plant can be contacted by the composition in a foliar application every 4-10 days. In some embodiments, the plant can be contacted by the composition in a foliar application every 18-24 days. In some embodiments, the plant can be contacted by the composition in a foliar application every 3-7 days. In some embodiments, the plant can be contacted by the composition in a foliar application every 7-14 days. In some embodiments, the plant can be contacted by the composition in a foliar application every 14-21 days. In some embodiments, the plant can be contacted by the composition in a foliar application every 21-28 days. In some embodiments, the soil or plant can be treated with the composition once per planting. In some embodiments, the soil or plant can be treated with the composition one time every cutting/harvest.

Foliar application(s) of the composition generally begin after the plant has become established, but can begin before establishment, at defined time period after planting, or at a defined time period after emergence from the soil in some embodiments. In some embodiments, the plant can be first contacted by the composition in a foliar application 5-14 days after the plant emerges from the soil. In some embodiments, the plant can be first contacted by the composition in a foliar application 5-7 days after the plant emerges from the soil. In some embodiments, the plant can be first contacted by the composition in a foliar application 7-10 days after the plant emerges from the soil. In some embodiments, the plant can be first contacted by the composition in a foliar application 10-12 days after the plant emerges from the soil. In some embodiments, the plant can be first contacted by the composition in a foliar application 12-14 days after the plant emerges from the soil.

In another non-limiting embodiment, the administration of the composition can include contacting the soil in the immediate vicinity of the planted seed with an effective amount of the composition. In some embodiments, the liquid composition can be supplied to the soil by injection into a low volume irrigation system, such as but not limited to a drip irrigation system supplying water beneath the soil through perforated conduits or at the soil level by fluid conduits hanging above the ground or protruding from the ground. In some embodiments, the liquid composition can be supplied to the soil by a soil drench method wherein the liquid composition is poured on the soil.

The composition can be diluted to a lower concentration for an effective amount in a soil application by mixing a volume of the composition in a volume of water. The percent solids of microalgae sourced components resulting in the diluted composition can be calculated by the multiplying the original concentration in the composition by the ratio of the volume of the composition to the volume of water. Alternatively, the grams of microalgae sourced components in the diluted composition can be calculated by the multiplying the original grams of microalgae sourced components per 100 mL by the ratio of the volume of the composition to the volume of water.

The rate of application of the composition at the desired concentration can be expressed as a volume per area. In some embodiments, the rate of application of the liquid composition in a soil application can include a rate in the range of 50-150 gallons/acre. In some embodiments, the rate of application of the liquid composition in a soil application can include a rate in the range of 75-125 gallons/acre. In some embodiments, the rate of application of the liquid composition in a soil application can include a rate in the range of 50-75 gallons/acre. In some embodiments, the rate of application of the liquid composition in a soil application can include a rate in the range of 75-100 gallons/acre. In some embodiments, the rate of application of the liquid composition in a soil application can include a rate in the range of 100-125 gallons/acre. In some embodiments, the rate of application of the liquid composition in a soil application can include a rate in the range of 125-150 gallons/acre.

In some embodiments, the rate of application of the liquid composition in a soil application can include a rate in the range of 10-50 gallons/acre. In some embodiments, the rate of application of the liquid composition in a soil application can include a rate in the range of 10-20 gallons/acre. In some embodiments, the rate of application of the liquid composition in a soil application can include a rate in the range of 20-30 gallons/acre. In some embodiments, the rate of application of the liquid composition in a soil application can include a rate in the range of 30-40 gallons/acre. In some embodiments, the rate of application of the liquid composition in a soil application can include a rate in the range of 40-50 gallons/acre.

In some embodiments, the rate of application of the liquid composition in a soil application can include a rate in the range of 0.01-10 gallons/acre. In some embodiments, the rate of application of the liquid composition in a soil application can include a rate in the range of 0.01-0.1 gallons/acre. In some embodiments, the rate of application of the liquid composition in a soil application can include a rate in the range of 0.1-1.0 gallons/acre. In some embodiments, the rate of application of the liquid composition in a soil application can include a rate in the range of 1-2 gallons/acre. In some embodiments, the rate of application of the liquid composition in a soil application can include a rate in the range of 2-3 gallons/acre. In some embodiments, the rate of application of the liquid composition in a soil application can include a rate in the range of 3-4 gallons/acre. In some embodiments, the rate of application of the liquid composition in a soil application can include a rate in the range of 4-5 gallons/acre. In some embodiments, the rate of application of the liquid composition in a soil application can include a rate in the range of 5-10 gallons/acre.

In some embodiments, the rate of application of the liquid composition in a soil application can include a rate in the range of 2-20 liters/acre. In some embodiments, the rate of application of the liquid composition in a soil application can include a rate in the range of 3.7-15 liters/acre. In some embodiments, the rate of application of the liquid composition in a soil application can include a rate in the range of 2-5 liters/acre. In some embodiments, the rate of application of the liquid composition in a soil application can include a rate in the range of 5-10 liters/acre. In some embodiments, the rate of application of the liquid composition in a soil application can include a rate in the range of 10-15 liters/acre. In some embodiments, the rate of application of the liquid composition in a soil application can include a rate in the range of 15-20 liters/acre.

Prior patent applications containing useful background information and technical details are PCT/US2017/053432 titled METHODS OF CULTURING *AURANTIOCHYTRIUM* USING ACETATE AS AN ORGANIC CARBON SOURCE, filed on Sep. 26, 2017; PCT/US2015/066160, titled MIXOTROPHIC *CHLORELLA*-BASED COMPOSITION, AND METHODS OF ITS PREPARATION AND APPLICATION TO PLANTS, filed on Dec. 15, 2015; and PCT/US2017/037878 and PCT/US2017/037880, both applications titled MICROALGAE-BASED COMPOSITION, AND METHODS OF ITS PREPARATION AND APPLICATION TO PLANTS, both filed on Jun. 16, 2017. Each of these applications is incorporated herein by reference in its entirety.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto. All patents and references cited herein are explicitly incorporated by reference in their entirety.

EXAMPLES

Example 1

Greenhouse trials were conducted to evaluate the effect of PT-O *Chlorella* microalgae composition on soil health. Soil was collected from a field planted with alfalfa from Gilbert, Ariz. classified as Antho sandy loam and diluted by 40% with a peat based soil mix and perlite to allow drainage. Quart pots were filled with soil and drenched bi-weekly with PT-O *Chlorella* microalgae composition (0.3-3% solution v/v in city water) or city water alone (UTC) starting on day 0. Pots were kept moist by watering every 2 days with city water. Soil samples were collected before set-up, immediately following application and then every 15 days and assayed for the following biological and physical soil health indicators: 1) active carbon—organic matter readily oxidized by soil microbes; 2) soil protein—organic nitrogen pool available to plants in soil; and 3) total water holding capacity—improves nutrient delivery and soil microbial health.

PT-O *Chlorella* microalgae composition causes an increase in biological soil health. After 2 applications of PT-O *Chlorella* microalgae composition (0.3-3%), active carbon increased in the soil from a "Medium" to a "Very High" health score. Soil protein was "Very Low" in the initial soil but increased to "medium" over 30 days compared to the UTC.

PT-O *Chlorella* microalgae composition causes a significant increase in the soil's water holding capacity. Water holding capacity of treated soil 30 days after the experiment started was increased 6-12% compared to the initial soil sample. Water holding capacity decreased over time for soil receiving water alone (UTC).

In summary, for a greenhouse study, two applications of PT-O *Chlorella* microalgae composition significantly improved the biological health of native Arizona field soil by promoting the accumulation of organic carbon and nitrogen and improving water holding capacity.

Improved Shelf-Life Quality and Post-Storage Marketability

Applying a microalgae composition to plants increases the shelf-life quality and consumer taste preference of harvested fruits. Shelf-life quality may include characteristics or metrics such as, but not limited to, fruit water retention, firmness, and reduction of bruising. Improvement of these factors leads to higher marketability of the fruits. Generally, fruits are stored after harvest at room temperature or in cold storage (<40° F.) for 5-20 days depending on the trial. For consumer preference 80-100 respondents were recruited and polled for their preference of treated and untreated strawberries.

Shelf-life metrics described in the Examples below may include: fruit water-retention; fruit firmness; reduction of bruising; consumer preference for appearance, overall liking, aroma, texture, and flavor (hedonics); and Christmas tree needle loss and water usage. Water-retention leads to a longer shelf-life due to the fact that the fruit maintains its water content longer post-harvest. Fruit is harvested and weighed immediately and then weighed again after a period of time specified for each trial. The difference in weight is attributed to the amount of water lost during the storage period. For testing firmness, a penetrometer is used to measure the force that it takes to penetrate the fruit surface. A firmer fruit indicates longer shelf-life. With respect to bruising, stored fruit is assessed for appearance and bruising is scored as "slight," "moderate," "severe," or "very severe." Berries with no bruising, slight/light bruising, and moderate bruising are considered "marketable." For determining consumer preference for appearance, overall liking, aroma, texture, and flavor (hedonics), a subset of treatments from 3 trials was shipped to a sensory lab for consumer testing. Reduced needle loss is an indicator of longer shelf-life of cut Christmas trees.

Example 2

A trial was conducted on strawberry (var. *camarosa*) in Winter Garden, Fla. to evaluate performance of the PHYCOTERRA® *Chlorella* microalgae composition on berry quality after storage and on consumer preference. The trial was transplanted in late October 2016 and harvested through early March 2017. All plots were managed according to the local standard practice (see Study Parameters below). Raw data is included in the table shown in FIG. 1.

| STUDY PARAMETERS | |
|---|---|
| Crop | Strawberry (var. *Camarosa*) |
| Location | Winter Garden, FL |
| Transplanting Date | Oct. 24, 2016 |
| Pick Frequency | Weekly culls when not assessed |
| Bed dimensions | 60" W × 6" H, 2 rows |
| Planting density | 17,424 plants/A |

-continued

| STUDY PARAMETERS | |
|---|---|
| Drip irrigation | 6" emitters, 0.3" applied daily |
| Fertilizer | 20-100 lbs 20-20-20 NPK monthly via drip |
| Pesticide | Ridomil, Sevin, Dipel and Captec as needed |
| Soil Type | Sandy, non-fumigated |
| Plot Size | 12 ft sections of 100 ft bed |
| Replication | 4 |
| Product applied | 0.5 gal/A via drip at planting then every 2 wks |

Berries from one harvest (day 113) were shipped cold overnight to a University lab in New York, stored for 3 days and then assessed for post-storage quality, particularly appearance. Berries from an additional harvest (day 128) were shipped to the Sensory Evaluation Center at a University in New York for consumer testing. Relative to standard practice alone (UTC), bi-weekly additions of the microalgae composition at 0.5 gal/A improved berry appearance after shipping and cold storage. Consumers consistently preferred berries that had come from plots treated with the microalgae composition over standard practice.

Berries from a mid-season harvest were assessed for shelf-life quality after being shipped cold to the University lab and stored for 3 days at 34° F. Post-storage marketability was determined by assessing the percent of stored berries with no to slight bruising, compared to those with moderate to severe bruising (unmarketable). Post-storage marketability was significantly improved for berries from plots treated with the microalgae composition. Berries from plots receiving the microalgae composition were preferred slightly more than those grown using local standard practice overall and for appearance, aroma, flavor, and texture when tested 2 days post-harvest.

In summary, for the Florida trial, the microalgae composition reduced the effects of post-harvest shipping and storage on berry quality (e.g. less bruising and improved appearance, aroma, flavor, and texture).

Example 3

A trial was conducted on strawberry (var. *camarosa*) in Winter Garden, Fla. to evaluate performance of each of the PHYCOTERRA® *Chlorella* microalgae composition and the *Aurantiochytrium acetophilum* HS399 extracted biomass (EB) microalgae composition on strawberry shelf-life and quality post-harvest. All plots received the standard fertilization regimen used by the grower for these crops excluding biostimulants. The *Chlorella* microalgae composition and the *Aurantiochytrium acetophilum* HS399 extracted biomass (EB) microalgae composition were added in addition to standard fertilization. Strawberry plants were transplanted to the field. First application of the microalgae compositions each occurred at time of transplanting and then every 14 days afterward until harvest via drip irrigation. The UTC received the same amount of carrier water as other treatments at the time of each application. The microalgae compositions were shaken well before application and agitated while in chemigation tank to prevent solids from settling. All plots were managed according to the local standard practice (see Study Parameters below).

| STUDY PARAMETERS | |
|---|---|
| Crop | Strawberry (var. *Camarosa*) |
| Location | Winter Garden, FL |
| Conventional Row Spacing | 2 rows/60" bed with plants every 12" |
| Plot size minimum | 12 ft section after first 2 ft along 100 ft drip line |
| Treatment | Treatment rows were randomized across field and untreated buffer rows were planted on both ends to minimize edge effects |
| | One 100 ft row, randomized in order throughout field |
| Observations | From multiple subsamples per 12 ft section |
| Replication | 14 treatments × 8 replicates = 112 treatment plots (12 ft sections) |
| Local Standard Production | Fertility, weed, insect management |
| Standard Management Practice | Fungicide application. Record disease management measures |

Application rates of the PHYCOTERRA® *Chlorella* microalgae composition and the *Aurantiochytrium acetophilum* HS399 extracted biomass (EB) microalgae composition were as detailed in Table 1 below.

TABLE 1

Treatments

| Treatment Number | Product | Application Rate gallon/acre |
|---|---|---|
| T1 | Standard Practice (Untreated) | N/A |
| T2 | PHYCOTERRA ® composition | 0.4 |
| T3 | PHYCOTERRA ® composition | 0.5 |
| T4 | PHYCOTERRA ® composition | 1 |
| T5 | PHYCOTERRA ® composition | 2 |
| T6 | HS399 Extracted Biomass (EB) | 0.4 |
| T7 | HS399 Extracted Biomass (EB) | 0.5 |
| T8 | HS399 Extracted Biomass (EB) | 1 |
| T9 | HS399 Extracted Biomass (EB) | 2 |
| T10 | Green Water Polyculture | 0.4 |
| T11 | Green Water Polyculture | 0.5 |
| T12 | Green Water Polyculture | 1 |
| T13 | Green Water Polyculture | 2 |
| T14 | Seaweed-based Commercial Reference | 0.5 |

Marketable berries from all replicates were harvested. Replicate 2 lb clamshells were kept for an on-site storage assessment or shipped overnight to a university lab in NY for an additional storage assessment. On-site, clamshells were placed at 38° F. for 4-5 days, followed by 24 hrs at ambient temperature. Berry quality was assessed after the storage period, using sub-sampling of individual berries when appropriate for the following characteristics: sweetness (% brix), firmness, post-harvest disease & decay. Once the second batch of replicates was received by the University, they were stored for 4 days at 34° F. and then assessed for post-storage quality.

A second harvest was conducted for a sensory panel. Upon harvest, 100 berries of similar size and ripeness from the standard practice and 2-3 additional treatments were packed into clamshells and shipped to a University sensory lab for sensory panel evaluation. Clamshells were wrapped in bubble wrap and shipped on blue ice.

Sixteen weeks after planting, strawberries were harvested and either kept in cold storage onsite or shipped overnight to the university lab where they were kept in cold storage. After a period of 4 days in storage, at both sites, berries were assessed for bruise severity and marketability. With few exceptions, all treatments improved marketability compared to standard practice by >20%. After shipping and storage, almost all treatments also improved marketability over the seaweed-based commercial reference product. Similar patterns were observed for the reduction of severe and moderate bruising. After shipping and storage, the PHYCOTERRA® *Chlorella* microalgae composition and the *Aurantiochytrium acetophilum* HS399 extracted biomass (EB) microalgae composition showed the most advantage.

Nineteen weeks after planting, strawberries were harvested and shipped overnight to a university sensory lab where they were kept at ambient conditions. The next day they were assessed by 74 respondents for various hedonics attributes. All treatments were tested at the ½ gallon/A rate. For every attribute, the PHYCOTERRA® *Chlorella* microalgae composition and the seaweed commercial reference were preferred over standard practice. The PHYCOTERRA® *Chlorella* microalgae composition was especially preferred over most treatments for aroma and texture liking. The *Aurantiochytrium acetophilum* HS399 extracted biomass (EB) microalgae composition was especially preferred for flavor liking. Greenwater Polyculture (GWP) tracked with other treatments in terms of advantages over standard practice.

Example 4

A trial was conducted on strawberry (var. *portola*) in Guadalupe Valley, Calif. to evaluate performance of various microalgae compositions on strawberry growth, yield, and post-harvest berry quality; specifically, the PHYCOTERRA® *Chlorella* microalgae composition, PT-O *Chlorella* pasteurized at 90° C. microalgae composition, the *Aurantiochytrium acetophilum* HS399 whole biomass (WB) microalgae composition, the *Aurantiochytrium acetophilum* HS399 washed whole biomass (WB washed) microalgae composition, and the combination 25% *Chlorella*: 75% HS399 whole biomass (WB) microalgae composition. All plots received standard local fertilization regimen used by the grower for this crop excluding biostimulants. Each of the microalgae compositions were added in addition to standard fertilization. Strawberry plants were transplanted to the field in early June 2017, according to local commercial practice. The first product application was via drip irrigation at the time of transplanting and then every 14 days afterward until harvest. The untreated control received the same amount of carrier water as other treatments at the time of each product application. The microalgae compositions were shaken well before application and agitated, if possible, while in the chemigation tank to prevent solids from settling. Berries were harvested according to local commercial schedule. All plots were managed according to the local standard practice (see Study Parameters below). Raw data is shown in Table 2 below.

| STUDY PARAMETERS | |
| --- | --- |
| Crop | Strawberry (var. *Portola*) |
| Location | Guadalupe Valley, CA |
| Conventional Row Spacing | 40" furrow spacing with 24" wide bed spacing, and plants on plant lines 12" apart and plant lines 12" apart |
| Harvest Schedule | As frequently as standard local grower practice with estimated 12-16 picks |
| Fumigation Schedule | Early May, 32 gal/a PicChlor60 |
| Plot size minimum | 1 double-line bed 45 ft length per plot with 80+ plants per plot |
| Trial Design | Randomized Complete Block |
| Observations | Taken from 70 plants inside 3 ft buffer zone of each plot end |
| Replication | 6 replicate plots for each treatment |
| Local Standard Production | Fertility, weed, insect management, etc. |
| Standard Management Practice | Fungicide application. Record disease management measures Fungicides will be applied weekly when flowers and fruit are present |

TABLE 2

Raw Data

| Holding Test | Treatment | Rate gal/A | % Weight loss | % Advantage over Standard Practice | % Advantage over Comm. Ref. | Day 5% bruising level | % Advantage over Standard Practice | % Advantage over Comm. Ref. | Day 7% bruising level | % Advantage Over Standard Practice | % Advantage Over Comm. Ref. |
| --- | --- | --- | --- | --- | --- | --- | --- | --- | --- | --- | --- |
| 1 | Standard Practice | | 2.13 | | | 1.28 | | | 1.63 | | |
| | Comm. Ref. | 0.50 | 1.88 | −12% | | 1.22 | −5% | | 1.40 | −14% | |
| | PhycoTerra | 0.25 | 1.87 | −12% | −1% | 0.93 | −27% | −23% | 1.43 | −12% | 2% |
| | PhycoTerra | 0.50 | 1.77 | −17% | −6% | 1.10 | −14% | −10% | 1.47 | −10% | 5% |
| | Terrene90 | 0.25 | 1.78 | −16% | −5% | 1.02 | −21% | −16% | 1.43 | −12% | 2% |
| | Terrene90 | 0.50 | 1.85 | −13% | −2% | 1.12 | −13% | −8% | 1.48 | −9% | 6% |
| | HS399 WB | 0.25 | 1.90 | −11% | 1% | 1.07 | −17% | −12% | 1.35 | −17% | −4% |
| | HS399 WB | 0.50 | 1.77 | −17% | −6% | 0.98 | −23% | −19% | 1.42 | −13% | 1% |
| | HS399 WB washed | 0.25 | 1.88 | −14% | −3% | 1.17 | −9% | −4% | 1.45 | −11% | 4% |
| | HS399 WB washed | 0.50 | 1.78 | −16% | −5% | 0.95 | −26% | −22% | 1.25 | −23% | −11% |
| | Combo 399WB | 0.25 | 1.78 | −16% | −5% | 0.93 | −27% | −23% | 1.30 | −20% | −7% |
| | Combo 399WB | 0.50 | 1.83 | −14% | −3% | 1.15 | −10% | −5% | 1.53 | −6% | 10% |

Application rates of the PHYCOTERRA® *Chlorella* microalgae composition, PT-O *Chlorella* microalgae composition pasteurized at 90° C., the *Aurantiochytrium acetophilum* HS399 whole biomass (WB) microalgae composition, the *Aurantiochytrium acetophilum* HS399 washed whole biomass (WB washed) microalgae composition, and the combination 25% *Chlorella*: 75% *Aurantiochytrium acetophilum* HS399 whole biomass (WB) microalgae composition were as detailed in Table 3 below.

TABLE 3

Treatments

| Treatment Number | Product | Application Rate gallon/acre |
| --- | --- | --- |
| T1 | Untreated control (UTC/standard practice) | N/A |
| T2 | Seaweed Commercial Reference | 0.5 |
| T3 | PHYCOTERRA® *Chlorella* composition | 0.25 |
| T4 | PHYCOTERRA® *Chlorella* composition | 0.5 |
| T5 | HS399 Whole Biomass (WB) washed | 0.25 |
| T6 | HS399 Whole Biomass (WB) washed | 0.5 |
| T7 | HS399 Whole Biomass (WB) | 0.25 |
| T8 | HS399 Whole Biomass (WB) | 0.5 |
| T9 | PT-O *Chlorella* composition pasteurized at 90° C. | 0.25 |
| T10 | PT-O *Chlorella* composition pasteurized at 90° C. | 0.5 |
| T11 | 25% *Chlorella*:75% H5399 WB | 0.25 |
| T12 | 25% *Chlorella*:75% H5399 WB | 0.5 |

Fifteen weeks after transplanting, berries were harvested and stored in cold storage for 5 days and weights before and after storage were compared. Water loss was fairly low for all water-holding capacity tests across treatments (<3% of original weight) but advantages were observed across the board. Berries from microalgae-treated plants lost 11-17% less water than the plants grown with standard practice and 2-6% less water than plants grown with standard practice and the seaweed commercial reference.

Figure 3:
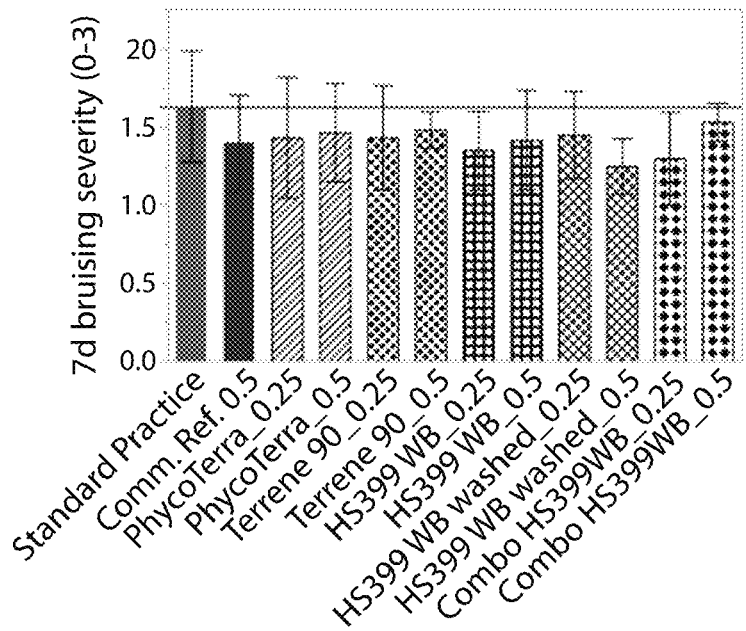
FIG. 3 is a graph showing a comparison of the effects of the several microalgae compositions of FIG. 1 on strawberry growth, yield, and post-harvest quality, wherein the effects are observed in a decrease in bruising of the strawberries after 7 days relative to the UTC and a seaweed commercial reference product.

Fifteen weeks after transplanting, berries were harvested and stored in cold storage for 5 or 7 days and bruising severity on the stored berries was compared between treatments. As shown in FIG. 2, berries from microalgae-treated plants had a lower degree of bruising (5-27% reduction) than from plants grown using standard practice. Berries assessed 5 days after storage showed an advantage for microalgae compositions compared to the seaweed commercial reference (5-23% reduction), but the same pattern was not consistent 7 days after storage (see FIG. 3).

Example 5

For the treatments referred to in this Example as Commercial Reference+PT-O65, the commercial reference was applied first to the soil at a rate of 20 gal/acre. The PT-O65 microalgae composition was then added on top via drip irrigation. The commercial reference was only applied 3 times per season, whereas the PT-O65 microalgae composition was applied every 14 days until harvest.

For the treatments referred to in this Example as Commercial Reference+PT-O90, the commercial reference was applied first to the soil at a rate of 20 gal/acre. The PT-O90 microalgae composition was then added on top via drip irrigation. The commercial reference was only applied 3 times per season, whereas the PT-O90 microalgae composition was applied every 14 days until harvest.

A trial was conducted on strawberry (var. portola—Organic) in Santa Maria, Calif. to evaluate performance of various microalgae compositions on strawberry growth, yield, and post-harvest berry quality, particularly PT-O65 microalgae composition, PT-O Chlorella pasteurized at 90° C. microalgae composition, the combination PT-O65 microalgae composition: microbial based commercial reference product microalgae composition, and the combination PT-O90 microalgae composition: microbial based commercial reference product microalgae composition. All plots received standard local fertigation practice, including NEPTUNE'S HARVEST fertilizer and NFORCE fertilizer. A control was added with standard local fertigation practice plus 4 applications of a microbial-based commercial reference product that is standard to this location. Treatments included two versions of an OMRI certified Chlorella microalgae composition that differ by pasteurization temperature (PT-O65 microalgae composition and PT-O90 microalgae composition), each tested alone and each tested in combination with the microbial-based commercial reference. Strawberry plants (frigo) were transplanted to the field in June 2017, according to local commercial practice. The first product application was via drip irrigation at the time of transplanting and then every 14 days afterward through to final harvest. The untreated control received the same amount of carrier water as other treatments at the time of each product application. The microalgae compositions were shaken well before application and agitated while in the chemigation tank in order to prevent solids from settling. Berries were harvested according to local commercial schedule (twice per week during fruiting season). The timing of the commercial reference applications was once at the time of planting (6/20), once 14-21 days after planting (7/5), once in late July/early August (7/31) and the last in early September (9/11). All plots were managed according to the local standard practice (see Study Parameters below).

| STUDY PARAMETERS | |
| --- | --- |
| Crop | Strawberry (var. *Portola*) |
| Location | Santa Maria, CA |
| Conventional Row Spacing | Wide 4-row beds, 64-inches center-to-center; plants spaced 14 inches apart in each of the four rows |
| Harvest Schedule | As frequently as standard local grower practice with estimated 32 picks |
| Fumigation Schedule | None (Organic) |
| Plot size minimum | 1 four-row bed 25-30 ft length per plot with 80+ plants per plot. Plots will be located away from any field edges with 1-2 commercial buffer beds in between |
| Trial Design | Randomized complete block |
| Observations | Yield data taken from 40 inside plants, outside 40 combined with inside 40 for post-harvest assessments |
| Replication | 6 replicate plots for each treatment and untreated control |
| Local Standard Production | Fertility, weed, insect management, etc. |
| Standard Management Practice | Standard management practices for organic production. Record disease management measures |

Application rates of PT-O65 microalgae composition, PT-O90 microalgae composition treatment, the combination Commercial Reference+PT-O65 microalgae composition treatment, and the combination Commercial Reference+PT-O90 microalgae composition treatment were as detailed in Table 4 below. Raw data is included in the table shown in Table 5.

TABLE 4

| | Treatments | |
| --- | --- | --- |
| Treatment Number | Product | Application Rate gallon/acre |
| T1 | Standard practice only (UTC) | Water |
| T2 | Commercial reference (No PT-O) | 20 |
| T3 | Commercial Reference + PT-O65 | 0.5 |
| T4 | Commercial Reference + PT-O90 | 0.5 |
| T5 | PT-O65 | 0.25 |
| T6 | PT-O90 | 0.25 |
| T7 | PT-O65 | 0.5 |
| T8 | PT-O90 | 0.5 |

TABLE 5

| Holding Test | Treatment | Rate (gal/A) | % Weight loss | % Advantage over Standard Practice | % Advantage over Comm. Ref. | % Marketable due to bruising level | % Advantage over Standard Practice | % Advantage over Comm. Ref. | % Severe bruising level | % Advantage over Standard Practice | % Advantage over Comm. Ref. |
|---|---|---|---|---|---|---|---|---|---|---|---|
| 1 | Standard practice | | −10.7% | | | 45.3% | | | 9.5% | | |
| | Comm Ref. | 20 | −8.7% | −19% | | 37.2% | −18% | | 15% | 55% | |
| | Comm Ref. + Terrene55 | 0.50 | −11.3% | 6% | 31% | 36.8% | −19% | −1% | 22% | 133% | 50% |
| | Comm Ref. + Terrene90 | 0.50 | −9.7% | −9% | 12% | 31.7% | −30% | −15% | 7% | −31% | −55% |
| | Terrene55 | 0.25 | −9.5% | −11% | 10% | 47.0% | 4% | 25% | 8% | −12% | −43% |
| | Terrene55 | 0.50 | −11.5% | 6% | 33% | 40.3% | −11% | 9% | 8% | −19% | −48% |
| | Terrene90 | 0.25 | −10.8% | 2% | 25% | 37.5% | −17% | 1% | 7% | −22% | −50% |
| | Terrene90 | 0.50 | −10.8% | 2% | 25% | 49.3% | 9% | 33% | 11% | 19% | −23% |
| 2 | Standard practice | | −2.7% | | | 85.2% | | | 12% | | |
| | Comm Ref. | 20 | −5.4% | 103% | | 77.8% | −9% | | 14% | 18% | |
| | Comm Ref. + Terrene55 | 0.50 | −1.7% | −38% | −69% | 94.2% | 11% | 21% | 4% | −68% | −73% |
| | Comm Ref. + Terrene90 | 0.50 | −1.7% | −38% | −69% | 63.0% | −3% | 7% | 10% | −10% | −24% |
| | Terrene55 | 0.25 | −2.5% | −6% | −54% | 86.3% | 1% | 11% | 10% | −10% | −24% |
| | Terrene55 | 0.50 | −2.0% | −25% | −63% | 81.7% | −4% | 5% | 15% | 38% | 17% |
| | Terrene90 | 0.25 | −3.2% | 19% | −41% | 86.8% | 2% | 12% | 11% | −3% | −18% |
| | Terrene90 | 0.50 | −1.5% | −44% | −72% | 89.3% | 5% | 15% | 9% | −21% | −33% |
| 3 | Standard practice | | −20.0% | | | 39.5% | | | 36% | | |
| | Comm Ref. | 20 | −25.7% | 28% | | 50.7% | 28% | | 32% | −10% | |
| | Comm Ref. + Terrene55 | 0.50 | −22.8% | 14% | −11% | 55.3% | 40% | 9% | 34% | −3% | 6% |
| | Comm Ref. + Terrene90 | 0.50 | −18.3% | −8% | −29% | 38.3% | −3% | −24% | 45% | 27% | 42% |
| | Terrene55 | 0.25 | −26.2% | 31% | 2% | 42.7% | 8% | −16% | 36% | 3% | 14% |
| | Terrene55 | 0.50 | −20.8% | 4% | −19% | 50.7% | 28% | 0% | 35% | −1% | 10% |
| | Terrene90 | 0.25 | −25.0% | 25% | −3% | 43.0% | 9% | −15% | 42% | 17% | 31% |
| | Terrene90 | 0.50 | −19.8% | −1% | −23% | 42.3% | 7% | −15% | 40% | 12% | 25% |

TABLE 5-continued

Raw Data

| Holding Test | Treatment | Firmness (g force) | % Advantage over Standard Practice | % Advantage over Comm. Ref. | Overall | Appearance | Aroma | Flavor | Texture |
|---|---|---|---|---|---|---|---|---|---|
| 1 | Standard practice | 546.7 | | | | | | | |
| | Comm Ref. | 540.7 | −1% | | | | | | |
| | Comm Ref. + Terrene55 | 548.4 | 0% | 1% | | | | | |
| | Comm Ref. + Terrene90 | 595.4 | 9% | 10% | | | | | |
| | Terrene55 | 505.1 | −8% | −7% | | | | | |
| | Terrene55 | 526.3 | −4% | −3% | | | | | |
| | Terrene90 | 562.1 | 3% | 4% | | | | | |
| | Terrene90 | 532.0 | −3% | −2% | | | | | |
| 2 | Standard practice | 943.7 | | | 6.9 | 6.1 | 6.2 | 5.7 | 6.5 |
| | Comm Ref. | 918.3 | −3% | | 7.1 | 6.4 | 6.5 | 6.2 | 6.7 |
| | Comm Ref. + Terrene55 | 1005.4 | 7% | 9% | 6.7 | 5.9 | 6.2 | 5.8 | 6.6 |
| | Comm Ref. + Terrene90 | 976.0 | 4% | 6% | | | | | |
| | Terrene55 | 968.3 | 3% | 5% | 6.6 | 5.7 | 5.8 | 5.5 | 6.5 |
| | Terrene55 | 1000.3 | 6% | 9% | 6.8 | 6.5 | 6.2 | 6.2 | 6.6 |
| | Terrene90 | 1046.6 | 11% | 14% | | | | | |
| | Terrene90 | 946.5 | 1% | 3% | | | | | |
| 3 | Standard practice | 1204.3 | | | | | | | |
| | Comm Ref. | 1234.4 | 3% | | | | | | |
| | Comm Ref. + Terrene55 | 1100.2 | −9% | −11% | | | | | |
| | Comm Ref. + Terrene90 | 1253.5 | 4% | 2% | | | | | |
| | Terrene55 | 1193.7 | −1% | −3% | | | | | |

TABLE 5-continued

Raw Data

| Holding Test | Treatment | Rate (gal/A) | % Weight loss | % Advantage over Standard Practice | % Advantage over Comm. Ref. | % Marketable due to bruising level | % Advantage over Standard Practice | % Advantage over Comm. Ref. | % Severe bruising level | % Advantage over Standard Practice | % Advantage over Comm. Ref. |
|---|---|---|---|---|---|---|---|---|---|---|---|
| | Terrene55 | | 1212.5 | 1% | −2% | | | | | | |
| | Terrene90 | | 1221.5 | 1% | −1% | | | | | | |
| | Terrene90 | | 1205.2 | 0% | −2% | | | | | | |

At 11, 14 and 18 weeks after transplanting, berries were harvested and stored in cold storage for 6 days and weights before and after storage were compared. Percent weight (water) loss is shown for all 3 assessments. Across all 3 assessments, berries from plants treated with a combination of Commercial Reference+PT-O90 microalgae composition lost 8-38% less water than those treated with standard practice. Berries from plants treated with PT-O90 microalgae composition lost 6-11% less water than standard practice for the first two assessments. Almost all treatments had a positive effect over standard practice for the 2$^{nd}$ assessment. For the last two assessments, almost all treatments had an advantage over the commercial reference alone (3-70%). Overall, PT-O65 microalgae composition and PT-O90 microalgae composition at 0.5 gal/A alone and combined with the commercial reference showed the most advantage in Santa Maria.

At 11, 14 and 18 weeks after transplanting, berries were harvested and stored in cold storage for 6 days and berry skin firmness was assessed using a penetrometer. The force needed to pierce the skin (g force) is shown below for all 3 assessments performed on Santa Maria berries. Across all 3 assessments, berries from plants treated with a combination of the microbial-based Commercial Reference+PT-O90 microalgae composition were 4-9% firmer after storage than those treated with standard practice and 2-10% firmer than those receiving just the commercial reference. PT-O90 microalgae composition (¼ gal/A) showed an advantage over standard practice (3-11%) and the commercial reference (4-14%) in 2 of the 3 assessments.

At 11, 14 and 18 weeks after transplanting, berries were harvested and stored in cold storage for 6 days and bruising was assessed at the end of this period. Marketability (% of berries with mild to moderate bruising) is shown for all 3 assessments performed on Santa Maria berries. In all 3 assessments, PT-O90 microalgae composition (½ gal/A) showed an increase in marketability due to reduced bruising compared to standard practice (5-9%). The microbial-based Commercial Reference+PT-O65 microalgae composition (½ gal/A; 11-40%), PT-O65 microalgae composition alone (¼ gal/A; 4-8%), and PT-O90 microalgae composition alone (¼ gal/A, 2-9%) all showed an advantage over standard practice in 2 of 3 assessments. Compared to the commercial reference alone, PT-O65 microalgae composition and PT-O90 microalgae composition showed an advantage increasing marketability in 2 of 3 assessments (5-30%).

The percent of berries with severe bruising was evaluated. Compared to standard practice, PT-O65 microalgae composition (¼ gal/A) and the combination of the Commercial Reference+PT-O90 microalgae composition reduced severe bruising (10-30%) in 2 of 3 assessments. Compared to the commercial reference, multiple treatments showed a benefit.

For the consumer preference testing, one harvest was performed for each trial. The first occurred on or about Oct. 11, 2017. Marketable berries from 6 replicates each of 6 treatments were harvested and packaged into clamshells. These were delivered to the University sensory lab the same day. The second harvest occurred on or about Nov. 2, 2017. Marketable berries from 6 replicates each of 5 treatments were harvested and packaged into clamshells. Once shipment was received, a consumer taste panel was conducted. Berries were washed and prepared into halves for approximately 100 consumer volunteers who received one half of 5-6 berries (UTC and 4-5 treatments). Berries were scored for appearance and flavor. It should be noted that for the consumer sensory panel testing, the treatments were as shown below in Table 6.

TABLE 6

Treatments

| Treatment Number | Product | Application Rate gallon/acre |
|---|---|---|
| T1 | Standard practice only (UTC) | Water |
| T2 | Commercial reference (No PT-O) | 20 |
| T3 | Commercial Reference + PT-O65 | 0.5 |
| T5 | PT-O65 | 0.25 |
| T7 | PT-O65 | 0.5 |

Twelve weeks after transplanting, berries were harvested and transported to a University sensory lab where they were kept overnight at 4° C. The next day they were assessed by 102 respondents for various liking attributes. PT-O65 microalgae composition applied at ½ gal/A was preferred over standard practice for overall liking and flavor liking and generally performed similarly to the microbial-based commercial reference. The commercial reference was preferred over standard practice for all attributes.

Example 6

A trial was conducted on strawberry (var. *portola*) in Oxnard, Calif. to evaluate performance of various microalgae compositions on strawberry growth, yield, and post-harvest berry quality; particularly, the PHYCOTERRA®

*Chlorella* microalgae composition, PT-O65 microalgae composition, the *Aurantiochytrium acetophilum* HS399 whole biomass (WB) microalgae composition, the *Aurantiochytrium acetophilum* HS399 extracted biomass (EB) microalgae composition, and the combination 25% *Chlorella:* 75% HS399 whole biomass (WB) microalgae composition. All plots receive standard local fertilization regimen used by the grower for this crop, excluding biostimulants. The microalgae compositions were added in addition to standard fertilization. Strawberry plants were transplanted to the field in July 2017, according to local commercial practice. The first product application was via drip irrigation at the time of transplanting and then every 14 days afterward through to final harvest. The untreated control received the same amount of carrier water as other treatments at the time of each product application. The microalgae compositions were shaken well before application and agitated, if possible, while in the chemigation tank to prevent solids from settling. Berries were harvested according to local commercial schedule (twice per week during the fruiting season). All plots were managed according to the local standard practice (see Study Parameters below).

| STUDY PARAMETERS | |
| --- | --- |
| Crop | Strawberry (var. *Portola*) |
| Location | Oxnard, CA |
| Conventional Row Spacing | Wide 4-row beds, 64-inches center-to-center; plants spaced 14 inches apart in each of the four rows |
| Harvest Schedule | As frequently as standard local grower practice with estimated 24 picks |
| Fumigation Schedule | Local practice (recorded)-timing will be in June |
| Plot size minimum | 1 four-row bed 25 ft length per plot with 80+ plants per plot. Plots will be located away from any field edges with 1-2 commercial buffer beds in between |
| Trial Design | Randomized complete block |
| Observations | Yield data taken from 40 inside plants, outside 40 combined with inside 40 for post-harvest assessments |
| Replication | 6 replicate plots for each treatment and untreated control |
| Local Standard Production | Fertility, weed, insect management, etc |
| Standard Management Practice | Standard management practices, including fungicide application. Record disease management measures. Fungicides will be applied as necessary (by grower) when flowers and fruit are present |

Application rates of the PHYCOTERRA® *Chlorella* microalgae composition, the *Aurantiochytrium acetophilum* HS399 extracted biomass (EB) microalgae composition, the *Aurantiochytrium acetophilum* HS399 whole biomass (WB) microalgae composition, PT-O65 microalgae composition, and the combination 25% *Chlorella:* 75% HS399 whole biomass (WB) microalgae composition were as detailed in Table 7 below.

TABLE 7

| Treatments | | |
| --- | --- | --- |
| Treatment Number | Product | Application Rate gallon/acre |
| T1 | Untreated control (UTC/standard practice) | Water |
| T2 | Seaweed Commercial Reference | 0.5 |
| T3 | PHYCOTERRA ® *Chlorella* composition | 0.25 |
| T4 | PHYCOTERRA ® *Chlorella* composition | 0.5 |
| T5 | HS399 Extracted Biomass (EB) | 0.25 |
| T6 | HS399 Extracted Biomass (EB) | 0.5 |
| T7 | HS399 Whole Biomass (WB) | 0.25 |
| T8 | HS399 Whole Biomass (WB) | 0.5 |
| T9 | PT-O65 | 0.25 |
| T10 | PT-O65 | 0.5 |
| T11 | 25% *Chlorella*:75% HS399 WB | 0.25 |
| T12 | 25% *Chlorella*:75% HS399 WB | 0.5 |

At 11, 15, 19, 21, and 26 weeks after transplanting, berries were harvested and stored in cold storage for 6 to 10 days and weights before and after storage were compared. Water loss was fairly low for all holding tests across treatments (<13% of original weight) but some advantages were observed. Compared to standard practice, PT-O65 microalgae composition (¼ gal/A) and *Aurantiochytrium acetophilum* HS399 whole biomass (WB) microalgae composition (½ gal/A) showed advantage in 4 of 5 assessments (4-41%); the seaweed-based commercial reference, the PHYCOTERRA® *Chlorella* microalgae composition, and the *Aurantiochytrium acetophilum* HS399 extracted biomass (EB) microalgae composition showed an advantage in 3 of 5 assessments. Compared to the commercial reference, only the *Aurantiochytrium acetophilum* HS399 extracted biomass (EB) microalgae composition (½ gal/A) showed an advantage for reducing water loss of stored berries (13-20% in 3 of 5 assessments).

At 11, 15, 19, 21 and 26 weeks after transplanting, berries were harvested and stored in cold storage for 6 to 10 days and berry skin firmness was assessed using a penetrometer. The force needed to pierce the skin (g force) was evaluated for all 5 assessments performed on the Oxnard strawberries. In 2 of 5 assessments, PT-O65 microalgae composition, *Aurantiochytrium acetophilum* HS399 extracted biomass (EB) microalgae composition (¼ gal/A), *Aurantiochytrium acetophilum* HS399 whole biomass (WB) microalgae composition, and the combination 25% *Chlorella:* 75% HS399 whole biomass (WB) microalgae composition all showed an advantage in skin firmness (4-20%) compared to standard practice. These advantages occurred during the extreme ends of the harvest season (September and January) when berries may be off-peak and increasing shelf-life advantage would be most desirable. Compared to the seaweed-based commercial reference, the PHYCOTERRA® *Chlorella* microalgae composition and the *Aurantiochytrium acetophilum* HS399 extracted biomass (EB) microalgae composition showed an advantage in 3 of 5 assessments (4-14%).

At 11, 15, 19, 21 and 26 weeks after transplanting, berries were harvested and stored in cold storage for 6-10 days and bruising was assessed at the end of this period. Marketability (% of berries with mild to moderate bruising) was evaluated for all 4 assessments performed on Oxnard strawberries. Compared to standard practice, improvements were only observed for the final two assessments (late season). PT-O65 microalgae composition (6-18%) and the *Aurantiochytrium acetophilum* HS399 extracted biomass (EB) microalgae composition (3-20%) showed increased marketability due to bruising reduction in both assessments. Improvements over the seaweed commercial reference were only observed in the first and last assessment (early and late season). All microalgae compositions showed an advantage over the commercial reference for the first assessment (2-20%) and for the late season final assessment of PHYCOTERRA® *Chlorella* microalgae composition (0.25 gal/A), PT-O65 microalgae composition (0.25 gal/A), and both rates of *Aurantiochytrium acetophilum* HS399 extracted biomass (EB) microalgae composition (6-11%). The percent of berries with severe bruising was especially reduced during late season by multiple products (10-60%).

For the consumer preference testing, one harvest was performed for each trial. The first occurred on or about Oct. 11, 2017. Marketable berries from 6 replicates each of 6 treatments were harvested and packaged into clamshells. These were delivered to the University sensory lab the same day. The second harvest occurred on or about Nov. 2, 2017. Marketable berries from 6 replicates each of 5 treatments were harvested and packaged into clamshells. Once shipment was received, a consumer taste panel was conducted. Berries were washed and prepared into halves for approximately 100 consumer volunteers who received one half of 5-6 berries (UTC and 4-5 treatments). Berries were scored for appearance and flavor. It should be noted that for the consumer sensory panel testing, the treatments were as shown below in Table 8.

TABLE 8

Treatments

| Treatment Number | Product | Application Rate gallon/acre |
|---|---|---|
| T1 | Standard practice only (UTC) | Water |
| T2 | Seaweed Commercial Reference | 0.5 |
| T4 | PHYCOTERRA ® *Chlorella* composition | 0.5 |
| T6 | HS399 Extracted Biomass (EB) | 0.5 |
| T8 | HS399 Whole Biomass (WB) | 0.5 |
| T10 | PT-O65 | 0.5 |

Sixteen weeks after transplanting, berries were harvested and transported to a university sensory lab where they were kept overnight at 4° C. The next day they were assessed by 100 respondents for various liking attributes. All treatments were tested at the ½ gallon/A rate. The *Aurantiochytrium acetophilum* HS399 whole biomass (WB) microalgae composition was preferred over standard practice and the seaweed-based commercial reference for all attributes. This treatment particularly stood out for overall liking, aroma and flavor. The PHYCOTERRA® *Chlorella* composition was also preferred over standard practice for all attributes but not to the same degree as the *Aurantiochytrium acetophilum* HS399 whole biomass (WB) microalgae composition. PT-O65 microalgae composition was only preferred over standard practice for appearance and was preferred less for overall liking, aroma and flavor.

Example 7

Many products advertised as "Christmas tree preservatives" are sold at nurseries and garden centers where Christmas trees are sold during the Winter holiday season. Advertising claims for tree preservatives usually state that the products reduce "needle (leaf) drop" and preserve the freshness of cut Christmas trees. These products vary wildly in composition and often do not list active ingredients on labels. PT-O *Chlorella* microalgae composition was evaluated against an untreated control and a commercial reference product for its potential to preserve the quality of cut Christmas trees.

Sixteen Douglass Fir trees (6'-7') were purchased from a local retail garden center within one hour of delivery from wholesaler. The 16 trees were divided into two groups of eight, a "fresh tree" group and "stored tree" group. The fresh tree group was used to populate one half of the experiment on the same day they were purchased. The stored tree group were kept in a warehouse for two weeks, to simulate unfavorable real-world storage conditions found in retail centers. After the storage period, the stored trees were set up alongside the fresh tree group and treated. Within both of the two groups four unique treatments were applied to two replicates.

Trees were installed in plastic tree stands with approximately 4' spacing between each tree. The experiment was conducted in a climate-controlled warehouse space. A square perimeter was established around each tree to designate the collection zone for fallen needles. At initial setup, each stand was filled with 1.5 L of solution (maximum volume after displacement from tree trunk).

PT-O *Chlorella* microalgae composition was applied at 0.1%, 1.0% and 5.0% (vol/vol). A commercial reference (CR) product was also applied at 1.0% vol/vol, as listed on the product label. Reapplication of each treatment solution occurred when the untreated control trees had consumed nearly all water in the tree stand. The volume of each solution required to top-off the reservoir was quantified and tracked over time.

Fallen needles were collected from the floor under each tree periodically. Needles were placed in paper bags (separate for each replicate) and dried in a dehydrator at 160° F. for at least one week before weighing. Three collections occurred for the fresh tree group and two for the stored tree group. Tree height (ft) and trunk circumference (ft) were measured at the end of the experiment.

The cumulative needle drop weight for each treatment was compared in three ways: raw weight values, normalized by height and normalized by circumference are shown below in Table 9. Normalization by height and circumference did not affect the patterns between treatments. Needle drop weight per treatment was also examined as a function of time (see Table 10 below).

TABLE 9

Average Cumulative Needle Dry Weight

| Block | Treatment | Ave. Needle Drop Dry Weight (cumulative, g) | Ave. Height (ft) | Ave. Height-corrected cumulative needle weight (g/ft) | Ave. Circumference (ft) | Ave. Circumference-corrected cumulative needle weight (g/ft) |
|---|---|---|---|---|---|---|
| Fresh trees | Untreated | 51.705 | 6.58 | 7.89 | 0.81 | 62.79 |
| Fresh trees | Commercial Reference 1.0% | 23.99 | 7.23 | 3.28 | 0.72 | 32.89 |
| Fresh trees | PT-O 1.0% | 31.435 | 7.13 | 4.46 | 0.88 | 37.88 |
| Fresh trees | PT-O 5.0% | 14.89 | 6.77 | 2.23 | 0.65 | 23.75 |
| Stored trees | Untreated | 10.3 | 6.92 | 1.49 | 0.76 | 14.18 |
| Stored trees | Commercial Reference 1.0% | 12.965 | 6.54 | 1.98 | 0.70 | 18.55 |
| Stored trees | PT-O 0.1% | 14.2 | 6.75 | 2.10 | 0.80 | 17.62 |
| Stored trees | PT-O 1.0% | 26.02 | 6.60 | 3.94 | 0.96 | 27.24 |

TABLE 10

Average Needle Drop Dry Weight (g) by Treatment Over Time

| Date | Block | Treatment | Average Needle Dry Weight (g) | Cumulative Needle Dry Weight (g) |
|---|---|---|---|---|
| Dec. 7, 2017 | Fresh | Untreated | 17.265 | 51.7 |
| Dec. 7, 2017 | Fresh | Commercial Reference 1.0% | 12.825 | 24.0 |
| Dec. 7, 2017 | Fresh | PT-O 1.0% | 13.285 | 31.4 |
| Dec. 7, 2017 | Fresh | PT-O 5.0% | 7.935 | 14.9 |
| Dec. 13, 2017 | Fresh | Untreated | 9.15 | |
| Dec. 13, 2017 | Fresh | Commercial Reference 1.0% | 4.7 | |
| Dec. 13, 2017 | Fresh | PT-O 1.0% | 5.685 | |
| Dec. 13, 2017 | Fresh | PT-O 5.0% | 2.27 | |
| Jan. 5, 2018 | Fresh | Untreated | 25.29 | |
| Jan. 5, 2018 | Fresh | Commercial Reference 1.0% | 6.465 | |
| Jan. 5, 2018 | Fresh | PT-O 1.0% | 12.465 | |
| Jan. 5, 2018 | Fresh | PT-O 5.0% | 4.685 | |
| Dec. 13, 2017 | Stored | Untreated | 6.025 | 10.8 |
| Dec. 13, 2017 | Stored | Commercial Reference 1.0% | 5.98 | 12.88 |
| Dec. 13, 2017 | Stored | PT-O 0.1% | 9.39 | 14.2 |
| Dec. 13, 2017 | Stored | PT-O 1.0% | 14.99 | 26.02 |
| Jan. 5, 2018 | Stored | Untreated | 4.275 | |
| Jan. 5, 2018 | Stored | Commercial Reference 1.0% | 6.985 | |
| Jan. 5, 2018 | Stored | PT-O 0.1% | 4.81 | |
| Jan. 5, 2018 | Stored | PT-O 1.0% | 11.03 | |

Figure 4:
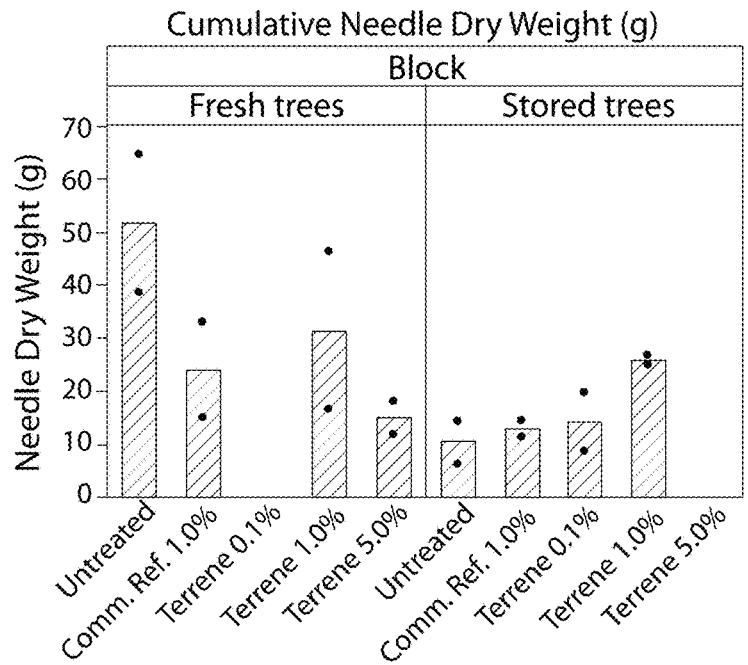
FIG. 4 is a graph showing the effects of a microalgae composition on Douglas fir tree preservation, wherein the effects are observed in a decrease in fallen needles relative to the UTC and a commercial reference product.

As shown in FIG. 4, within the fresh tree group, both PT-O *Chlorella* microalgae composition and the commercial reference reduced the total weight of fallen needles by 70% across 3 collection dates. However, this same pattern did not hold true for trees in the stored tree block.

The volume of each solution required to top-off the reservoir of each tree varied between treatments and the actual volumes applied were recorded (see Table 11 below).

The average volume across all top-off events was evaluated. Only data for the fresh trees block was recorded. For 4 of 6 different top-off events, the trees treated with PT-O *Chlorella* microalgae composition at 5% required 11-60% less water than untreated control. Results were more variable compared to the commercial reference but ranged from 5-40% less water in 3 of 6 top off events.

TABLE 11

Volumes of Treatment Solution (mL) to Replenish Individual Tree-Watering Reservoirs

| Date | Block | Treatment | Average Top-off Volume (mL) |
|---|---|---|---|
| Nov. 27, 2017 | Fresh | Untreated | 1500 |
| Nov. 27, 2017 | Fresh | Commercial Reference 1.0% | 1500 |
| Nov. 27, 2017 | Fresh | PT-O 1.0% | 1500 |
| Nov. 27, 2017 | Fresh | PT-O 5.0% | 1500 |
| Nov. 29, 2017 | Fresh | Untreated | 1200 |
| Nov. 29, 2017 | Fresh | Commercial Reference 1.0% | 650 |
| Nov. 29, 2017 | Fresh | PT-O 1.0% | 1150 |
| Nov. 29, 2017 | Fresh | PT-O 5.0% | 950 |
| Dec. 3, 2017 | Fresh | Untreated | 900 |
| Dec. 3, 2017 | Fresh | Commercial Reference 1.0% | 800 |
| Dec. 3, 2017 | Fresh | PT-O 1.0% | 1100 |
| Dec. 3, 2017 | Fresh | PT-O 5.0% | 800 |
| Dec. 7, 2017 | Fresh | Untreated | 650 |
| Dec. 7, 2017 | Fresh | Commercial Reference 1.0% | 450 |
| Dec. 7, 2017 | Fresh | PT-O 1.0% | 475 |
| Dec. 7, 2017 | Fresh | PT-O 5.0% | 375 |
| Dec. 13, 2017 | Fresh | Untreated | 1100 |
| Dec. 13, 2017 | Fresh | Commercial Reference 1.0% | 750 |
| Dec. 13, 2017 | Fresh | PT-O 1.0% | 600 |
| Dec. 13, 2017 | Fresh | PT-O 5.0% | 450 |
| Dec. 20, 2017 | Fresh | Untreated | 950 |
| Dec. 20, 2017 | Fresh | Commercial Reference 1.0% | 1100 |
| Dec. 20, 2017 | Fresh | PT-O 1.0% | 800 |
| Dec. 20, 2017 | Fresh | PT-O 5.0% | 1050 |

Overall, the trees treated with PT-O *Chlorella* microalgae composition at 5% lost fewer needles and required less water during the month after trees were cut and set up in tree stands.

Increased Fruit Sweetness

Example 8

"Degrees Brix" or "Brix" is a metric that is used in the food industry for measuring the approximate amount of sugars in fruits, vegetables, juices, soft drinks, wine, and in the starch and sugar manufacturing industry. Brix usually refers to a scale of measurement for total dissolved solids in the juice of the fruit or vegetable, wherein the dissolved solids are usually sugars and the Brix measurement approximates the sugar content of a sample.

Fruiting plants, as described herein, include any plant that produces a fruit; i.e. the fleshy or dry ripened ovary of the plant which encloses the seed or seeds.

A trial was conducted on strawberry (var. *camarosa*) in Winter Garden, Fla. to evaluate performance of the PHY-COTERRA® *Chlorella* microalgae composition and the *Aurantiochytrium acetophilum* HS399 extracted biomass (EB) microalgae composition on berry quality after storage, on consumer preference, and sweetness. The trail as transplanted in late October 2016 and harvested through early March 2017. All plots were managed according to the local standard practice (see Study Parameters below).

STUDY PARAMETERS

| | |
|---|---|
| Crop | Strawberry (var. *Camarosa*) |
| Location | Winter Garden, FL |
| Transplanting Date | Oct. 24, 2016 |
| Pick Frequency | Weekly culls when not assessed |
| Bed dimensions | 60" W × 6" H, 2 rows |
| Planting density | 17,424 plants/A |
| Drip irrigation | 6" emitters, 0.3" applied daily |
| Fertilizer | 20-100 lbs 20-20-20 NPK monthly via drip |
| Pesticide | Ridomil, Sevin, Dipel and Captec as needed |
| Soil Type | Sandy, non-fumigated |
| Plot Size | 12 ft sections of 100 ft bed |
| Replication | 4 |
| Product applied | 0.5 gal/A via drip at planting then every 2 wks |

All plots received the standard fertilization regimen used by the grower for these crops excluding biostimulants. The microalgae compositions were added in addition to standard fertilization. Strawberry plants were transplanted to the field. The first product application was at the time of transplanting and then every 14 days afterward until harvest via drip irrigation. The untreated control received the same amount of carrier water as other treatments at the time of each application. Products were shaken well before application and agitated while in the chemigation tank to prevent solids from settling.

Berries from one harvest (day 113) were harvested and either kept in cold storage onsite or shipped cold overnight to a University in New York where they were kept in cold storage. After a period of 4 days in storage, at both sites, the berries were assessed for post-storage quality, particularly sweetness.

Application rates of the PHYCOTERRA® *Chlorella* microalgae composition and the *Aurantiochytrium acetophilum* HS399 extracted biomass (EB) microalgae composition were as detailed in Table 12 below. Raw data is shown in Table 13 below.

TABLE 12

Treatments

| Treatment Number | Product | Application Rate gallon/acre |
|---|---|---|
| T1 | Standard Practice (Untreated) | N/A |
| T2 | PHYCOTERRA ® composition | 0.4 |
| T3 | PHYCOTERRA ® composition | 0.5 |
| T4 | PHYCOTERRA ® composition | 1 |
| T5 | PHYCOTERRA ® composition | 2 |
| T6 | HS399 Extracted Biomass (EB) | 0.4 |
| T7 | HS399 Extracted Biomass (EB) | 0.5 |
| T8 | HS399 Extracted Biomass (EB) | 1 |
| T9 | HS399 Extracted Biomass (EB) | 2 |
| T10 | Green Water Polyculture | 0.4 |
| T11 | Green Water Polyculture | 0.5 |
| T12 | Green Water Polyculture | 1 |
| T13 | Green Water Polyculture | 2 |
| T14 | Seaweed-based Commercial Reference | 0.5 |

TABLE 13

Raw Data

| Treatment | Rate (gal/A) | % Brix post-storage 38F | % Advantage over Standard Practice | % Advantage over Comm. Ref. | % Brix post-shipping storage 34F | % Advantage over Standard Practice | % Advantage over Comm. Ref. |
|---|---|---|---|---|---|---|---|
| Standard practice | | 7.13 | | | 7.30 | | |
| Comm. Ref. | 0.5 | 7.97 | 12% | | 9.13 | 25% | |
| PhycoTerra | 0.4 | 7.87 | 10% | −1% | 8.98 | 23% | −2% |
| PhycoTerra | 0.5 | 8.70 | 22% | 9% | 8.83 | 21% | −3% |
| PhycoTerra | 1 | 8.20 | 15% | 3% | 8.90 | 22% | −2% |
| PhycoTerra | 2 | 8.33 | 17% | 5% | 9.40 | 29% | 3% |
| HS399 EB | 0.4 | 8.05 | 13% | 1% | 9.65 | 32% | 6% |
| HS399 EB | 0.5 | 7.70 | 8% | −3% | 8.63 | 18% | −5% |
| HS399 EB | 1 | 8.03 | 13% | 1% | 9.05 | 24% | −1% |
| HS399 EB | 2 | 7.83 | 10% | −2% | 9.38 | 28% | 3% |
| GWP | 0.4 | 7.38 | 3% | −7% | 8.65 | 18% | −5% |
| GWP | 0.5 | 7.70 | 8% | −3% | 9.40 | 29% | 3% |
| GWP | 1 | 7.55 | 6% | −5% | 8.8 | 11% | −12% |
| GWP | 2 | 7.45 | 4% | −6% | 8.50 | 16% | −7% |

Figure 5:
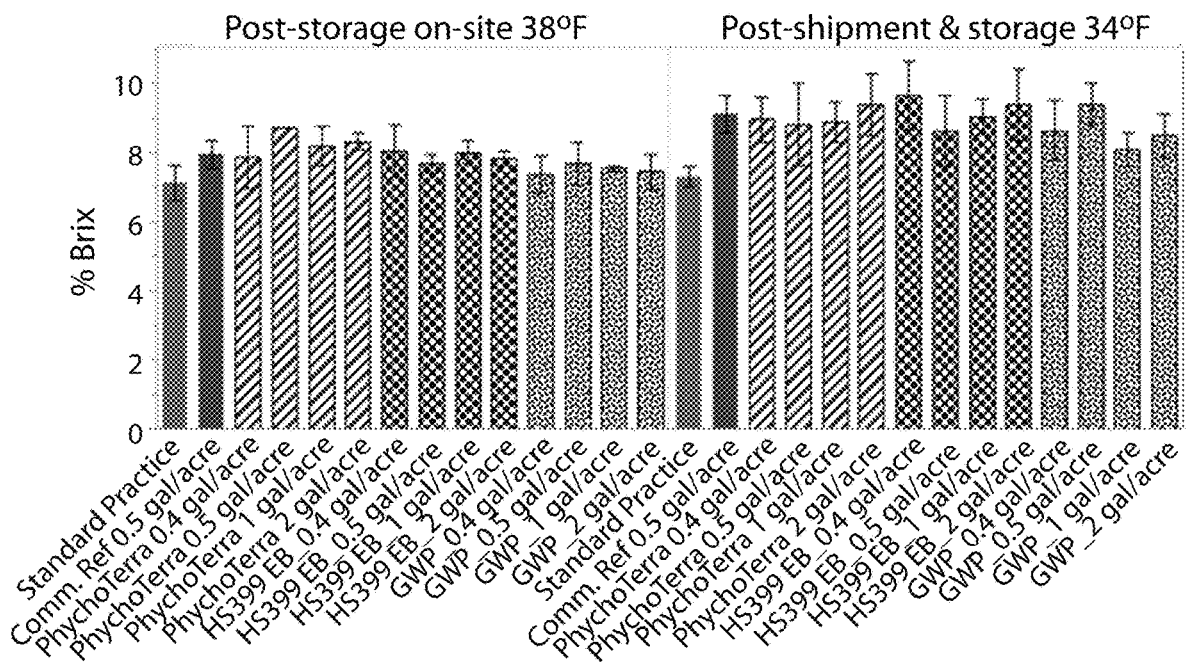
FIG. 5 is a graph showing a comparison of the effects of two microalgae compositions on strawberry quality, wherein the effects are observed in an increase in strawberry sweetness (% brix) relative to the UTC and a seaweed commercial reference product.

As shown in FIG. 5, relative to standard practice alone (UTC), bi-weekly additions of the PHYCOTERRA® *Chlorella* microalgae composition at 0.5 gal/A improved berry sweetness (% brix) after shipping and cold storage. For both conditions (38° F. and 34° F. storage), all treatments were sweeter than standard practice (3-32%). PHYCOTERRA® *Chlorella* microalgae composition at 0.5 gal/A and 2 gal/A showed some of the highest improvements over commercial practice (22-29%). Compared to the seaweed-based commercial reference, PHYCOTERRA® *Chlorella* microalgae composition at 2 gal/A was 3-5% better for both conditions. The *Aurantiochytrium acetophilum* HS399 extracted biomass (EB) microalgae composition, at all rates, was at least 18% sweeter than standard practice after shipping and storage.

Example 9

A trial was conducted on strawberry (var. Seascape) in Fresno, Calif. to evaluate performance of various microalgae compositions on strawberry growth, yield, and post-harvest berry quality, and sweetness; particularly PHYCOTERRA® *Chlorella* microalgae composition, PT-O65 microalgae composition, the *Aurantiochytrium acetophilum* HS399 whole biomass (WB) microalgae composition, the *Aurantiochytrium acetophilum* HS399 extracted biomass (EB) microalgae composition, the combination 25% *Chlorella*: 75% HS399 whole biomass (WB) microalgae composition, and the combination 25% *Chlorella*: 75% HS399 extracted biomass (EB) microalgae composition. All plots received the standard local fertilization regimen used by the grower for this crop, excluding biostimulants. The microalgae compositions were added in addition to standard fertilization. Strawberry plants were transplanted to the field in mid-August 2017, according to local commercial practice. The first product application was via drip irrigation at the time of transplanting and then every 14 days afterward through to final harvest. The untreated control received the same amount of carrier water as other treatments at the time of each product application. Products were shaken well before application and agitated, if possible, while in the chemigation tank to prevent solids from settling. Berries were harvested according to local commercial schedule (twice per week during fruiting season). All plots were managed according to the local standard practice (see Study Parameters below).

| STUDY PARAMETERS | |
|---|---|
| Crop | Strawberry (var. Seascape) |
| Location | Fresno, CA |
| Row Spacing | Conventional |
| Harvest Schedule | 4 harvests will be quantified between Sept-Nov. Weekly picks will be performed otherwise and berries discarded to minimize amount of rotten fruit on plants |
| Fumigation Schedule | Non-fumigated |
| Plot size minimum | 12 ft section after first 2 ft along 76 ft drip line |
| Observations | Taken from multiple subsamples per 12 ft section |
| Replication | 6 replicate plots for each treatment and untreated control |
| Local Standard Production | Fertility, weed, insect management, etc. |
| Standard Management Practice | Fungicide application. Record disease management measures |

Application rates of the PHYCOTERRA® *Chlorella* microalgae composition, the *Aurantiochytrium acetophilum* HS399 whole biomass (WB) microalgae composition, the *Aurantiochytrium acetophilum* HS399 extracted biomass (EB) microalgae composition, PT-O65 microalgae composition, the combination 25% *Chlorella*: 75% HS399 whole biomass (WB) microalgae composition, and the combination 25% *Chlorella*: 75% HS399 extracted biomass (EB) microalgae composition were as detailed in Table 14 below. Raw data is included in the table shown in FIG. 6.

TABLE 14

Treatments

| Treatment Number | Product | Application Rate gallon/acre |
|---|---|---|
| T1a | Untreated control (UTC/standard practice) | Water |
| T1b | Untreated control (UTC/standard practice) | Water |
| T2 | Seaweed Commercial Reference | 0.5 |
| T3 | PHYCOTERRA ® | 0.25 |
| T4 | PHYCOTERRA ® | 0.5 |
| T5 | HS399 Whole Biomass (WB) | 0.25 |
| T6 | HS399 Whole Biomass (WB) | 0.5 |
| T7 | HS399 Extracted Biomass (EB) | 0.25 |
| T8 | HS399 Extracted Biomass (EB) | 0.5 |
| T9 | PT-O65 | 0.25 |
| T10 | PT-O65 | 0.5 |
| T11 | 25% *Chlorella*: 75% HS399 WB | 0.25 |
| T12 | 25% *Chlorella*: 75% HS399 WB | 0.5 |
| T13 | 25% *Chlorella*: 75% HS399 EB | 0.25 |
| T14 | 25% *Chlorella*: 75% HS399 EB | 0.5 |
| T15 | Green Water Polyculture | 0.25 |
| T16 | Green Water Polyculture | 0.5 |

Five, six, eight and nine weeks after transplanting, Seascape strawberries were harvested and assessed for brix at the time of harvest. For 3 of 4 pick dates, berries from plants receiving PT-O65 microalgae composition (both rates of 0.25 gal/A and 0.5 gal/A) showed increased brix compared to standard practice (2-10%) and the seaweed-based commercial reference (2-6%). Brix for the final harvest (4$^{th}$ pick) was the most affected by the various treatments. Compared to standard practice, the largest increases in brix were observed for 0.25 gal/A of the combination 25% *Chlorella*: 75% HS399 extracted biomass (EB) microalgae composition (13%), for 0.25 gal/A of the *Aurantiochytrium acetophilum* HS399 extracted biomass (EB) microalgae composition alone (12%), for 0.5 gal/A of PT-O65 microalgae composition (10%), and for 0.25 gal/A of Greenwater polyculture (9%).

Example 10

A trial was conducted on strawberry (var. Red Merlin) in Jupiter, Fla. to evaluate performance of the PHYCOTERRA® *Chlorella* microalgae composition and the *Aurantiochytrium acetophilum* HS399 extracted biomass (EB) microalgae composition on strawberry growth, yield and sweetness. All plots received standard fertilization regimen used by the grower for these crops, excluding biostimulants. The products were added in addition to standard fertilization. Strawberry plants were transplanted to the field. The first product application occurred at the time of transplanting and then every 14 days afterward until harvest. The first 3 applications were via drench and the remaining were via drip irrigation. The untreated control received the same amount of carrier water as other treatments at the time of each application. The microalgae compositions were shaken well before application and agitated while in the chemigation tank in order to prevent solids from settling. 4 to 6 harvests were completed during the first flush. All plots were managed according to the local standard practice (see Study Parameters below).

| STUDY PARAMETERS | |
|---|---|
| Crop | Strawberry (var. Red Merlin) |
| Location | Jupiter, FL |
| Conventional Row Spacing | 5' rows with 10" plant spacing, entire trial is 12 rows × 270' |
| Plot size minimum | Minimum 5' × 25' (5' bed size) |
| Observations | Taken from multiple subsamples per 25' section |
| Replication | 14 treatments × 8 replicates = 112 treatment plots (12 ft sections) |
| Local Standard Production | Fertility, weed, insect management, etc. |
| Standard Management Practice | Fungicide application. Record disease management measures |

Application rates of the PHYCOTERRA® *Chlorella* microalgae composition, and the *Aurantiochytrium acetophilum* HS399 extracted biomass (EB) microalgae composition were as detailed in Table 15 below. Raw data is included in the table shown in Table 16 below.

TABLE 15

Treatments

| Treatment Number | Product | Application Rate gallon/acre |
|---|---|---|
| T1 | Untreated control (UTC/standard practice) | N/A |
| T2 | HS399 Extracted Biomass (EB) | 0.3 |
| T3 | HS399 Extracted Biomass (EB) | 0.5 |
| T4 | HS399 Extracted Biomass (EB) | 1 |
| T5 | HS399 Extracted Biomass (EB) | 2 |
| T6 | PHYCOTERRA ® | 0.3 |
| T7 | PHYCOTERRA ® | 0.5 |
| T8 | PHYCOTERRA ® | 1 |
| T9 | PHYCOTERRA ® | 2 |
| T10 | Green Water Polyculture | 0.3 |
| T11 | Green Water Polyculture | 0.5 |
| T12 | Green Water Polyculture | 1 |
| T13 | Green Water Polyculture | 2 |
| T14 | Seaweed Commercial Reference | 0.5 |

TABLE 16

Treatments

| Treatment | Rate (gal/A) | % Brix at harvest | % Advantage over Standard Practice | % Advantage over Comm. Ref. |
|---|---|---|---|---|
| Standard practice | | 6.7 | | |
| Commercial reference | 0.5 | 6.5 | −3% | |
| PHYCOTERRA | 0.3 | 6.8 | 2% | 5% |
| PHYCOTERRA | 0.5 | 6.6 | −1% | 1% |
| PHYCOTERRA | 1 | 6.6 | −2% | 1% |
| PHYCOTERRA | 2 | 6.7 | 0% | 3% |
| HS399 EB | 0.3 | 6.9 | 2% | 5% |
| HS399 EB | 0.5 | 7.0 | 4% | 7% |
| HS399 EB | 1 | 6.7 | 0% | 3% |
| HS399 EB | 2 | 6.5 | −2% | 0% |
| Greenwater Polyculture | 0.3 | 6.8 | 2% | 5% |
| Greenwater Polyculture | 0.5 | 6.9 | 3% | 6% |
| Greenwater Polyculture | 1 | 6.5 | −3% | −1% |
| Greenwater Polyculture | 2 | 6.8 | 2% | 5% |

Eight weeks after transplanting, Red Merlin strawberries were harvested and assessed for brix at the time of harvest. Increases in brix were observed but were low overall as the berries were all on the lower end of the spectrum for ripe berries (<7%). Compared to standard practice, the lowest application rate of all treatments (0.3 gal/A) showed a 2% increase. Compared to the seaweed-based commercial reference, advantages for all treatments were greater (3-7%) but the rate response was not as clear.

Example 11

A trial was conducted on strawberry (var. *portola*) in Guadalupe Valley, Calif. to evaluate performance of the PHYCOTERRA® *Chlorella* microalgae composition, the *Aurantiochytrium acetophilum* HS399 whole biomass (WB) microalgae composition, the *Aurantiochytrium acetophilum* HS399 washed whole biomass (WB washed) microalgae composition, PT-O90 microalgae composition, and the combination 25% *Chlorella*: 75% HS399 whole biomass (WB) microalgae composition on strawberry growth, yield, post-harvest berry quality, and sweetness. All plots received standard local fertilization regimen used by the grower for this crop, excluding biostimulants. The products were added in addition to standard fertilization. Strawberry plants were transplanted to the field in early June 2017, according to local commercial practice. The first product application will be via drip irrigation at the time of transplanting and then every 14 days afterward until harvest. The untreated control received the same amount of carrier water as other treatments at the time of each product application. The microalgae compositions were shaken well before application and agitated, if possible, while in the chemigation tank in order to prevent solids from settling. Berries were harvested according to local commercial schedule. All plots were managed according to the local standard practice (see Study Parameters below). Raw data is shown in Table 17 below.

STUDY PARAMETERS

| | |
|---|---|
| Crop | Strawberry (var. *Portola*) |
| Location | Guadalupe Valley, CA |
| Conventional Row Spacing | 40" furrow spacing with 24" wide bed spacing, and plants on plant lines 12" apart and plant lines 12" apart |
| Harvest Schedule | As frequently as standard local grower practice with estimated 12-16 picks |
| Fumigation Schedule | Early May, 32 gal/a PicChlor60 |
| Plot size minimum | 1 double-line bed 45 ft length per plot with 80 + plants per plot |
| Trial Design | Randomized Complete Block |
| Observations | Taken from 70 plants inside 3 ft buffer zone of each plot end |
| Replication | 6 replicate plots for each treatment |
| Local Standard Production | Fertility, weed, insect management, etc. |
| Standard Management Practice | Fungicide application. Record disease management measures Fungicides will be applied weekly when flowers and fruit are present |

TABLE 17

| | | | | % Advantage over | | Day 5 Post-storage % Brix | % Advantage over | |
|---|---|---|---|---|---|---|---|---|
| Date | Treatment | Rate (gal/A) | % Brix at harvest | Standard Practice | Comm. Ref. | | Standard Practice | Comm. Ref. |
| 9/5/2017 | Standard Practice | | 6.3 | | | 7.58 | | |
| | Comm. Ref. | 0.50 | 6.1 | −2% | | 7.88 | 4% | |
| | PHYCOTERRA | 0.25 | 6.1 | −3% | −1% | 7.67 | 1% | −3% |
| | PHYCOTERRA | 0.50 | 6.2 | −2% | 1% | 8.18 | 8% | 4% |
| | PT-O90 | 0.25 | 5.9 | −6% | −4% | 7.85 | 4% | 0% |
| | PT-O90 | 0.50 | 6.2 | −1% | 1% | 7.68 | 1% | −3% |
| | HS399 WB | 0.25 | 6.0 | −5% | −2% | 7.45 | −2% | −5% |
| | HS399 WB | 0.50 | 6.2 | −1% | 1% | 7.78 | 3% | −1% |
| | HS399 WB washed | 0.25 | 5.9 | −6% | −3% | 7.98 | 5% | 1% |
| | HS399 WB washed | 0.50 | 5.9 | −7% | −4% | 7.67 | 1% | −3% |
| | Combo 399WB | 0.25 | 6.1 | −3% | −1% | 7.90 | 4% | 0% |
| | Combo 399WB | 0.50 | 6.1 | −2% | 0% | 7.85 | 4% | 0% |
| 9/16/2017 | Standard Practice | | 5.7 | | | | | |
| | Comm. Ref. | 0.50 | 5.7 | 1% | | | | |
| | PHYCOTERRA | 0.25 | 5.8 | 3% | 1% | | | |
| | PHYCOTERRA | 0.50 | 6.0 | 6% | 4% | | | |
| | PT-O90 | 0.25 | 5.9 | 4% | 3% | | | |
| | PT-O90 | 0.50 | 5.8 | 2% | 1% | | | |
| | HS399 WB | 0.25 | 6.1 | 7% | 6% | | | |
| | HS399 WB | 0.50 | 6.0 | 5% | 4% | | | |
| | HS399 WB washed | 0.25 | 5.7 | 1% | −1% | | | |
| | HS399 WB washed | 0.50 | 5.8 | 3% | 2% | | | |
| | Combo 399WB | 0.25 | 6.1 | 7% | 6% | | | |
| | Combo 399WB | 0.50 | 5.5 | −3% | −4% | | | |
| 9/25/2017 | Standard Practice | | 7.2 | | | | | |
| | Comm. Ref. | 0.50 | 7.3 | 2% | | | | |
| | PHYCOTERRA | 0.25 | 7.2 | 1% | −2% | | | |
| | PHYCOTERRA | 0.50 | 7.3 | 1% | −1% | | | |
| | PT-O90 | 0.25 | 7.2 | 0% | −2% | | | |
| | PT-O90 | 0.50 | 7.1 | −1% | −3% | | | |
| | HS399 WB | 0.25 | 7.3 | 1% | −1% | | | |
| | HS399 WB | 0.50 | 7.4 | 3% | 0% | | | |
| | HS399 WB washed | 0.25 | 7.1 | −1% | −3% | | | |
| | HS399 WB washed | 0.50 | 7.2 | 1% | −2% | | | |
| | Combo 399WB | 0.25 | 7.2 | 0% | −2% | | | |
| | Combo 399WB | 0.50 | 7.2 | 0% | −2% | | | |
| 9/27/2017 | Standard Practice | | 7.7 | | | | | |
| | Comm. Ref. | 0.50 | 7.7 | −1% | | | | |
| | PHYCOTERRA | 0.25 | 7.7 | −1% | 0% | | | |
| | PHYCOTERRA | 0.50 | 7.7 | 0% | 1% | | | |
| | PT-O90 | 0.25 | 7.8 | 1% | 2% | | | |
| | PT-O90 | 0.50 | 7.2 | −7% | −6% | | | |
| | HS399 WB | 0.25 | 7.8 | 1% | 2% | | | |
| | HS399 WB | 0.50 | 7.6 | −2% | −1% | | | |
| | HS399 WB washed | 0.25 | 7.7 | −1% | 0% | | | |
| | HS399 WB washed | 0.50 | 7.6 | −2% | −2% | | | |
| | Combo 399WB | 0.25 | 7.8 | 0% | 1% | | | |
| | Combo 399WB | 0.50 | 7.8 | 1% | 2% | | | |
| 10/6/2017 | Standard Practice | | 7.6 | | | | | |
| | Comm. Ref. | 0.50 | 7.9 | 4% | | | | |
| | PHYCOTERRA | 0.25 | 7.7 | 1% | −3% | | | |
| | PHYCOTERRA | 0.50 | 8.2 | 8% | 4% | | | |
| | PT-O90 | 0.25 | 7.9 | 4% | 0% | | | |
| | PT-O90 | 0.50 | 7.7 | 1% | −3% | | | |
| | HS399 WB | 0.25 | 7.5 | −2% | −5% | | | |
| | HS399 WB | 0.50 | 7.8 | 3% | −1% | | | |

TABLE 17-continued

Raw Data

| Date | Treatment | Rate (gal/A) | % Brix at harvest | % Advantage over Standard Practice | % Advantage over Comm. Ref. | Day 5 Post-storage % Brix | % Advantage over Standard Practice | % Advantage over Comm. Ref. |
|---|---|---|---|---|---|---|---|---|
| | HS399 WB washed | 0.25 | 8.0 | 5% | 1% | | | |
| | HS399 WB washed | 0.50 | 7.7 | 1% | −3% | | | |
| | Combo 399WB | 0.25 | 7.9 | 4% | 0% | | | |
| | Combo 399WB | 0.50 | 7.9 | 4% | 0% | | | |
| ######## | Standard Practice | | 7.2 | | | | | |
| | Comm. Ref. | 0.50 | 7.7 | 7% | | | | |
| | PHYCOTERRA | 0.25 | 8.1 | 12% | 5% | | | |
| | PHYCOTERRA | 0.50 | 7.8 | 8% | 1% | | | |
| | PT-O90 | 0.25 | 8.0 | 10% | 3% | | | |
| | PT-O90 | 0.50 | 7.5 | 3% | −3% | | | |
| | HS399 WB | 0.25 | 7.9 | 9% | 3% | | | |
| | HS399 WB | 0.50 | 7.2 | −1% | −7% | | | |
| | HS399 WB washed | 0.25 | 7.7 | 6% | 0% | | | |
| | HS399 WB washed | 0.50 | 7.2 | 0% | −6% | | | |
| | Combo 399WB | 0.25 | 7.6 | 6% | −1% | | | |
| | Combo 399WB | 0.50 | 7.2 | −1% | −7% | | | |
| 11/3/2017 | Standard Practice | | 6.6 | | | | | |
| | Comm. Ref. | 0.50 | 6.5 | −3% | | | | |
| | PHYCOTERRA | 0.25 | 6.7 | 1% | 4% | | | |
| | PHYCOTERRA | 0.50 | 6.7 | 1% | 4% | | | |
| | PT-O90 | 0.25 | 6.7 | 1% | 4% | | | |
| | PT-O90 | 0.50 | 6.5 | −2% | 1% | | | |
| | HS399 WB | 0.25 | 6.8 | 3% | 5% | | | |
| | HS399 WB | 0.50 | 6.6 | −1% | 2% | | | |
| | HS399 WB washed | 0.25 | 6.4 | −3% | −1% | | | |
| | HS399 WB washed | 0.50 | 6.5 | −3% | 0% | | | |
| | Combo 399WB | 0.25 | 6.4 | −3% | −1% | | | |
| | Combo 399WB | 0.50 | 6.8 | 2% | 5% | | | |
| ######## | Standard Practice | | 7.2 | | | | | |
| | Comm. Ref. | 0.50 | 7.2 | −1% | | | | |
| | PHYCOTERRA | 0.25 | 7.0 | −3% | −2% | | | |
| | PHYCOTERRA | 0.50 | 6.7 | −7% | −6% | | | |
| | PT-O90 | 0.25 | 6.6 | −9% | −9% | | | |
| | PT-O90 | 0.50 | 7.0 | −4% | −3% | | | |
| | HS399 WB | 0.25 | 6.8 | −6% | −5% | | | |
| | HS399 WB | 0.50 | 7.1 | −2% | −1% | | | |
| | HS399 WB washed | 0.25 | 7.3 | 0% | 1% | | | |
| | HS399 WB washed | 0.50 | 7.1 | −3% | −2% | | | |
| | Combo 399WB | 0.25 | 7.4 | 2% | 3% | | | |
| | Combo 399WB | 0.50 | 7.2 | 0% | 1% | | | |

*portola* strawberries were harvested on eight occasions between 12 and 24 weeks after transplanting and assessed for % brix at the time of harvest. Fifteen weeks after transplanting, berries were harvested and stored in cold storage for 5 days and assessed for % brix. Brix at the time of harvest was variable for treatments compared to the control. The combination 25% *Chlorella*: 75% HS399 whole biomass (WB) microalgae composition (0.25 gal/A) showed an advantage over standard practice in 4 of 8 harvests (2-7%). The PHYCOTERRA® *Chlorella* microalgae composition (0.5 gal/A) and PT-O90 microalgae composition (0.25 gal/A) showed an advantage in only 3 of 8 harvests compared to standard practice (6-8% and 4-10%, respectively). Advantages were more seldom compared to the seaweed-based commercial reference. The *Aurantiochytrium acetophilum* HS399 whole biomass (WB) microalgae composition (0.25 gal/A) showed an advantage over the seaweed commercial reference in 4 of 8 harvests (2-5%). The PHYCOTERRA® *Chlorella* microalgae composition (0.5 gal/A) showed an advantage over the commercial reference (4%) in 3 of 8 harvests. For the post-harvest brix, The PHYCOTERRA® *Chlorella* microalgae composition (0.5 gal/A) showed the largest advantage over standard practice (8%). The *Aurantiochytrium acetophilum* HS399 washed whole biomass (WB washed) microalgae composition and the combination 25% *Chlorella*: 75% HS399 whole biomass (WB) microalgae composition also had advantages at both rates (3-5%). Only the PHYCOTERRA® Chlorella microalgae composition (0.5 gal/A) had an advantage over the seaweed-based commercial reference (4%).

Example 12

For the treatments referred to in this Example as Commercial Reference+PT-O65, the commercial reference was applied first to the soil at a rate of 20 gal/acre. The PT-O65 microalgae composition was then added on top via drip irrigation. The commercial reference was only applied 3 times per season, whereas the PT-O65 microalgae composition was applied every 14 days until harvest.

For the treatments referred to in this Example as Commercial Reference+PT-O90, the commercial reference was applied first to the soil at a rate of 20 gal/acre. The PT-O90 microalgae composition was then added on top via drip irrigation. The commercial reference was only applied 3 times per season, whereas the PT-O90 microalgae composition was applied every 14 days until harvest.

A trial was conducted on strawberry (var. *portola*—Organic) in Santa Maria, Calif. to evaluate performance of various OMRI certified microalgae compositions on organic strawberry growth, yield, post-harvest berry quality, and sweetness; particularly, PT-O65 microalgae composition, PT-O90 microalgae composition, the combination OMRI certified PT-O65: microbial-based commercial reference microalgae composition, and the combination OMRI certified PT-O90: microbial-based commercial reference microalgae composition. All plots received standard local fertigation practice, including NEPTUNE'S HARVEST fertilizer and NFORCE fertilizer. A control was added with standard local fertigation practice plus 4 applications of a microbial-based commercial reference product that is standard to this location. Treatments included two versions of an OMRI certified *Chlorella* microalgae composition that differ by pasteurization temperature (PT-O65 microalgae composition and PT-O90 microalgae composition), each tested alone and each tested in combination with the microbial-based commercial reference. Strawberry plants (frigo) were transplanted to the field in June 2017, according to local commercial practice. The first product application was via drip irrigation at the time of transplanting and then every 14 days afterward through to final harvest. The untreated control received the same amount of carrier water as other treatments at the time of each product application. The microalgae compositions were shaken well before application and agitated while in the chemigation tank in order to prevent solids from settling. Berries were harvested according to local commercial schedule (twice per week during fruiting season). The timing of the commercial reference applications were once at the time of planting (6/20), once 14-21 days after planting (7/5), once in late July/early August (7/31) and the last in early September (9/11). All plots were managed according to the local standard practice (see Study Parameters below).

| STUDY PARAMETERS | |
|---|---|
| Crop | Strawberry (var. *Portola*) |
| Location | Santa Maria, CA |
| Conventional Row Spacing | Wide 4-row beds, 64-inches center-to-center; plants spaced 14 inches apart in each of the four rows |
| Harvest Schedule | As frequently as standard local grower practice with estimated 32 picks |
| Fumigation Schedule | None (Organic) |
| Plot size minimum | 1 four-row bed 25-30 ft length per plot with 80 + plants per plot. Plots will be located away from any field edges with 1-2 commercial buffer beds in between |
| Trial Design | Randomized complete block |
| Observations | Yield data taken from 40 inside plants, outside 40 combined with inside 40 for post-harvest assessments |
| Replication | 6 replicate plots for each treatment and untreated control |
| Local Standard Production | Fertility, weed, insect management, etc. |
| Standard Management Practice | Standard management practices for organic production. Record disease management measures |

Application rates of PT-O65 microalgae composition treatment, PT-O90 microalgae composition treatment, the combination Commercial Reference+PT-O65 microalgae composition treatment, and the combination Commercial Reference+PT-O90 microalgae composition treatment were as detailed in Table 18 below. Raw data is included in the table shown in Table 19 below.

TABLE 18

Treatments

| Treatment Number | Product | Application Rate gallon/acre |
|---|---|---|
| T1 | Standard practice only (UTC) | Water |
| T2 | Commercial reference (No PT-O) | 20 |
| T3 | Commercial reference + PT-O65 | 0.5 |
| T4 | Commercial reference + PT-O90 | 0.5 |
| T5 | PT-O65 | 0.25 |
| T6 | PT-O90 | 0.25 |
| T7 | PT-O65 | 0.5 |
| T8 | PT-O90 | 0.5 |

TABLE 19

Raw Data

| | | | % Brix | % Advantage over | |
|---|---|---|---|---|---|
| Holding Test | Treatment | Rate (gal/A) | Post-Storage | Standard Practice | Comm. Ref. |
| 1 | Standard practice | | 6.56 | | |
| | Comm. Ref. | 20 | 6.22 | −5% | |
| | Comm. Ref. + PT-O65 | 0.50 | 6.29 | −4% | 1% |
| | Comm. Ref. + PT-O90 | 0.50 | 6.45 | −2% | 4% |

TABLE 19-continued

Raw Data

| Holding Test | Treatment | Rate (gal/A) | % Brix Post-Storage | % Advantage over Standard Practice | % Advantage over Comm. Ref. |
|---|---|---|---|---|---|
| | PT-O65 | 0.25 | 6.45 | -2% | 4% |
| | PT-O65 | 0.50 | 6.24 | -5% | 0% |
| | PT-O90 | 0.25 | 6.25 | -5% | 0% |
| | PT-O90 | 0.50 | 6.47 | -1% | 4% |
| 2 | Standard practice | | 8.51 | | |
| | Comm. Ref. | 20 | 8.14 | -4% | |
| | Comm. Ref. + PT-O65 | 0.50 | 8.75 | 3% | 7% |
| | Comm. Ref. + PT-O90 | 0.50 | 7.99 | -6% | -2% |
| | PT-O65 | 0.25 | 8.12 | -5% | 0% |
| | PT-O65 | 0.50 | 8.10 | -5% | -1% |
| | PT-O90 | 0.25 | 8.28 | -3% | 2% |
| | PT-O90 | 0.50 | 8.22 | -4% | 1% |
| 3 | Standard practice | | 7.65 | | |
| | Comm. Ref. | 20 | 7.81 | 2% | |
| | Comm. Ref. + PT-O65 | 0.50 | 7.73 | 1% | -1% |
| | Comm. Ref. + PT-O90 | 0.50 | 7.93 | 4% | 1% |
| | PT-O65 | 0.25 | 7.76 | 1% | -1% |
| | PT-O65 | 0.50 | 7.92 | 4% | 1% |
| | PT-O90 | 0.25 | 7.89 | 3% | 1% |
| | PT-O90 | 0.50 | 7.83 | 2% | 0% |

At 11, 14 and 18 weeks after transplanting, berries were harvested and stored in cold storage for 6 days then assessed for % brix after the storage period. For the first and second holding test, most treatments had lower brix than standard practice. The exception was the combination Commercial Reference+PT-O65 microalgae composition, which had a 3% advantage. For the final holding test, the combination of Commercial Reference+PT-O90 microalgae composition, PT-O65 microalgae composition (0.5 gal/A) alone, and both rates of PT-O90 microalgae composition alone had 2-4% advantage over standard practice. By this time, the trial was beginning to be affected by a fungal infection that spread across the entire ranch which may have affected berry quality and given the products more of an advantage. Compared to the commercial reference, advantages were observed for several treatments for the first two holding tests, with the highest being the combination Commercial Reference+PT-O65 microalgae composition (7%).

Example 13

A trial was conducted on strawberry (var. *portola*) in Oxnard, Calif. to evaluate performance of various microalgae compositions on strawberry growth, yield, post-harvest berry quality, and sweetness; particularly the PHYCOTERRA® *Chlorella* microalgae composition, PT-O65 microalgae composition, the *Aurantiochytrium acetophilum* HS399 whole biomass (WB) microalgae composition, the *Aurantiochytrium acetophilum* HS399 extracted biomass (EB) microalgae composition, and the combination 25% *Chlorella*: 75% HS399 whole biomass (WB) microalgae composition. All plots receive standard local fertilization regimen used by the grower for this crop, excluding biostimulants. The microalgae compositions were added in addition to standard fertilization. Strawberry plants were transplanted to the field in July 2017, according to local commercial practice. The first product application was via drip irrigation at the time of transplanting and then every 14 days afterward through to final harvest. The untreated control received the same amount of carrier water as other treatments at the time of each product application. The microalgae compositions were shaken well before application and agitated, if possible, while in the chemigation tank to prevent solids from settling. Berries were harvested according to local commercial schedule (twice per week during the fruiting season). All plots were managed according to the local standard practice (see Study Parameters below).

| STUDY PARAMETERS | |
|---|---|
| Crop | Strawberry (var. *Portola*) |
| Location | Oxnard, CA |
| Conventional Row Spacing | Wide 4-row beds, 64-inches center-to-center; plants spaced 14 inches apart in each of the four rows |
| Harvest Schedule | As frequently as standard local grower practice with estimated 24 picks |
| Fumigation Schedule | Local practice (recorded)-timing will be in June |
| Plot size minimum | 1 four-row bed 25 ft length per plot with 80 + plants per plot. Plots will be located away from any field edges with 1-2 commercial buffer beds in between |
| Trial Design | Randomized complete block |
| Observations | Yield data taken from 40 inside plants, outside 40 combined with inside 40 for post-harvest assessments |
| Replication | 6 replicate plots for each treatment and untreated control |
| Local Standard Production | Fertility, weed, insect management, etc |
| Standard Management Practice | Standard management practices, including fungicide application. Record disease management measures. Fungicides will be applied as necessary (by grower) when flowers and fruit are present |

Application rates of the PHYCOTERRA® *Chlorella* microalgae composition, the *Aurantiochytrium acetophilum* HS399 extracted biomass (EB) microalgae composition, the *Aurantiochytrium acetophilum* HS399 whole biomass (WB) microalgae composition, PT-O65 microalgae composition, and the combination 25% *Chlorella*: 75% HS399 whole biomass (WB) microalgae composition were as detailed in Table 20 below. Raw data is included in the table shown in Table 21 below.

TABLE 20

Treatments

| Treatment Number | Product | Application Rate gallon/acre |
|---|---|---|
| T1 | Untreated control (UTC/standard practice) | Water |
| T2 | Seaweed Commercial Reference | 0.5 |
| T3 | PHYCOTERRA ® Chlorella composition | 0.25 |
| T4 | PHYCOTERRA ® Chlorella composition | 0.5 |
| T5 | HS399 Extracted Biomass (EB) | 0.25 |
| T6 | HS399 Extracted Biomass (EB) | 0.5 |
| T7 | HS399 Whole Biomass (WB) | 0.25 |
| T8 | HS399 Whole Biomass (WB) | 0.5 |
| T9 | PT-O65 | 0.25 |
| T10 | PT-O65 | 0.5 |
| T11 | 25% Chlorella: 75% HS399 WB | 0.25 |
| T12 | 25% Chlorella: 75% HS399 WB | 0.5 |

TABLE 21

Raw Data

| Holding Test | Date | Treatment | Rate (gal/A) | % Brix Post-Storage | % Advantage over Standard Practice | % Advantage over Comm. Ref. |
|---|---|---|---|---|---|---|
| 1 | 9/21/2017 | Standard Practice | | 7.5 | | |
| | | Comm. Ref. | 0.50 | 7.2 | −4% | |
| | | PHYCOTERRA ® | 0.25 | 7.3 | −3% | 1% |
| | | PHYCOTERRA ® | 0.50 | 7.3 | −3% | 1% |
| | | PT-O65 | 0.25 | 6.9 | −8% | −4% |
| | | PT-O65 | 0.50 | 7.3 | −3% | 1% |
| | | HS399 EB | 0.25 | 7.2 | −4% | 0% |
| | | HS399 EB | 0.50 | 7.0 | −7% | −3% |
| | | HS399 WB | 0.25 | 7.1 | −5% | −1% |
| | | HS399 WB | 0.50 | 7.0 | −7% | −3% |
| | | Combo 399WB | 0.25 | 7.2 | −4% | 0% |
| | | Combo 399WB | 0.50 | 7.1 | −5% | −1% |
| 2 | ######## | Standard Practice | | 7.2 | | |
| | | Comm. Ref. | 0.50 | 7.1 | −1% | |
| | | PHYCOTERRA ® | 0.25 | 7.1 | −1% | 0% |
| | | PHYCOTERRA ® | 0.50 | 7.6 | 6% | 7% |
| | | PT-O65 | 0.25 | 7.6 | 6% | 7% |
| | | PT-O65 | 0.50 | 7.7 | 7% | 8% |
| | | HS399 EB | 0.25 | 7.3 | 1% | 3% |
| | | HS399 EB | 0.50 | 7.1 | −1% | 0% |
| | | HS399 WB | 0.25 | 7.5 | 4% | 6% |
| | | HS399 WB | 0.50 | 7.4 | 3% | 4% |
| | | Combo 399WB | 0.25 | 7.7 | 7% | 8% |
| | | Combo 399WB | 0.50 | 7.3 | 1% | 3% |
| 3 | ######## | Standard Practice | | 8.30 | | |
| | | Comm. Ref. | 0.50 | 7.80 | −6% | |
| | | PHYCOTERRA ® | 0.25 | 8.30 | 0% | 6% |
| | | PHYCOTERRA ® | 0.50 | 7.80 | −6% | 0% |
| | | PT-O65 | 0.25 | 8.60 | 4% | 10% |
| | | PT-O65 | 0.50 | 8.40 | 1% | 8% |
| | | HS399 EB | 0.25 | 8.10 | −2% | 4% |
| | | HS399 EB | 0.50 | 8.00 | −4% | 3% |
| | | HS399 WB | 0.25 | 8.20 | −1% | 5% |
| | | HS399 WB | 0.50 | 8.10 | −2% | 4% |
| | | Combo 399WB | 0.25 | 8.50 | 2% | 9% |
| | | Combo 399WB | 0.50 | 8.30 | 0% | 6% |
| 4 | ######## | Standard Practice | | 9.70 | | |
| | | Comm. Ref. | 0.50 | 9.80 | 1% | |
| | | PHYCOTERRA ® | 0.25 | 9.70 | 0% | −1% |
| | | PHYCOTERRA ® | 0.50 | 9.40 | −3% | −4% |
| | | PT-O65 | 0.25 | 10.20 | 5% | 4% |
| | | PT-O65 | 0.50 | 10.00 | 3% | 2% |
| | | HS399 EB | 0.25 | 9.90 | 2% | 1% |
| | | HS399 EB | 0.50 | 9.70 | 0% | −1% |
| | | HS399 WB | 0.25 | 10.10 | 4% | 3% |
| | | HS399 WB | 0.50 | 10.40 | 7% | 6% |
| | | Combo 399WB | 0.25 | 10.30 | 6% | 5% |
| | | Combo 399WB | 0.50 | 10.40 | 7% | 6% |
| 5 | 1/18/2018 | Standard Practice | | 8.10 | | |
| | | Comm. Ref. | 0.50 | 8.20 | 1% | |
| | | PHYCOTERRA ® | 0.25 | 8.50 | 5% | 4% |
| | | PHYCOTERRA ® | 0.50 | 7.90 | −2% | −4% |
| | | PT-O65 | 0.25 | 8.90 | 10% | 9% |
| | | PT-O65 | 0.50 | 8.40 | 4% | 2% |
| | | HS399 EB | 0.25 | 8.10 | 0% | −1% |
| | | HS399 EB | 0.50 | 8.20 | 1% | 0% |
| | | HS399 WB | 0.25 | 8.10 | 0% | −1% |
| | | HS399 WB | 0.50 | 8.20 | 1% | 0% |
| | | Combo 399WB | 0.25 | 8.40 | 4% | 2% |
| | | Combo 399WB | 0.50 | 8.30 | 2% | 1% |

At 11, 15, 19, 21 and 26 weeks after transplanting, berries were harvested and stored in cold storage for 6 to 10 days and then assessed for % brix. PT-O65 microalgae composition had an advantage over standard practice in 4 of 5 holding tests (3-10%). The combination 25% Chlorella: 75% HS399 whole biomass (WB) microalgae composition had an advantage over standard practice in 4 of 5 holding tests (2-7%). Multiple treatments had an advantage over the seaweed commercial reference, but PT-O65 microalgae composition had the highest (2-10%) advantage in 4 of 5 holding tests.

Example 14

A trial was conducted on bell peppers (var. Capsicum annuum Ace) in a greenhouse in Gilbert, Ariz. to evaluate performance of the PHYCOTERRA® Chlorella microalgae composition on bell pepper sweetness. Capsicum annuum Ace is a bell pepper cultivar grown for both mature green and red ripe fruit in controlled environments. This variety was grown from seed to yield in a horticultural greenhouse and the PHYCOTERRA® Chlorella microalgae composition treatments were administered via manual drench to the soil. The purpose of this experiment was to test whether increasing rates of PHYCOTERRA® Chlorella microalgae composition can establish an optimal application rate to increase percent brix.

Replicates were irrigated with treatments bi-weekly until harvest. Data was collected on fruits within the guidelines of USDA marketable bell pepper standards. Mature green fruit was harvested once a week for 3 weeks. Red ripe fruit was harvested daily for three weeks. Fruits were juiced, and percent brix was recorded using a HI 96801 refractometer. The metric described was percent brix, which is a measure of total dissolved solids in the juice of the fruit and which equates to dissolved sugars and sweetness.

Application rates of the PHYCOTERRA® Chlorella microalgae composition as applied for red ripe and mature green bell peppers were as detailed in Table 22 below. Raw data is included in the table shown in Table 23 below.

TABLE 22

Treatments

| Treatments: | Replicate Plants | |
|---|---|---|
| | Mature Green | Red Ripe |
| Control | 4 | 4 |
| 9 mL/gal | 4 | 4 |
| 18 mL/gal | 4 | 4 |
| 37 mL/gal | 4 | 4 |
| 75 mL/gal | 4 | 4 |
| 150 mL/gal | 4 | 4 |

Replicate plants were given a slow release fertilizer (OSMOTCOTE fertilizer) and irrigated with reverse osmosis (RO) water. Every two weeks replicates were treated with corresponding treatment diluted in city water. At the end of the trial, replicate plant fruits were harvested as either mature green or red ripe. Brix measurements were taken only on qualifying fruit based on USDA standards. Fruits were juiced, and percent brix was taken on individual fruits of each replicate plant. This trial ran for 144 days from seeding to final harvest.

Figure 7:
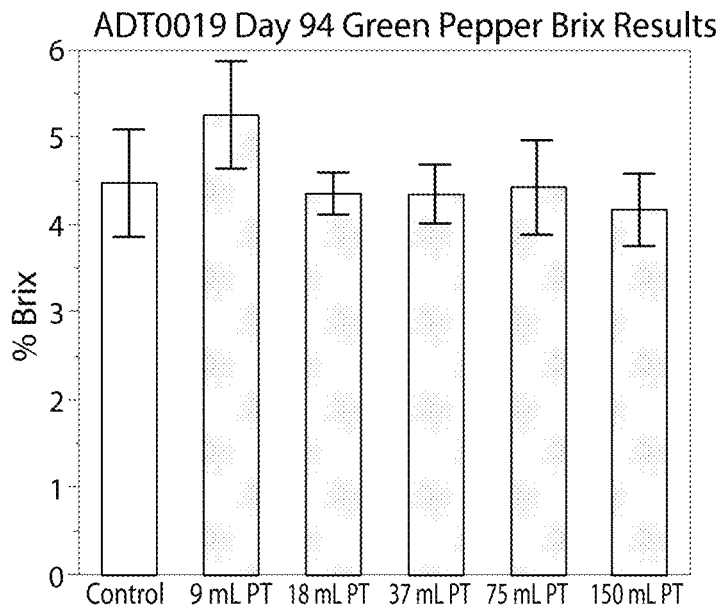
FIG. 7 is a graph showing the effects of a microalgae composition on mature green bell pepper quality, wherein the effects are observed in an increase in bell pepper sweetness (% brix) relative to the UTC.
Figure 8:
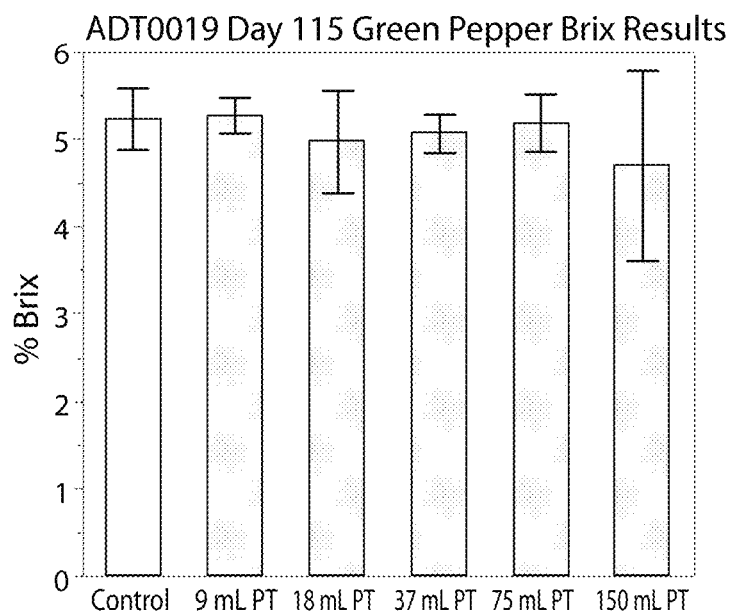
FIG. 8 is a graph showing the effects of the microalgae composition of FIG. 7 on mature green bell pepper quality, wherein the effects are observed in an increase in bell pepper sweetness (% brix) relative to the UTC.

Mature green bell peppers were harvested once a week for three weeks. USDA standard marketable fruits were juiced, percent brix was taken on individual fruits and percent was recorded. Table 23 below shows raw values for percent brix for each treatment and percent change of treatments relative to the control. The 9 ml/gal application rate resulted in a 17% increase in brix of green peppers for the earliest harvest, but no other benefits were observed. FIG. 7 shows results from the first green bell pepper harvest where bell peppers treated with 9 ml/gal of PHYCOTERRA® *Chlorella* microalgae composition demonstrated a numerical advantage over the control. FIG. 8 shows the results from the second green bell pepper harvest.

TABLE 23

Raw Data for Green Bell Pepper Harvest

| Treatment | Raw Data Harvest 1 | % change Harvest 1 | Raw Data Harvest 2 | % change Harvest 2 | Raw Data Harvest 3 | % change Harvest 3 |
|---|---|---|---|---|---|---|
| Control | 4.48 | | 5.24 | | 5.20 | |
| 9mL/gal | 5.26 | 17.41 | 5.28 | 0.76 | 4.83 | −7.05 |
| 18mL/gal | 4.36 | −2.68 | 4.98 | −4.96 | 4.83 | −7.05 |
| 37mL/gal | 4.36 | −2.68 | 5.08 | −3.05 | 4.97 | −4.49 |
| 75mL/gal | 4.44 | −0.89 | 5.20 | −0.76 | 4.97 | −4.49 |
| 150mL/gal | 4.18 | −6.70 | 4.70 | −10.31 | 5.17 | −0.64 |

Red ripe bell peppers were harvested daily over three-week intervals. USDA standard marketable fruit were juiced, and percent brix was taken on individual fruit. The average percent brix of all fruits per treatment was taken over three one-week intervals. Table 24 below shows raw values of percent brix and percent change of treatments relative to the control. The majority of the application rates resulted in brix increases in 2 of 3 harvests. The 75 mL/gal application increased Brix for red peppers in all 3 harvests at 7-14%. After the first week of harvests, 9 mL/gal, 75 mL/gal and 150 mL/gal of PHYCOTERRA® *Chlorella* microalgae composition demonstrated a numerical advantage over the control. After the second week of harvests, 18 mL/gal, 37 mL/gal and 75 mL/gal of PHYCOTERRA® *Chlorella* microalgae composition demonstrated a numerical advantage over control. After the third week of harvests, at a level of 0.1, 150 mL/gal of PHYCOTERRA® *Chlorella* microalgae composition had a statistically significant advantage over the control. 9 mL/gal, 18 mL/gal and 75 mL/gal had a numerical advantage over control.

TABLE 24

Raw Data for Red Ripe Bell Peppers

| Treatment | Raw Data Harvest 1 | % change Harvest 1 | Raw Data Harvest 2 | % change Harvest 2 | Raw Data Harvest 3 | % change Harvest 3 |
|---|---|---|---|---|---|---|
| Control | 8.20 | | 8.91 | | 8.07 | |
| 9mL/gal | 8.82 | 7.6 | 8.53 | −4.27 | 9.34 | 15.74 |
| 18mL/gal | 8.24 | 0.5 | 9.30 | 4.33 | 8.90 | 10.33 |
| 37mL/gal | 8.34 | 1.7 | 9.25 | 3.72 | 8.02 | −0.55 |
| 75mL/gal | 9.25 | 12.8 | 9.56 | 7.28 | 9.25 | 14.67 |
| 150mL/gal | 9.07 | 10.6 | 8.88 | −0.36 | 9.58 | 18.70 |

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context.

Unless otherwise stated, all exact values provided herein are representative of corresponding approximate values (e.g., all exact exemplary values provided with respect to a particular factor or measurement can be considered to also provide a corresponding approximate measurement, modified by "about," where appropriate). All provided ranges of values are intended to include the end points of the ranges, as well as values between the end points.

The description herein of any aspect or embodiment of the invention using terms such as "comprising", "having," "including," or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims and/or aspects appended hereto as permitted by applicable law.

What is claimed is:

1. An agricultural composition comprising:
   pasteurized *Chlorella* cells; and
   at least one of pasteurized *Aurantiochytrium* cells and pasteurized *Scenedesmus* cells,
   wherein the pasteurized *Chlorella* cells and the at least one of the pasteurized *Aurantiochytrium* cells and the pasteurized *Scenedesmus* cells have been pasteurized at a temperature ranging from 50° C. up to 90° C. and
   wherein the pasteurized *Chlorella* cells are whole cells or extracted cells, the pasteurized *Aurantiochytrium* cells are whole cells or extracted cells, and the pasteurized *Scenedesmus* cells are whole cells.

2. The composition of claim 1 comprising the pasteurized *Chlorella* cells and the pasteurized *Aurantiochytrium* cells.

3. The composition of claim 2 comprising the pasteurized *Chlorella* cells and the pasteurized *Aurantiochytrium* cells in a ratio of 25:75, 50:50 or 75:25.

4. The composition of claim 2 wherein the pasteurized *Chlorella* cells are whole cells and the pasteurized *Aurantiochytrium* cells are whole cells.

5. The composition of claim 2 wherein the pasteurized *Chlorella* cells are whole cells and the pasteurized *Aurantiochytrium* cells are extracted cells.

6. The composition of claim 1 comprising the pasteurized *Chlorella* cells and the pasteurized *Scenedesmus* cells.

7. The composition of claim 1 further comprising a stabilizer to prevent proliferation of unwanted microorganisms in the composition.

8. The composition of claim 1 wherein the pasteurized *Aurantiochytrium* cells are pasteurized *Aurantiochytrium acetophilum* HS399 cells.

9. An agricultural composition comprising at least one of pasteurized *Aurantiochytrium* cells and pasteurized *Scenedesmus* cells, wherein the at least one of the pasteurized *Aurantiochytrium* cells and the pasteurized *Scenedesmus* cells have been pasteurized at a temperature ranging from 50° C. up to 90° C., and
   wherein the pasteurized *Aurantiochytrium* cells are whole cells or extracted cells and the pasteurized *Scenedesmus* cells are whole cells.

10. The composition of claim 9 further comprising a stabilizer to prevent proliferation of unwanted microorganisms in the composition.

11. An agricultural composition comprising a microalgae biomass, the microalgae biomass comprising two species of pasteurized microalgae, the two species of pasteurized microalgae being *Chlorella* and *Aurantiochytrium*, wherein the two species of pasteurized microalgae are pasteurized at a temperature ranging from 50° C. up to 90° C., wherein the *Chlorella* is whole biomass or extracted biomass, wherein the *Aurantiochytrium* is whole biomass or extracted biomass, and wherein the composition causes enhancement of at least one plant characteristic selected from improved shelf life, increased fruit water retention, and diminished needle-drop.

12. The composition of claim 11 wherein the microalgae biomass comprises *Chlorella* and *Aurantiochytrium*, wherein the ratio of the first species of microalgae and *Aurantiochytrium* is between 1:20 and 1:1.

13. The composition of claim 12 wherein the wherein the ratio of *Chlorella* and *Aurantiochytrium* is between 1:4 and 1:1.

14. The composition of claim 11 wherein the microalgae biomass comprises pasteurized *Chlorella* microalgae and pasteurized *Aurantiochytrium acetophilum* HS399 microalgae.

15. The composition of claim 14 wherein the ratio of pasteurized *Chlorella* microalgae to pasteurized *Aurantiochytrium acetophilum* HS399 microalgae is 25:75, 50:50 or 75:25.

16. The composition of claim 14 wherein the pasteurized Chlorella microalgae is whole biomass and the pasteurized *Aurantiochytrium acetophilum* HS399 microalgae is extracted biomass or wherein the pasteurized *Chlorella* microalgae is whole biomass and the pasteurized *Aurantiochytrium acetophilum* HS399 microalgae is whole biomass.

17. The composition of claim 11 wherein the microalgae biomass further comprises whole pasteurized *Scenedesmus* microalgae cells.

18. The composition of claim 11 further comprising a stabilizer to prevent proliferation of unwanted microorganisms in the composition.

19. A composition for enhancing at least one plant characteristic in agriculture, the composition comprising pasteurized *Scenedesmus* cells, wherein the pasteurized *Scenedesmus* cells have been pasteurized at a temperature ranging from 50° C. up to 90° C. and wherein the pasteurized *Scenedesmus* cells are whole cells.

20. A composition for enhancing at least one plant characteristic in agriculture, the composition comprising pasteurized *Aurantiochytrium* cells, wherein the pasteurized *Aurantiochytrium* cells have been pasteurized at a temperature ranging from 50° C. up to 90° C. and wherein the pasteurized *Aurantiochytrium* cells are whole cells or extracted cells.

21. The composition of claim 20 wherein the pasteurized *Aurantiochytrium* cells are pasteurized *Aurantiochytrium acetophilum* HS399 cells.

* * * * *